US005693532A

United States Patent [19]
McSwiggen et al.

[11] Patent Number: 5,693,532
[45] Date of Patent: Dec. 2, 1997

[54] RESPIRATORY SYNCYTIAL VIRUS RIBOZYMES

[75] Inventors: James McSwiggen; Kenneth Draper, both of Boulder; Pam Pavco, Layfayette, all of Colo.; Tod Woolf, Watertown, Mass.

[73] Assignee: Ribozyme Pharmaceuticals, Inc., Boulder, Colo.

[21] Appl. No.: 334,847

[22] Filed: Nov. 4, 1994

[51] Int. Cl.$^6$ .............................. C12N 15/85; C12Q 1/68
[52] U.S. Cl. ..................... 435/366; 435/6; 435/91.31; 435/172.3; 435/320.1; 435/325; 536/23.1; 536/23.2; 536/24.5; 514/44
[58] Field of Search ..................... 435/240.1, 240.2, 435/6, 91.31, 172.1; 325/172.3; 366/320.1; 536/23.1, 23.2, 24.5; 514/44

[56] References Cited

U.S. PATENT DOCUMENTS 4,987,071 1/1991 Cech ..................... 435/91.31

FOREIGN PATENT DOCUMENTS

| | | |
|---|---|---|
| 9103162 | 3/1991 | WIPO . |
| 9207065 | 4/1992 | WIPO . |
| 9315187 | 8/1993 | WIPO . |
| 9323569 | 11/1993 | WIPO . |
| 9402595 | 2/1994 | WIPO . |
| 9413688 | 6/1994 | WIPO . |

OTHER PUBLICATIONS

Stull et al. Pharm Res. 12: 465-483 (1996).
*Antiviral Agents and Viral Diseases of Man*, 3rd ed. Galasso, Whitely and Merigan eds., Raven Press Ltd., NY, pp. 352-360 (1990).
Barik et al., "Transcription of Human Respiratory Syncytial Virus Genome RNA In Vitro: Requirement of Cellular Factor(s)," *J. Virology* 66:6813-6818 (1992).
Carter, "Adeno-Associated Virus Vectors," *Curr Opi. Biotech.* 3:533-539 (1992).
Chen et al., "Multitarget-Ribozyme Directed to Cleave at up to Nine Highly Conserved HIV-1 env RNA Regions Inhibits HIV-1 Replication-Potential Effectiveness Against Most Presently Sequenced HIV-1 Isolates," *Nucleic Acids Research* 20:4581-4589 (1992).
Chowrira et al., "In Vitro and in Vivo Comparison of Hammerhead, Hairpin, and Hepatitis Delta Virus Self-Processing Ribozyme Cassettes," *J. Biol. Chem.* 269:25856-25864 (1994).
Chowrira and Burke, "Extensive Phosphorothioate Substitution Yields Highly Active and Nuclease-Resistant Hairpin Ribozymes," *Nucleic Acids Res.* 20:2835-2840 (1992).
Collins et al., "Nucleotide Sequences For the Gene Junctions of Human Respiratory Syncytial Virus Reveal Distinctive Features of Intergenic Structure and Gene Order," *Proc. Natl. Acad. Sci. USA* 83:4594-4598 (1986).
Collins and Olive, "Reaction Conditions and Kinetics of Self-Cleavage of a Ribozyme Derived From Neurospora VS RNA," *Biochemistry* 32:2795-2799 (1993).

Connors et al., "Pulmonary Histopathology Induced by Respiratory Syncytial Virus (RSV) Challenge of Formalin-Inactivated RSV-Immunized BALB/c Mice is Abrogated by Depletion of CD4+ T Cells," *J. Virology* 66:7444-7451 (1992).
Dropulic et al., "Functional Characterization of a U5 Ribozyme: Intracellular Suppression of Human Immunodeficiency Virus Type I Expression," *J. Virol.* 66:1432-1441 (1992).
Elroy-Stein and Moss, "Cytoplasmic Expression System Based on Constitutive Synthesis of Bacteriophage T7 RNA Polymerase in Mammalian Cells," *Proc. Natl. Acad. Sci. USA* 87:6743-7 (1990).
Gao and Huang, "Cytoplasmic Expression of a Reporter Gene by Co-Delivery of T7 RNA Polymerase and T7 Promoter Sequence with Cationic Liposomes," *Nucleic Acids Res.* 21:2867-72 (1993).
Guerrier-Takada et al., "The RNA Moiety of Ribonuclease P Is the Catalytic Subunit of the Enzyme," *Cell* 35:849-857 (1983).
Hall, "Ch. 136—Respiratory Syncytial Virus," *Principles and Practice of Infectious Diseases*, pp. 1265-1279.
Hampel et al., "'Hairpin' Catalytic RNA Model: Evidence for Helices and Sequence Requirement for Substrate RNA", *Nucleic Acids Research* 18:299-304 (1990).
Hampel and Tritz, "RNA Catalytic Properties of the Minimum (-)sTRSV Sequence," *Biochemistry* 28:4929 (1989).
Haseloff and Gerlach, "Simple RNA Enzymes with New and Highly Specific Endoribonuclease Activities," *Nature* 334:585-591 (1988).
Huang et al., "Characterization of the 10 proteins of human respiratory syncytial virus: Identification of a fourth envelope-associated protein," *Virus Research* 2:157-173 (1985).
Jaeger et al., "Improved Predictions of Secondary Structures for RNA," *Proc. Natl. Acad. Sci. USA* 86:7706-7710 (1989).
Jeffries and Symons, "A Catalytic 13-mer Ribozyme," *Nucleic Acids Research* 17:1371-1377 (1989).
Johnson et al., "The G Glycoprotein of Human Respiratory Syncytial Viruses of Subgroups A and B: Extensive Sequence Divergence Between Antigenically Related Protein," *Proc. Natl. Acad. Sci. USA* 84:5625-5629 (1987).
Johnson and Collins, "The A and B Subgroups of Human Respiratory Syncytial Virus Comparison of Intergenic and Gene-overlap Sequences," *J. General Virology* 69:2901-2906 (1988).
Kashani-Sabet et al., "Reversal of the Malignant Phenotype by an Anti-ras Ribozyme," *Antisense Research & Development* 2:3-15 (1992).
Kubota et al., "Field Trials on a Live Bovine Respiratory Syncytial Virus Vaccine in Calves," *J. Vet. Med. Sci.* 54:957-962 (1992).

(List continued on next page.)

*Primary Examiner*—John L. LeGuyader
*Attorney, Agent, or Firm*—Lyon & Lyon LLP

[57] ABSTRACT

An enzymatic RNA molecule which cleaves respiratory syncytial virus (RSV) genomic and RSV encoded RNA.

14 Claims, 7 Drawing Sheets

OTHER PUBLICATIONS

L'Huillier et al., "Cytoplasmic Delivery of Ribozymes Leads to Efficient Reduction in α–Lactalbumin mRNA Levels in C1271 Mouse," *Embo J.* 11:4411–4418 (1992).

Lieber et al., "Stable High–Level Gene Expression in Mammalian Cells by T7 Phage $NA Polymerase," *Methods Enzymol.* 217:47–66 (1993).

Lisziewicz et al., "Inhibition of Human Immunodeficiency Virus Type 1 Replication by Regulated Expression of a Polymeric Tat Activation Response RNA Decoy as a Strategy for Gene Therapy in AIDS," *Proc. Natl. Acad. Sci. U.S.A.* 90:8000–8004 (1993).

McIntosh and Chanock, "Respiratory Syncytial Virus," *Virology*, B. N. Fields ed., Raven Press Ltd. NY pp. 1045–1072 (1990).

Milligan and Uhlenbeck, "Synthesis of Small RNAs Using T7 RNA Polymerase," *Methods Enzymol.* 180:51–62 (1989).

Morris et al., "Recovery of Cytopathogenic Agent From Chimpanzees with Coryza (22538)", pp. 544–549.

Ohkawa et al., "Activities of HIV–RNA Targeted Ribozymes Transcribed From a 'Shot–Gun' Type Ribozyme–trimming Plasmid," *Nucleic Acids Symp. Ser.* 27:15–16 (1992).

Ojwang et al., "Inhibition of Human Immunodeficiency Virus Type 1 Expression by a Hairpin Ribozyme," *Proc. Natl. Acad. Sci. USA* 89:10802–10806 (1992).

Perreault et al., "Mixed Deoxyribo– and Ribo–Oligonucleotides with Catalytic Activity," *Nature* 344:565–567 (1990).

Perrotta and Been, "Cleavage of Oligoribonucleotides by a Ribozyme Derived from the Hepatitis δ Virus RNA Sequence," *Biochemistry* 31:16–21 (1992).

Pieken et al., "Kinetic Characterization of Ribonuclease–Resistant 2'–Modified Hammerhead Ribozymes," *Science* 253:314–317 (1991).

Respiratory Syncytial Virus Activity, U.S., 1993, *Mmwr Morb Mortal Wkly, Rep.* 42, pp. 971–973 (Dec. 1993).

Rossi et al., "Ribozymes as Anti–HIV–1 Therapeutic Agents: Principles, Applications, and Problems," *Aids Research and Human Retroviruses* 8:183 (1992).

Sarver et al., "Ribozymes as Potential Anti–HIV–1 Therapeutic Agents" *Science* 247:1222–1225 (1990).

Saville and Collins, "A Site–Specific Self–Cleavage Reaction Performed by a Novel RNA In Neurospora Mitochondria," *Cell* 61:685–696 (1990).

Saville and Collins, "RNA–Mediated Ligation of Self–Cleavage Produces of a Neurospora Mitochondrial Plasmid Transcript," *Proc. Natl. Acad. Sci. USA* 88:8826–8830 (1991).

Scanlon et al., "Ribozyme–Mediated Cleavage of c–fos mRNA Reduces Gene Expression of DNA Synthesis Enzymes and Metallothionein," *Proc. Natl. Acad. Sci. USA* 88:10591–10595 (1991).

Scaringe et al., "Chemical synthesis of biologically active oligoribonucleotides using β–cyanoethyl protected ribonucleoside phosphoramidites," *Nucl Acids Res.* 18:5433–5441 (1990).

Taira et al., "Construction of a novel RNA–transcript–trimming plasmid which can be used both in vitro in place of run–off and (G)–free transcriptions and in vivo as multi-sequences transcription vectors," *Nucleic Acids Research* 19:5125–30 (1991).

Tristam et al., "Immunogenicity and Safety of Respiratory Syncytial Virus Subunit Vaccine in Seropositive Children 18–36 Months Old," *J. Infect. Dis.* 167:191–195 (1993).

Uhlenbeck, "A Small Catalytic Oligoribonucletoide," *Nature* 328:596–600 (1987).

Usman and Cedergren, "Exploiting the chemical synthesis of RNA," *TIBS* 17:334–339 (1992).

Usman et al.,"Automated Chemical Synthesis of Long Oligoribonucleotides Using 2'–O–Silylated Ribonucleoside 3'–OPhosphoramidtes on a Controlled–Pore Glass Support: Synthesis of a 43–Nucleotide Sequence Similar to the 3'–Half Molecule of an *Escherichia coli* Formylmethoionine tRNA," *J. Am. Chem. Soc.*109:7845–7854 (1987).

Ventura et al., "Activation of HIV–Specific Ribozyme Activity by Self–Cleavage," *Nucleic Acids Research* 21:3249–3255 (1993).

Weerasinghe et al., "Resistance of Human Immunodeficiency Virus Type 1—(HIV–1) Infection in Human CD4+ Lymphocyte–Derived Cell Lines Conferred by Using Retroviral Vectors Expressing an HIV–1 RNA–Specific Ribozyme," *Journal of Virology* 65:5531–5534 (1991).

Woolf et al., "Specificity of Antisense Oligonucleotides in vivo," *Proc. Natl. Acad. Sci. USA* 89:7305–7309 (1992).

Yu et al., "A Hairpin Ribozyme Inhibits Expression of Diverse Strains of Human Immunodeficiency Virus Type 1," *Proc. Natl. Acad. Sci. U S A* 90:6340–6344 (1993).

Zabner et al., "Adenovirus–Mediated Gene Transfer Transiently Corrects the Chloride Transport Defect in Nasal Epithelia of Patients with Cystic Fibrosis," *Cell* 75:207–216 (1993).

Zhou et al., "Synthesis of Function mRNA in Mammalian ells by Bacteriophage T3 RNA Polymerase," *Mol. Cell. Biol.* 10:4529–4537 (1990).

Ballantyne et al., "Nucleotide sequence of the cDNA for murine intercellular adhesion molecule-1 (ICAM-1)," *Nucleic Acids Research* 17:5853 (1989).

Barinaga, "Ribozymes: Killing the Messenger," *Science* 262:1512–1514 (1993).

Cotten, "The in vivo application of ribozymes," *TIBTECH* 8:174–178 (1990).

Edgington, "Ribozymes: Stop Making Sense," *Biotechnology* 10:256–262 (1992).

Kita et al., "Sequence and expression of rat ICAM-1," *Biochem. Biophys. Acta* 1131:108–110 (1992).

Simons et al., "ICAM, an adhesion ligand of LFA-1, is homologous to the neutral cell adhesion molecule NCAM," *Nature* 331:624–627 (1988).

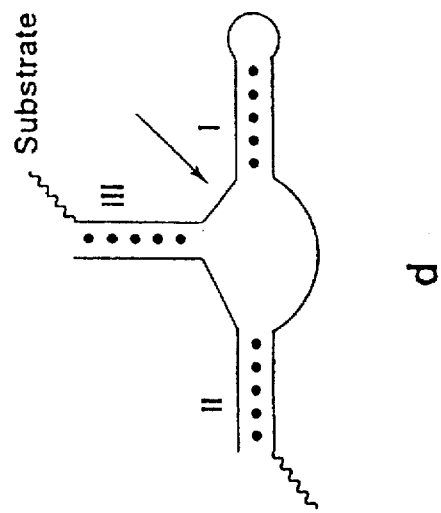
FIG. 2a.
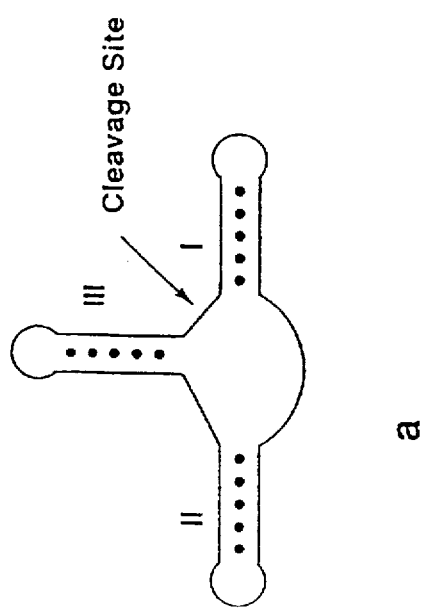
FIG. 2b.
FIG. 2c.
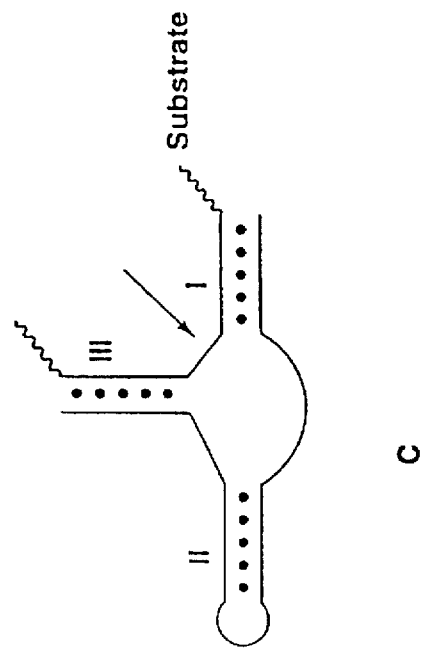
FIG. 2d.

- Body-labeled transcript (not purified)
- DNA oligo (10 nM, 100 nM and 1000 nM)
- RNAse H (0.08 - 1.0 u/μl)
- 37°C, 10 min

Genetic map of RSV strain A2.

FIG. 7.

RESPIRATORY SYNCYTIAL VIRUS RIBOZYMES

BACKGROUND OF THE INVENTION

This invention relates to the use of ribozymes as inhibitors of respiratory syncytial virus (RSV) production, and in particular, the inhibition of RSV replication.

The following is a discussion of relevant ad, none of which is admitted to be prior art to the present invention.

RSV is a member of the virus family paramyxoviridae and is classified under the genus Pneumovirus (for a review see Mcintosh and Chanock, 1990 in Virology ed. B. N. Fields, pp. 1045, Raven Press Ltd. NY). The infectious virus particle is composed of a nucleocapsid enclosed within an envelope. The nucleocapsid is composed of a linear negative single-stranded non-segmented RNA associated with repeating subunits of capsid proteins to form a compact structure and thereby protect the RNA from nuclease degradation. The entire nucleocapsid is enclosed by the envelope. The size of the virus particle ranges from 150–300 nm in diameter. The complete life cycle of RSV takes place in the cytoplasm of infected cells and the nucleocapsid never reaches the nuclear compartment (Hall, 1990 in Principles and Practice of Infectious Diseases ed. Mandell et al., Churchill Livingstone, NY).

The RSV genome encodes ten viral proteins essential for viral production. RSV protein products include two structural glycoproteins (G and F) found in the envelope spikes, two matrix proteins [M and M2 (22K)] found in the inner membrane, three proteins localized in the nucleocapsid (N, P and L), one protein that is present on the surface of the infected cell (SH), and two nonstructural proteins [NS1 (1C) and NS2 (1B)] found only in the infected cell. The mRNAs for the 10 RSV proteins have similar 5' and 3' ends. UV-inactivation studies suggest that a single promoter is used with multiple transcription initiation sites (Barik et al., 1992 J. Virol. 66, 6813). The order of transcription corresponding to the protein assignment on the genomic RNA is 1C, 1B, N, P, M, SH, G, F, 22K and L genes (Huang et al., 1985 Virus Res. 2, 157) and transcript abundance corresponds to the order of gene assignment (for example the 1C and 1B mRNAs are much more abundant than the L mRNA. Synthesis of viral message begins immediately after RSV infection of cells and reaches a maximum at 14 hours post-infection (Mcintosh and Chanock, supra).

There are two antigenic subgroups of RSV, A and B, which can circulate simultaneously in the community in varying proportions in different years (Mcintosh and Chanock, supra). Subgroup A usually predominates. Within the two subgroups there are numerous strains. By the limited sequence analysis available it seems that homology at the nucleotide level is more complete within than between subgroups, although sequence divergence has been noted within subgroups as well. Antigenic determinates result primarily from both surface glycoproteins, F and G. For F, at least half of the neutralization epitopes have been stably maintained over a period of 30 years. For G however, A and B subgroups may be related antigenically by as little as a few percent. On the nucleotide level, however, the majority of the divergence in the coding region of G is found in the sequence for the extracellular domain (Johnson et al., 1987, Proc. Natl. Acad. Sci. USA 84, 5625).

Respiratory Syncytial Virus (RSV) is the major cause of lower respiratory tract illness during infancy and childhood (Hall, supra) and as such is associated with an estimated 90,000 hospitalizations and 4500 deaths in the United States alone (Update: respiratory syncytial virus activity—United States, 1993, Mmwr Morb Mortal Wkly Rep, 42, 971). Infection with RSV generally outranks all other microbial agents leading to both pneumonia and bronchitis. While primarily affecting children under two years of age, immunity is not complete and reinfection of older children and adults, especially hospital care givers (Mcintosh and Chanock, supra), is not uncommon. Immunocompromised patients are severely affected and RSV infection is a major complication for patients undergoing bone marrow transplantation.

Uneventful RSV respiratory disease resembles a common cold and recovery is in 7 to 12 days. Initial symptoms (rhinorrhea, nasal congestion, slight fever, etc.) are followed in 1 to 3 days by lower respiratory tract signs of infection that include a cough and wheezing. In severe cases, these mild symptoms quickly progress to tachypnea, cyanosis, and listlessness and hospitalization is required. In infants with underlying cardiac or respiratory disease, the progression of symptoms is especially rapid and can lead to respiratory failure by the second or third day of illness. With modern intensive care however, overall mortality is usually less than 5% of hospitalized patients (Mcintosh and Chanock, supra).

At present, neither an efficient vaccine nor a specific antiviral agent is available. An immune response to the viral surface glycoproteins can provide resistance to RSV in a number of experimental animals, and a subunit vaccine has been shown to be effective for up to 6 months in children previously hospitalized with an RSV infection (Tristam et al., 1993, J. Infect. Dis. 167, 191). An attenuated bovine RSV vaccine has also been shown to be effective in calves for a similar length of time (Kubota et al., 1992 J. Vet. Med. Sci. 54, 957). Previously however, a formalin-inactivated RSV vaccine was implicated in greater frequency of severe disease in subsequent natural infections with RSV (Connors et al., 1992 J. Virol. 66, 7444).

The current treatment for RSV infection requiring hospitalization is the use of aerosolized ribavirin, a guanosine analog [Antiviral Agents and Viral Diseases of Man, 3rd edition. 1990. (eds. G. J. Galasso, R. J. Whitley, and T. C. Merigan) Raven Press Ltd., NY.]. Ribavirin therapy is associated with a decrease in the severity of the symptoms, improved arterial oxygen and a decrease in the amount of viral shedding at the end of the treatment period. It is not certain, however, whether ribavirin therapy actually shortens the patients' hospital stay or diminishes the need for supportive therapies (Mcintosh and Chanock, supra). The benefits of ribavirin therapy are especially clear for high risk infants, those with the most serious symptoms or for patients with underlying bronchopulmonary or cardiac disease. Inhibition of the viral polymerase complex is supported as the main mechanism for inhibition of RSV by ribavirin, since viral but not cellular polypeptide synthesis is inhibited by ribavirin in RSV-infected cells [Antiviral Agents and Viral Diseases of Man, 3rd edition. 1990. (eds. G. J. Galasso, R. J. Whitley, and T. C. Merigan) Raven Press Ltd., NY]. Since ribavirin is at least partially effective against RSV infection when delivered by aerosolization, it can be assumed that the target cells are at or near the epithelial surface. In this regard, RSV antigen had not spread any deeper than the superficial layers of the respiratory epithelium in autopsy studies of fatal pneumonia (Mcintosh and Chanock, supra).

Jennings et al., WO 94/13688 indicates that targets for specific types of ribozymes include respiratory syncytical virus.

SUMMARY OF THE INVENTION

The invention features novel enzymatic RNA molecules, or ribozymes, and methods for their use for inhibiting production of respiratory syncytial virus (RSV). Such ribozymes can be used in a method for treatment of diseases caused by these related viruses in man and other animals. The invention also features cleavage of the genomic RNA and mRNA of these viruses by use of ribozymes. In particular, the ribozyme molecules described are targeted to the NS1 (1C), NS2 (1B) and N viral genes. These genes are known in the art (for a review see Mcintosh and Chanock, 1990 supra and FIG. 7).

By "inhibit" is meant that the activity or level of mRNAs encoded by RSV is reduced below that observed in the absence of the ribozyme, and preferably is below that level observed in the presence of an inactive RNA molecule able to bind to the same site on the mRNA, but unable to cleave that RNA.

By "enzymatic RNA molecule" it is meant an RNA molecule which has complementarity in a substrate binding region to a specified gene target, and also has an enzymatic activity which is active to specifically cleave RNA in that target. That is, the enzymatic RNA molecule is able to intermolecularly cleave RNA and thereby inactivate a target RNA molecule. This complementarity functions to allow sufficient hybridization of the enzymatic RNA molecule to the target RNA to allow the cleavage to occur. One hundred percent complementarity is preferred, but complementarity as low as 50–75% may also be useful in this invention. By "equivalent" RNA to RSV is meant to include those naturally occurring viral RNA molecules associated with respiratory diseases in various animals, including human, bovine, and mouse.

By "gene" is meant to refer to either the protein coding regions of the cognate mRNA, RSV genome or any regulatory regions in the RNA which regulate synthesis of the protein or stability of the mRNA.

By "complementarity" is meant a nucleic acid that can form hydrogen bond(s) with other RNA sequence by either traditional Watson-Crick or other non-traditional types (for example, Hoogsteen type) of base-paired interactions.

Ribozymes that cleave the specified sites in RSV mRNAs represent a novel therapeutic approach to respiratory disorders. Applicant indicates that ribozymes are able to inhibit the activity of RSV and that the catalytic activity of the ribozymes is required for their inhibitory effect. Those of ordinary skill in the art, will find that it is clear from the examples described that other ribozymes that cleave these sites in RSV mRNAs encoding 1C, 1B and N proteins may be readily designed and are within the invention. Also, those of ordinary skill in the art, will find that it is clear from the examples described that ribozymes cleaving other mRNAs encoded by RSV (P, M, SH, G, F, 22K and L) and the genomic RNA may be readily designed and are within the invention.

Six basic varieties of naturally-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over other technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf, T. M., et al., 1992, *Proc. Natl. Acad. Sci. USA*, 89, 7305–7309). Thus, the specificity of action of a ribozyme is greater than that of an antisense oligonucleotide binding the same RNA site.

In preferred embodiments of this invention, the enzymatic nucleic acid molecule is formed in a hammerhead or hairpin motif, but may also be formed in the motif of a hepatitis delta virus, group I intron or RNaseP RNA (in association with an RNA guide sequence) or Neurospora VS RNA. Examples of such hammerhead motifs are described by Rossi et al., 1992, *AIDS Research and Human Retroviruses* 8, 183, of hairpin motifs by Hampel et al., EP0360257, Hampel and Tritz, 1989 *Biochemistry* 28, 4929, and Hampel et al., 1990 *Nucleic Acids Res.* 18, 299, and an example of the hepatitis delta virus motif is described by Perrotta and Been, 1992 *Biochemistry* 31, 16; of the RNaseP motif by Guerrier-Takada et al., 1983 *Ceil* 35, 849, Neurospora VS RNA ribozyme motif is described by Collins (Saville and Collins, 1990 *Cell* 61, 685–696; Saville and Collins, 1991 *Proc. Nalt. Acad. Sci.* USA 88, 8826–8830; Collins and Olive, 1993 *Biochemistry* 32, 2795–2799) and of the Group I intron by Cech et al., U.S. Pat. No. 4,987,071. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

The invention provides a method for producing a class of enzymatic cleaving agents which exhibit a high degree of specificity for the RNA of a desired target. The enzymatic nucleic acid molecule is preferably targeted to a highly conserved sequence region of a target RSV mRNAs encoding 1C, 1B and N proteins such that specific treatment of a disease or condition can be provided with either one or several enzymatic nucleic acids. Such enzymatic nucleic acid molecules can be delivered exogenously to specific cells as required. Alternatively, the ribozymes can be expressed from DNA vectors that are delivered to specific cells.

Synthesis of nucleic acids greater than 100 nucleotides in length is difficult using automated methods, and the therapeutic cost of such molecules is prohibitive. In this invention, small enzymatic nucleic acid motifs (e.g., of the hammerhead or the hairpin structure) are used for exogenous delivery. The simple structure of these molecules increases the ability of the enzymatic nucleic acid to invade targeted regions of the mRNA structure. However, these catalytic RNA molecules can also be expressed within cells from eucaryotic promoters (e.g., Scanlon et al., 1991, *Proc. Natl. Acad. Sci. USA*, 88, 10591–5; Kashani-Sabet et al., 1992 *Antisense Res. Dev.*, 2, 3–15; Dropulic et al., 1992 *J. Virol*, 66, 1432–41; Weerasinghe et al., 1991 *J. Virol.* 65, 5531–4; Ojwang et al., 1992 *Proc. Natl. Acad. Sci.* USA 89, 10802–6; Chen et al., 1992 *Nucleic Acids Res.*, 20, 4581–9; Sarver et al., 1990 *Science* 247, 1222–1225). Those skilled in the art realize that any ribozyme can be expressed in eucaryotic cells from the appropriate DNA vector. The activity of such ribozymes can be augmented by their release from the primary transcript by a second ribozyme (Draper et al., PCT WO 93/23569, and Sullivan et al., PCT WO94/02595, both hereby incorporated in their totality by reference herein; Ohkawa et al., 1992 *Nucleic Acids Symp. Ser.*, 27, 15–6; Taira et al., 1991, *Nucleic Acids Res.*, 19, 5125–30; Ventura et al., 1993 *Nucleic Acids Res.*, 21, 3249–55; Chowrira et al., 1994 *J. Biol. Chem.* 269, 25856).

Such ribozymes are useful for the prevention of the diseases and conditions discussed above, and any other diseases or conditions that are related to the level of RSV activity in a cell or tissue. By "related" is meant that the inhibition of RSV genomic RNA and RSV encoded mRNAs and thus reduction in the level of virus activity will relieve to some extent the symptoms of the disease or condition.

Ribozymes are added directly, or can be complexed with cationic lipids, packaged within liposomes, or otherwise delivered to target cells. The RNA or RNA complexes can be locally administered to relevant tissues ex vivo, or in vivo through inhalation injection, infusion pump or stent, with or without their incorporation in biopolymers. In preferred embodiments, the ribozymes have binding arms which are complementary to the sequences in Tables II, IV, VI, VIII and IX. Examples of such ribozymes are shown in Tables III, V, VII–IX. Examples of such ribozymes consist essentially of sequences defined in these Tables. By "consists essentially of" is meant that the active ribozyme contains an enzymatic center equivalent to those in the examples, and binding arms able to bind mRNA such that cleavage at the target site occurs. Other sequences may be present which do not interfere with such cleavage.

In another aspect of the invention, ribozymes that cleave target molecules and inhibit RSV activity are expressed from transcription units inserted into DNA, RNA, or viral vectors. Preferably, the recombinant vectors capable of expressing the ribozymes are locally delivered as described above, and transiently persist in target cells. Once expressed, the ribozymes cleave the target mRNA. The recombinant vectors are preferably DNA plasmids or adenovirus vectors. However, other mammalian cell vectors that direct the expression of RNA may be used for this purpose.

Other features and advantages of the invention will be apparent from the following description of the preferred embodiments thereof, and from the claims.

DESCRIPTION OF THE PREFERRED EMBODIMENTS

The drawings will first briefly be described.

DRAWINGS

FIG. 1 is a diagrammatic representation of the hammerhead ribozyme domain known in the art. Stem II can be $\geq 2$ base-pair long.

FIG. 2a is a diagrammatic representation of the hammerhead ribozyme domain known in the art; FIG. 2b is a diagrammatic representation of the hammerhead ribozyme as divided by Uhlenbeck (1987, *Nature*, 327, 596–600) into a substrate and enzyme portion; FIG. 2c is a similar diagram showing the hammerhead divided by Haseloff and Gerlach (1988, *Nature*, 334, 585–591) into two portions; and FIG. 2d is a similar diagram showing the hammerhead divided by Jeffries and Symons (1989, *Nucl. Acids. Res.*, 17, 1371–1371) into two portions.

FIG. 3 is a diagramatic representation of the general structure of a hairpin ribozyme. Helix 2 (H2) is provided with a least 4 base pairs (i.e., n is 1, 2, 3 or 4) and helix 5 can be optionally provided of length 2 or more bases (preferably 3–20 bases, i.e., m is from 1–20 or more). Helix 2 and helix 5 may be covalently linked by one or more bases (i.e., r is $\geq 1$ base). Helix 1, 4 or 5 may also be extended by 2 or more base pairs (e.g., 4–20 base pairs) to stabilize the ribozyme structure, and preferably is a protein binding site. In each instance, each N and N' independently is any normal or modified base and each dash represents a potential base-pairing interaction. These nucleotides may be modified at the sugar, base or phosphate. Complete base-pairing is not required in the helices, but is preferred. Helix 1 and 4 can be of any size (i.e., o and p is each independently from 0 to any number, e.g., 20) as long as some base-pairing is maintained. Essential bases are shown as specific bases in the structure, but those in the art will recognize that one or more may be modified chemically (abasic, base, sugar and/or phosphate modifications) or replaced with another base without significant effect. Helix 4 can be formed from two separate molecules, i.e., without a connecting loop. The connecting loop when present may be a ribonucleotide with or without modifications to its base, sugar or phosphate. "q" is $\geq 2$ bases. The connecting loop can also be replaced with a non-nucleotide linker molecule. H, refers to bases A, U or C. Y refers to pyrimidine bases. "" refers to a chemical bond.

Figure 1:
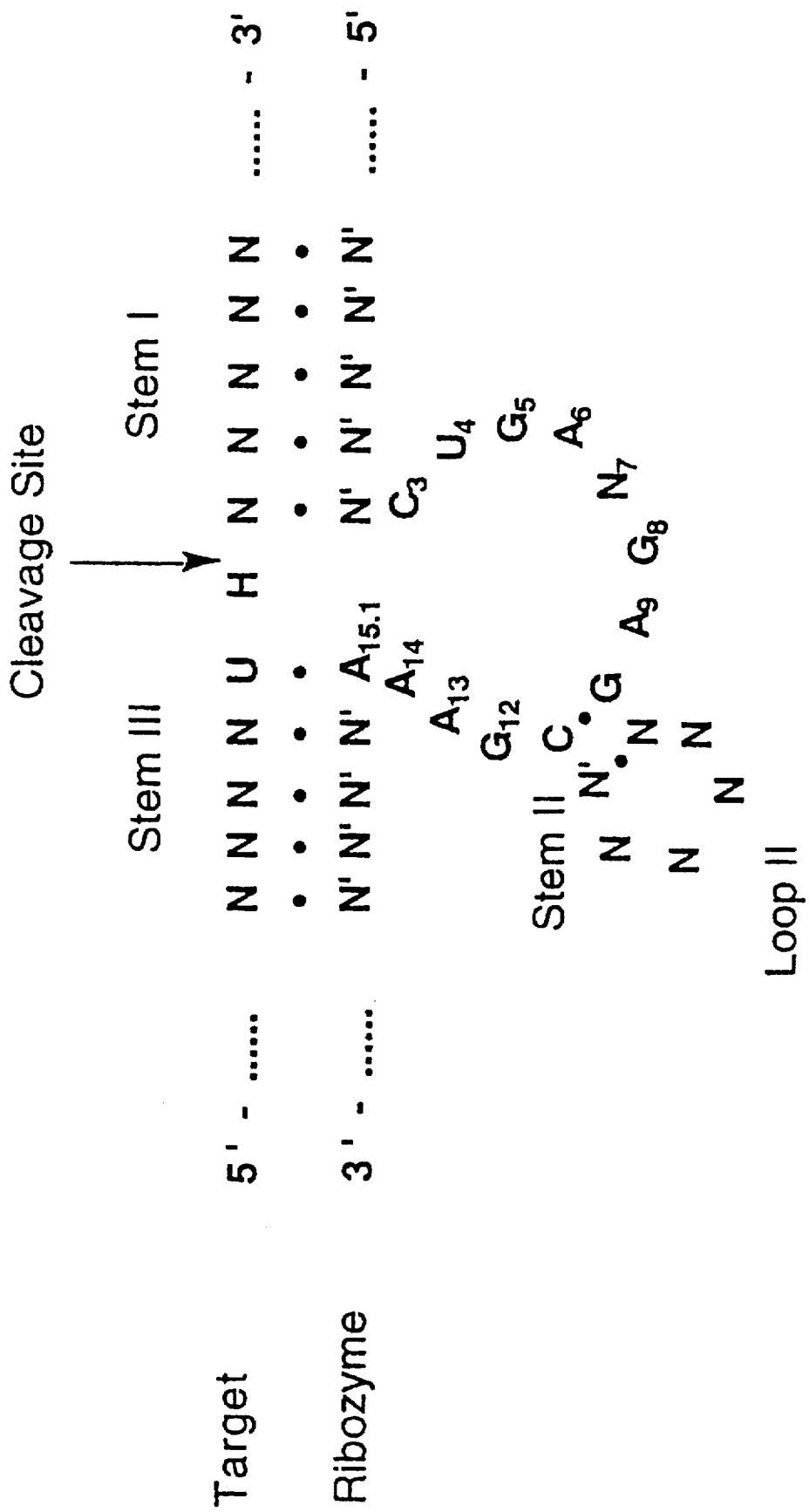
Figure 3:
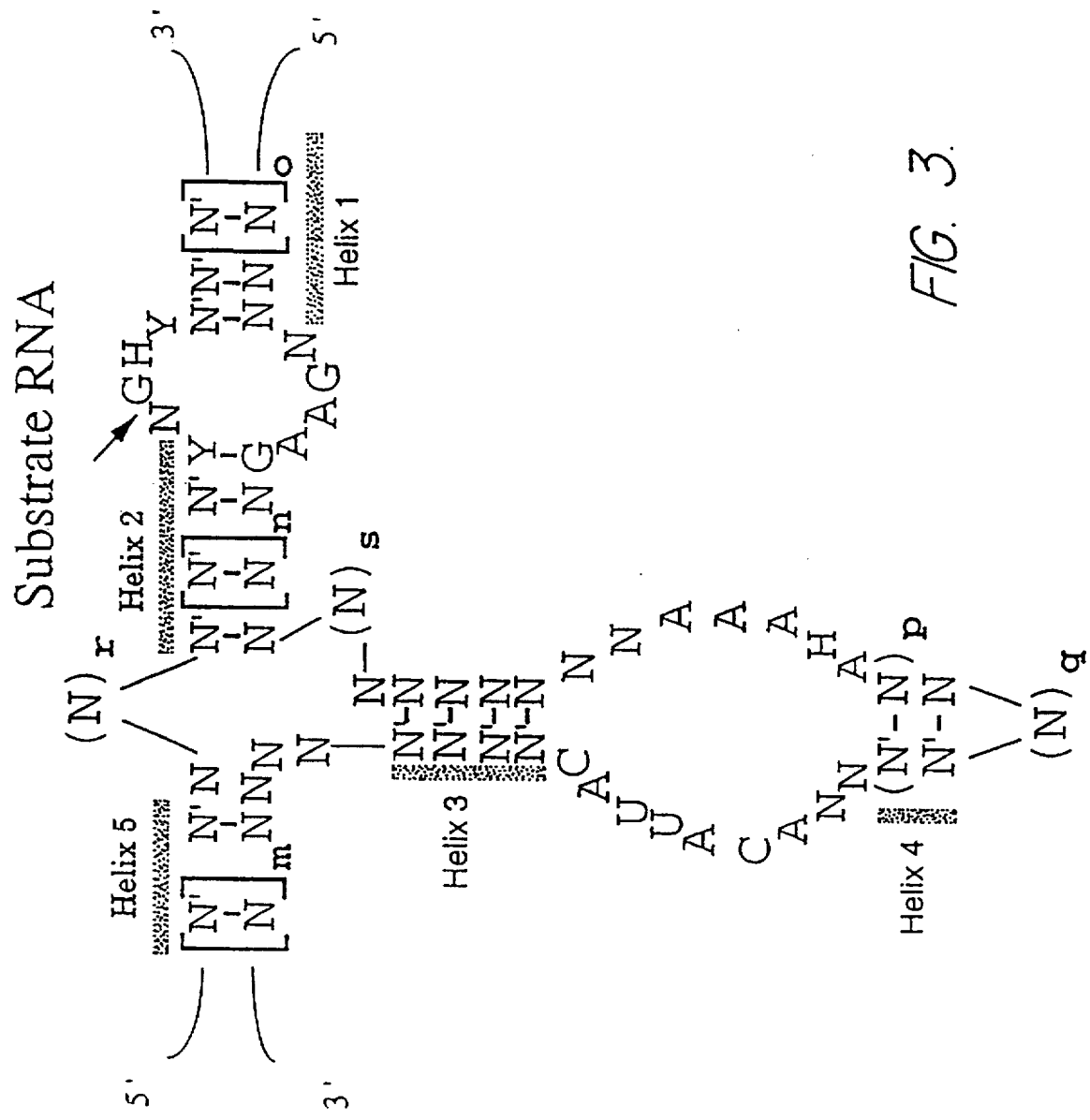
Figure 4:
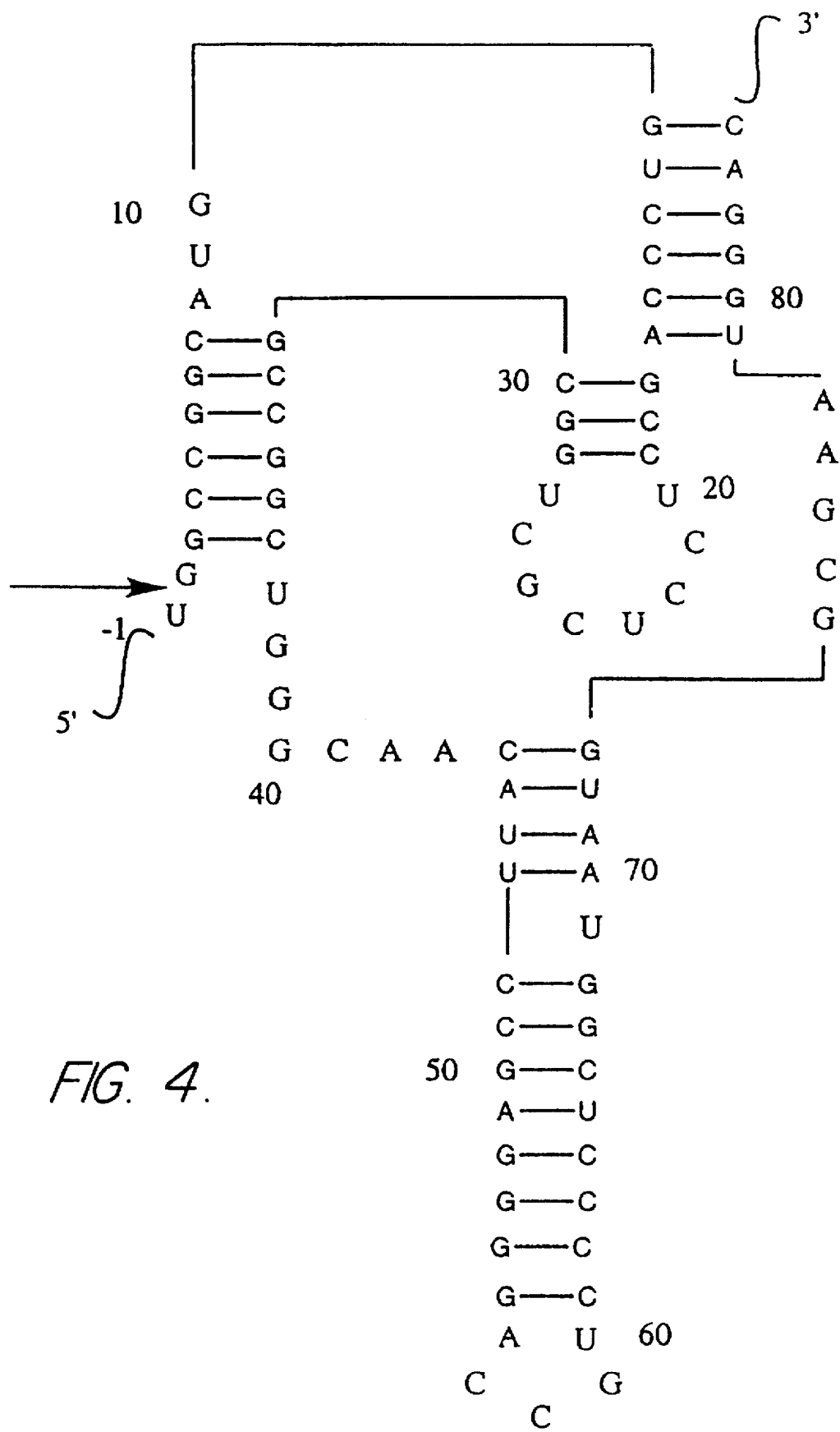
FIG. 4 is a representation of the general structure of the hepatitis delta virus ribozyme domain known in the art.
Figure 5:
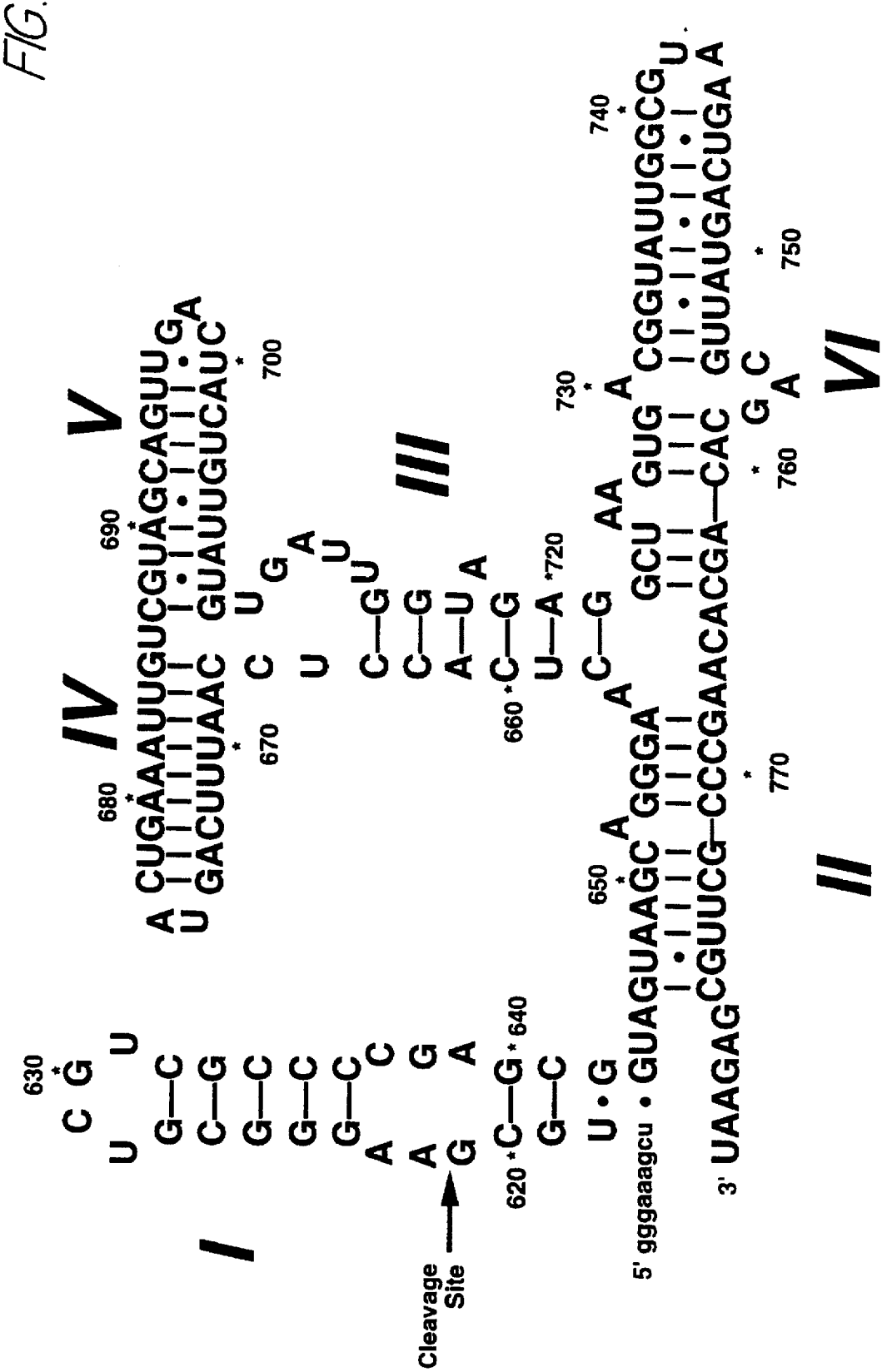
FIG. 5 is a representation of the general structure of the VS RNA ribozyme domain.
Figure 6:
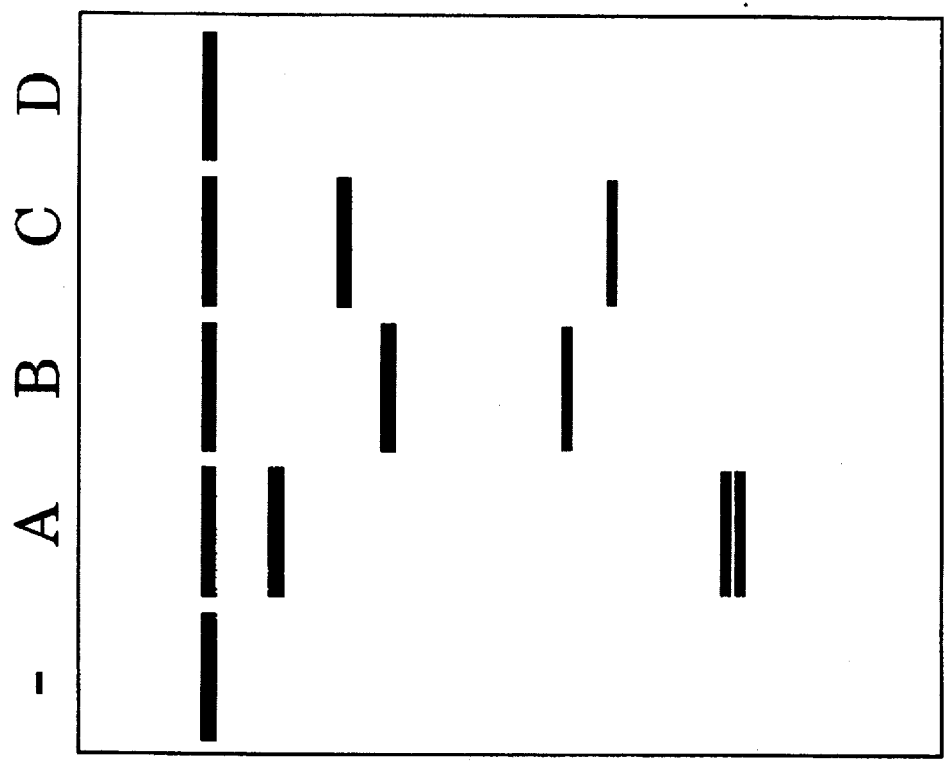
Figure 6:
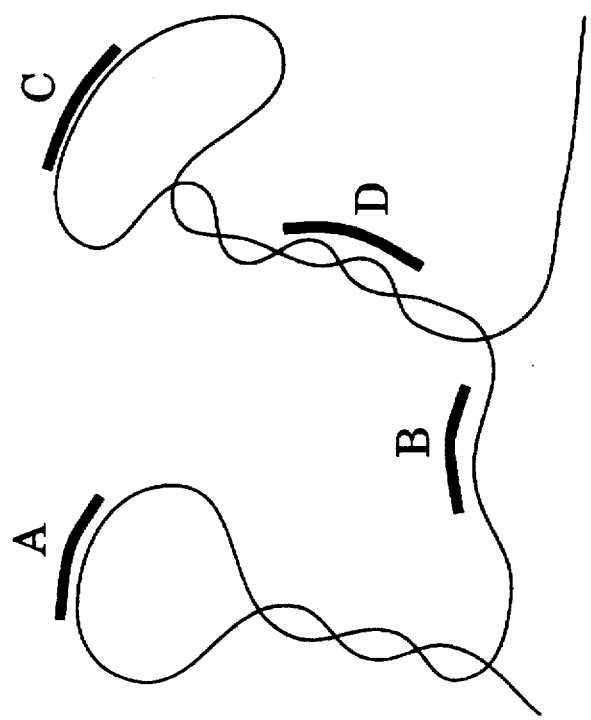

FIG. 6 is a schematic representation of an RNAseH accessibility assay. Specifically, the left side of FIG. 6 is a diagram of complementary DNA oligonucleotides bound to accessible sites on the target RNA. Complementary DNA oligonucleotides are represented by broad lines labeled A, B, and C. Target RNA is represented by the thin, twisted line. The right side of FIG. 6 is a schematic of a gel separation of uncut target RNA from a cleaved target RNA. Detection of target RNA is by autoradiography of body-labeled, T7 transcript. The bands common to each lane represent uncleaved target RNA; the bands unique to each lane represent the cleaved products.

Figure 7:
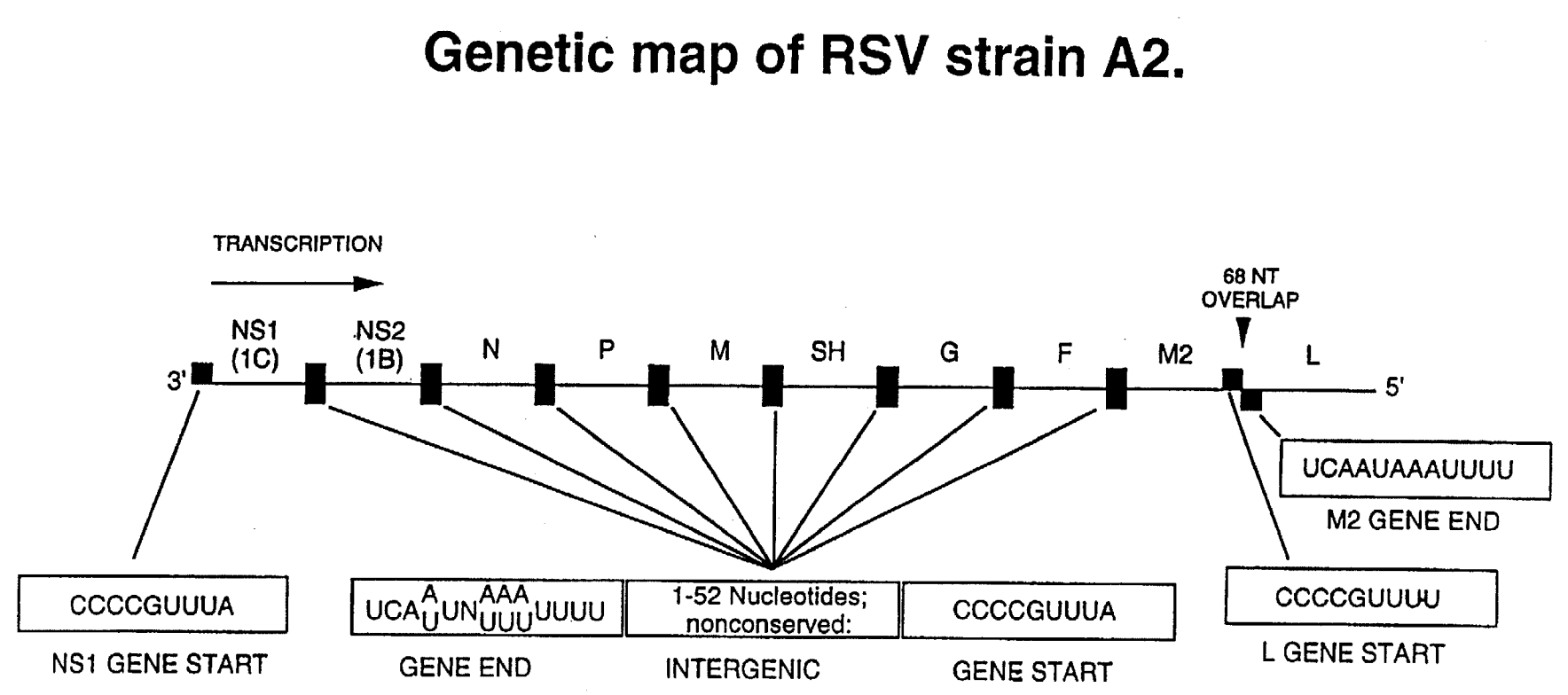

FIG. 7 is a diagrammatic representation of the genetic map of RSV strain A2.

RIBOZYMES

Ribozymes of this invention block to some extent RSV production and can be used to treat disease or diagnose such disease. Ribozymes will be delivered to cells in culture and to cells or tissues in animal models of respiratory disorders. Ribozyme cleavage of RSV encoded mRNAs or the genomic RNA in these systems may alleviate disease symptoms.

Target Sites

Targets for useful ribozymes can be determined as disclosed in Draper et al., "Method and reagent for treatment of arthritic conditions U.S. Ser. No. 08/152,487, filed Nov. 12, 1993, and hereby incorporated by reference herein in totality. Rather than repeat the guidance provided in those documents here, below are provided specific examples of such methods, not limiting to those in the art. Ribozymes to such targets are designed as described in those applications and synthesized to be tested in vitro and in vivo, as also described.

While all ten RSV encoded proteins (1C, 1B, N, P, M, SH, 22K, F, G, and L) are essential for viral life cycle and are all potential targets for ribozyme cleavage, certain proteins (mRNAs) are more favorable for ribozyme targeting than the others. For example RSV encoded proteins 1C, 1B, SH and 22K are not found in other members of the family paramyxoviridae and appear to be unique to RSV. In contrast the ectodomain of the G protein and the signal sequence of the F protein show significant sequence divergence at the nucleotide level among various RSV sub-groups (Johnson et al., 1987 supra). RSV proteins 1C, 1B and N are highly conserved among various subtypes at both the nucleotide and amino acid levels. Also, 1C, 1B and N are the most abundant of all RSV proteins.

The sequence of human RSV mRNAs encoding 1C, 1B and N proteins are screened for accessible sites using a computer folding algorithm. Hammerhead or hairpin ribozyme cleavage sites were identified. These sites are shown in Tables II, IV, V, VIII and IX (All sequences are 5' to 3' in the tables.) The nucleotide base position is noted in the Tables as that site to be cleaved by the designated type of ribozyme Hammerhead or hairpin ribozymes are designed that could bind and are individually analyzed by computer folding (Jaeger et al., 1989 Proc. Natl. Acad. Sci. USA, 86, 7706–7710) to assess whether the ribozyme sequences fold into the appropriate secondary structure. Those ribozymes with unfavorable intramolecular interactions between the binding arms and the catalytic core are eliminated from consideration. Varying binding arm lengths can be chosen to optimize activity. Generally, at least 5 bases on each arm are able to bind to, or otherwise interact with, the target RNA.

Referring to FIG. 6, mRNA is screened for accessible cleavage sites by the method described generally in McSwiggen, U.S. patent application Ser. No. 07/883,849 filed on May 1, 1992, entitled "Assay for ribozyme target site", hereby incorporated by reference herein. Briefly, DNA oligonucleotides representing potential hammerhead or hairpin ribozyme cleavage sites are synthesized. A polymerase chain reaction is used to generate substrates for T7 RNA polymerase transcription from human RSV cDNA clones. Labeled RNA transcripts are synthesized in vitro from the templates. The oligonucleotides and the labeled transcripts are annealed, RNAseH is added and the mixtures are incubated for the designated times at 37° C. Reactions are stopped and RNA separated on sequencing polyacrylamide gels. The percentage of the substrate cleaved is determined by autoradiographic quantitation using a Phosphor Imaging system. From these data, hammerhead or hairpin ribozyme sites are chosen as the most accessible.

Ribozymes of the hammerhead or hairpin motif are designed to anneal to various sites in the mRNA message. The binding arms are complementary to the target site sequences described above. The ribozymes are chemically synthesized. The method of synthesis used follows the procedure for normal RNA synthesis as described in Usman et al., 1987 J. Am. Chem. Soc., 109, 7845–7854 and in Scaringe et al., 1990 Nucleic Acids Res., 18, 5433–5441 and makes use of common nucleic acid protecting and coupling groups, such as dimethoxytrityl at the 5'-end, and phosphoramidites at the 3'-end. The average stepwise coupling yields were >98%. Inactive ribozymes were synthesized by substituting a U for $G_5$ and a U for $A_{14}$ (numbering from Hertel et al., 1992 Nucleic Acids Res., 20, 3252). Hairpin ribozymes are synthesized in two parts and annealed to reconstruct the active ribozyme (Chowrira and Burke, 1992 *Nucleic Acids Res.*, 20, 2835–2840). Hairpin ribozymes are also synthesized from DNA templates using bacteriophage T7 RNA polymerase (Milligan and Uhlenbeck, 1989, *Methods Enzymol.* 180, 51). All ribozymes are modified extensively to enhance stability by modification with nuclease resistant groups, for example, 2'-amino, 2'-C-allyl, 2'-flouro, 2'-o-methyl, 2'-H (for a review see Usman and Cedergren, 1992 *TIBS* 17, 34). Ribozymes are purified by gel electrophoresis using general methods or are purified by high pressure liquid chromatography (HPLC; See Usman et al., Synthesis, deprotection, analysis and purification of RNA and ribozymes, filed May, 18, 1994, U.S. Ser. No. 08/245, 736 the totality of which is hereby incorporated herein by reference) and are resuspended in water.

The sequences of the chemically synthesized ribozymes useful in this study are shown in Tables III, V, VII, VIII and IX. Those in the art will recognize that these sequences are representative only of many more such sequences where the enzymatic portion of the ribozyme (all but the binding arms) is altered to affect activity. For example, stem-loop II sequence of hammerhead ribozymes listed in Tables III and V (5'-GGCCGAAAGGCC-3') can be altered (substitution, deletion, and/or insertion) to contain any sequences provided a minimum of two base-paired stem structure can form. Similarly, stem-loop IV sequence of hairpin ribozymes listed in Tables VIII and IX (5'-CACGUUGUG-3') can be altered (substitution, deletion, and/or insertion) to contain any sequence, provided a minimum of two base-paired stem structure can form. The sequences listed in Tables III, V, VII, VIII and IX may be formed of ribonucleotides or other nucleotides or non-nucleotides. Such ribozymes are equivalent to the ribozymes described specifically in the Tables.

Optimizing Ribozyme Activity

Ribozyme activity can be optimized as described by Stinchcomb et al., supra. The details will not be repeated here, but include altering the length of the ribozyme binding arms (stems I and III, see FIG. 2c), or chemically synthesizing ribozymes with modifications that prevent their degradation by serum ribonucleases (see e.g., Eckstein et al., International Publication No. WO 92/07065; Perrault et al., 1990 Nature 344, 565; Pieken et al., 1991 Science 253, 314; Usman and Cedergren, 1992 Trends in Biochem. Sci. 17, 334; Usman et al., International Publication No. WO 93/15187; and Rossi et al., International Publication No. WO 91/03162, as well as Usman, N. et al. U.S. patent application Ser. No. 07/829,729, and Sproat, European Patent Application 92110298.4 which describe various chemical modifications that can be made to the sugar moieties of enzymatic RNA molecules. Modifications which enhance their efficacy in cells, and removal of stem II bases to shorten RNA synthesis times and reduce chemical requirements. (All these publications are hereby incorporated by reference herein.), Sullivan, et al., supra, describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination is locally delivered by direct injection or by use of a catheter, infusion pump or stent. Other routes of delivery include, but are not limited to, aerosol inhalation, intravascular, intramuscular, subcutaneous or joint injection, oral (tablet or pill form), topical, systemic, ocular, intraperitoneal and/or intrathecal delivery. More detailed descriptions of ribozyme delivery and administration are provided in Sullivan et al., supra and Draper et al., supra which have been incorporated by reference herein. Because RSV infection appears limited to lung epithelial cells, aerosol inhalation of a ribozyme formulation is preferred.

Another means of accumulating high concentrations of a ribozyme(s) within cells is to incorporate the ribozyme-encoding sequences into a DNA expression vector. Transcription of the ribozyme sequences are driven from a promoter for eucaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990 Proc. Natl. Acad. Sci. USA, 87, 6743–7; Gao and Huang 1993 Nucleic Acids Res., 21, 2867–72; Lieber et al., 1993 Methods Enzymol., 217, 47–66; Zhou et al., 1990 Mol. Cell. Biol., 10, 4529–37). Several investigators have demonstrated that ribozymes expressed from such promoters can function in mammalian cells (e.g. Kashani-Sabet et al., 1992 Antisense Res. Dev., 2, 3–15; Ojwang et al., 1992 Proc. Natl. Acad. Sci. USA, 89, 10802–6; Chen et al., 1992 Nucleic Acids Res., 20, 4581–9; Yu et al., 1993 Proc. Natl. Acad. Sci. USA, 90, 6340–4; L'Huillier et al., 1992 EMBO J. 11, 4411–8; Lisziewicz et al., 1993 Proc. Natl. Acad. Sci. U.S.A., 90, 8000–4). The above ribozyme transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral, sindbis virus, semliki forest virus vectors).

In a preferred embodiment of the invention, a transcription unit expressing a ribozyme that cleaves mRNAs encoded by RSV is inserted into a plasmid DNA vector or an adenovirus or adeno-associated virus DNA viral vector. Both viral vectors have been used to transfer genes to the lung and both vectors lead to transient gene expression (Zabner et al., 1993 Cell 75, 207; Carter, 1992 Curr. Opi. Biotech. 3, 533). The adenovirus vector is delivered as recombinant adenoviral particles. The DNA may be delivered alone or complexed with vehicles (as described for RNA above). The recombinant adenovirus or AAV particles are locally administered to the site of treatment, e.g., by direct inhalation, through incubation or inhalation in vivo or by direct application to cells or tissues ex vivo.

In another preferred embodiment of the invention, a transcription unit expressing a ribozyme that cleaves RSV encoded mRNAs is inserted into a retrovirus vector for sustained expression of ribozyme(s). In preferred embodiments, the ribozyme is administered to the site of infection with RSV in an appropriate liposomal vesicle.

EXAMPLE 1: RS.V HAMMERHEAD RIBOZYMES

By engineering ribozyme motifs we have designed several ribozymes directed against RSV encoded mRNA sequences. These ribozymes are synthesized with modifications that improve their nuclease resistance. The ability of ribozymes to cleave target sequences in vitro is evaluated.

Numerous common cell lines can be infected with RSV for experimental purposes. These include HeLa, Vero and several primary epithelial cell lines. A cotton rat animal model of experimental human RSV infection is also available, and the bovine RSV is quite homologous to the human viruses. Rapid clinical diagnosis is through the use of kits designed for the immunofluorescence staining of RSV-infected cells or an ELISA assay, both of which are adaptable for experimental study. RSV encoded mRNA levels will be assessed by Northern analysis, RNAse protection, primer extension analysis or quantitative RT-PCR. Ribozymes that block the induction of RSV activity and/or 1C, 1B and N protein encoding mRNAs by more than 90% will be identified.

RNA ribozymes and/or genes encoding them will be delivered either free, with liposome delivery, cationic lipid delivery, adeno-associated virus vector delivery, adenovirus vector delivery, retrovirus vector delivery or plasmid vector delivery in these animal model experiments. One dose (or a few infrequent doses) of a stable anti-RSV ribozymes or a gene construct that constitutively expresses the ribozyme may abrogate tissue damage in these respiratory diseases.

Diagnostic Uses

Ribozymes of this invention may be used as diagnostic tools to examine genetic drift and mutations within diseased cells or to detect the presence of RSV RNA in a cell. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNAs associated with RSV related condition. Such RNA is detected by determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two ribozymes, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype (i.e., RSV) is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

Other embodiments are within the following claims.

TABLE I

Characteristics of Ribozymes

Group I Introns

Size: ~200 to >1000 nucleotides.

Requires a U in the target sequence immediately 5' of the cleavage site.

Binds 4–6 nucleotides at 5' side of cleavage site.

Over 75 known members of this class. Found in *Tetrahymena thermophila* rRNA, fungal mitochondria, chloroplasts, phage T4, blue-green algae, and others.

RNAseP RNA (M1 RNA)

Size: ~290 to 400 nucleotides.

RNA portion of a ribonucleoprotein enzyme. Cleaves tRNA precursors to form mature tRNA.

Roughly 10 known members of this group all are bacterial in origin.

Hammerhead Ribozyme

Size: ~13 to 40 nucleotides.

Requires the target sequence UH immediately 5' of the cleavage site.

Binds a variable number nucleotides on both sides of the cleavage site.

14 known members of this class. Found in a number of plant pathogens (virusolds) that use RNA as the infectious agent (FIG. 1)

Hairpin Ribozyme

Size: ~50 nucleotides.

Requires the target sequence GUC immediately 3' of the cleavage site.

Binds 4–6 nucleotides at 5' side of the cleavage site and a variable number to the 3' side of the cleavage site.

Only 3 known member of this class. Found in three plant pathogen (satellite RNAs of the tobacco ringspot virus, arabis mosaic virus and chicory yellow mottle virus) which uses RNA as the infectious agent (FIG. 3).

Hepatitis Delta Virus (HDV) Ribozyme

Size: 50–60 nucleotides (at present).

Cleavage of target RNAs recently demonstrated.

Sequence requirements not fully determined.

Binding sites and structural requirements not fully determined, although no sequences 5' of cleavage site are required.

Only 1 known member of this class. Found in human HDV (FIG. 4).

Neurospora VS RNA Ribozyme

Size: ~144 nucleotides (at present)

Cleavage of target RNAs recently demonstrated.

Sequence requirements not fully determined.

Binding sites and structural requirements not fully determined. Only 1 known member of this class. Found in Neurospora VS RNA (FIG. 5).

TABLE II

RSV (1C) HH Target Sequence

| nt. Position | Target Sequence | Sequence ID No. | nt. Position | Target Sequence | Sequence ID No. |
|---|---|---|---|---|---|
| 10 | GGCAAAU A AGAAUUU | 7 | 165 | UACAUUU A ACUAACG | 47 |
| 16 | UAAGAAU U UGAUAAG | 8 | 169 | UUUAACU A ACGCUUU | 48 |
| 17 | AAGAAUU U GAUAAGU | 9 | 175 | UAACGCU U UGGCUAA | 49 |
| 21 | AUUUGAU A AGUACCA | 10 | 176 | AACGCUU U GGCUAAG | 50 |
| 25 | GAUAAGU A CCACUUA | 11 | 181 | UUUGGCU A AGGCAGU | 51 |
| 31 | UACCACU U AAAUUUA | 12 | 192 | CAGUGAU A CAUACAA | 52 |
| 32 | ACCACUU A AAUUUAA | 13 | 196 | GAUACAU A CAAUCAA | 53 |
| 36 | CUUAAAU U UAACUCC | 14 | 201 | AUACAAU C AAAUUGA | 54 |
| 37 | UUAAAUU U AACUCCC | 15 | 206 | AUCAAAU U GAAUGGC | 55 |
| 38 | UAAAUUU A ACUCCCU | 16 | 216 | AUGGCAU U GUGUUUG | 56 |
| 42 | UUUAACU C CCUUGGU | 17 | 221 | AUUGUGU U UGUGCAU | 57 |
| 46 | ACUCCCU U GGUUAGA | 18 | 222 | UUGUGUU U GUGCAUG | 58 |
| 50 | CCUUGGU U AGAGAUG | 19 | 231 | UGCAUGU U AUUACAA | 59 |
| 51 | CUUGGUU A GAGAUGG | 20 | 232 | GCAUGUU A UUACAAG | 60 |
| 67 | CAGCAAU U CAUUGAG | 21 | 234 | AUGUUAU U ACAAGUA | 61 |
| 68 | AGCAAUU C AUUGAGU | 22 | 235 | UGUUAUU A CAAGUAG | 62 |
| 71 | AAUUCAU U GAGUAUG | 23 | 241 | UACAAGU A GUGAUAU | 63 |
| 76 | AUUGAGU A UGAUAAA | 24 | 247 | UAGUGAU A UUUGCCC | 64 |
| 81 | GUAUGAU A AAAGUUA | 25 | 249 | GUGAUAU U UGCCCUA | 65 |
| 87 | UAAAAGU U AGAUUAC | 26 | 250 | UGAUAUU U GCCCUAA | 66 |
| 88 | AAAAGUU A GAUUACA | 27 | 256 | UUGCCCU A AUAAUAA | 67 |
| 92 | GUUAGAU U ACAAAAU | 28 | 259 | CCCUAAU A AUAAUAU | 68 |
| 93 | UUAGAUU A CAAAAUU | 29 | 262 | UAAUAAU A AUAUUGU | 69 |
| 100 | ACAAAAU U UGUUUGA | 30 | 265 | UAAUAAU A UUGUAGU | 70 |

TABLE II-continued

RSV (1C) HH Target Sequence

| nt. Position | Target Sequence | Sequence ID No. | nt. Position | Target Sequence | Sequence ID No. |
|---|---|---|---|---|---|
| 101 | CAAAAUU U GUUUGAC | 31 | 267 | AUAAUAU U GUAGUAA | 71 |
| 104 | AAUUUGU U UGACAAU | 32 | 270 | AUAUUGU A GUAAAAU | 72 |
| 105 | AUUUGUU U GACAAUG | 33 | 273 | UUGUAGU A AAAUCCA | 73 |
| 120 | AUGAAGU A GCAUUGU | 34 | 278 | GUAAAAU C CAAUUUC | 74 |
| 125 | GUAGCAU U GUUAAAA | 35 | 283 | AUCCAAU U UCACAAC | 75 |
| 128 | GCAUUGU U AAAAAUA | 36 | 284 | UCCAAUU U CACAACA | 76 |
| 129 | CAUUGUU A AAAAUAA | 37 | 285 | CCAAUUU C ACAACAA | 77 |
| 135 | UAAAAAU A ACAUGCU | 38 | 300 | UGCCAGU A CUACAAA | 78 |
| 143 | ACAUGCU A UACUGAU | 39 | 303 | CAGUACU A CAAAAUG | 79 |
| 145 | AUGCUAU A CUGAUAA | 40 | 316 | UGGAGGU U AUAUAUG | 80 |
| 151 | UACUGAU A AAUUAAU | 41 | 317 | GGAGGUU A UAUAUGG | 81 |
| 155 | GAUAAAU U AAUACAU | 42 | 319 | AGGUUAU A UAUGGGA | 82 |
| 156 | AUAAAUU A AUACAUU | 43 | 321 | GUUAUAU A UGGGAAA | 83 |
| 159 | AAUUAAU A CAUUUAA | 44 | 338 | AUGGAAU U AACACAU | 84 |
| 163 | AAUACAU U UAACUAA | 45 | 339 | UGGAAUU A ACACAUU | 85 |
| 164 | AUACAUU U AACUAAC | 46 | 346 | AACACAU U GCUCUCA | 86 |
| 350 | CAUUGCU C UCAACCU | 87 | | | |
| 352 | UUGCUCU C AACCUAA | 88 | | | |
| 358 | UCAACCU A AUGGUCU | 89 | | | |
| 364 | UAAUGGU C UACUAGA | 90 | | | |
| 366 | AUGGUCU A CUAGAUG | 91 | | | |
| 369 | GUCUACU A GAUGACA | 92 | | | |
| 379 | UGACAAU U GUGAAAU | 93 | | | |
| 387 | GUGAAAU U AAAUUCU | 94 | | | |
| 388 | UGAAAUU A AAUUCUC | 95 | | | |
| 392 | AUUAAAU U CUCCAAA | 96 | | | |
| 393 | UUAAAUU C UCCAAAA | 97 | | | |
| 395 | AAAUUCU C CAAAAAA | 98 | | | |
| 405 | AAAAACU A AGUGAUU | 99 | | | |
| 412 | AAGUGAU U CAACAAU | 100 | | | |
| 413 | AGUGAUU C AACAAUG | 101 | | | |
| 427 | GACCAAU U AUAUGAA | 102 | | | |
| 428 | ACCAAUU A UAUGAAU | 103 | | | |
| 430 | CAAUUAU A UGAAUCA | 104 | | | |
| 436 | UAUGAAU C AAUUAUC | 105 | | | |
| 440 | AAUCAAU U AUCUGAA | 106 | | | |
| 441 | AUCAAUU A UCUGAAU | 107 | | | |
| 443 | CAAUUAU C UGAAUUA | 108 | | | |
| 449 | UCUGAAU U ACUUGGA | 109 | | | |
| 450 | CUGAAUU A CUUGGAU | 110 | | | |
| 453 | AAUUACU U GGAUUUG | 111 | | | |
| 458 | CUUGGAU U UGAUCUU | 112 | | | |
| 459 | UUGGAUU U GAUCUUA | 113 | | | |
| 463 | AUUUGAU C UUAAUCC | 114 | | | |
| 465 | UUGAUCU U AAUCCAU | 115 | | | |
| 466 | UGAUCUU A AUCCAUA | 116 | | | |
| 469 | UCUUAAU C CAUAAAU | 117 | | | |
| 473 | AAUCCAU A AAUUAUA | 118 | | | |
| 477 | CAUAAAU U AUAAUUA | 119 | | | |
| 478 | AUAAAUU A UAAUUAA | 120 | | | |
| 480 | AAAUUAU A AUUAAUA | 121 | | | |
| 483 | UUAUAAU U AAUAUCA | 122 | | | |
| 484 | UAUAAUU A AUAUCAA | 123 | | | |
| 487 | AAUUAAU A UCAACUA | 124 | | | |
| 489 | UUAAUAU C AACUAGC | 125 | | | |
| 494 | AUCAACU A GCAAAUC | 126 | | | |
| 501 | AGCAAAU C AAUGUCA | 127 | | | |
| 507 | UCAAUGU C ACUAACA | 128 | | | |
| 511 | UGUCACU A ACACCAU | 129 | | | |
| 519 | ACACCAU U AGUUAAU | 130 | | | |
| 520 | CACCAUU A GUUAAUA | 131 | | | |
| 523 | CAUUAGU U AAUAUAA | 132 | | | |
| 524 | AUUAGUU A AUAUAAA | 133 | | | |

TABLE III

RSV (1C) HH Ribozyme Sequence

| nt. Position | HH Ribozyme Sequence | Sequence ID No. |
|---|---|---|
| 10 | AAAUUCU CUGAUGAGGCCGAAAGGCCGAA AUUUGCC | 134 |
| 16 | CUUAUCA CUGAUGAGGCCGAAAGGCCGAA AUUCUUA | 135 |
| 17 | ACUUAUC CUGAUGAGGCCGAAAGGCCGAA AAUUCUU | 136 |
| 21 | UGGUACU CUGAUGAGGCCGAAAGGCCGAA AUCAAAU | 137 |
| 25 | UAAGUGG CUGAUGAGGCCGAAAGGCCGAA ACUUAUC | 138 |
| 31 | UAAAUUU CUGAUGAGGCCGAAAGGCCGAA AGUGGUA | 139 |
| 32 | UUAAAUU CUGAUGAGGCCGAAAGGCCGAA AAGUGGU | 140 |
| 36 | GGAGUUA CUGAUGAGGCCGAAAGGCCGAA AUUUAAG | 141 |
| 37 | GGGAGUU CUGAUGAGGCCGAAAGGCCGAA AAUUUAA | 142 |
| 38 | AGGGAGU CUGAUGAGGCCGAAAGGCCGAA AAAUUUA | 143 |
| 42 | ACCAAGG CUGAUGAGGCCGAAAGGCCGAA AGUUAAA | 144 |
| 46 | UCUAACC CUGAUGAGGCCGAAAGGCCGAA AGGGAGU | 145 |
| 50 | CAUCUCU CUGAUGAGGCCGAAAGGCCGAA ACCAAGG | 146 |
| 51 | CCAUCUC CUGAUGAGGCCGAAAGGCCGAA AACCAAG | 147 |
| 67 | CUCAAUG CUGAUGAGGCCGAAAGGCCGAA AUUGCUG | 148 |
| 68 | ACUCAAU CUGAUGAGGCCGAAAGGCCGAA AAUUGCU | 149 |
| 71 | CAUACUC CUGAUGAGGCCGAAAGGCCGAA AUGAAUU | 150 |
| 76 | UUUAUCA CUGAUGAGGCCGAAAGGCCGAA ACUCAAU | 151 |
| 81 | UAACUUU CUGAUGAGGCCGAAAGGCCGAA AUCAUAC | 152 |
| 87 | GUAAUCU CUGAUGAGGCCGAAAGGCCGAA ACUUUA | 153 |
| 88 | UGUAAUC CUGAUGAGGCCGAAAGGCCGAA AACUUUU | 154 |
| 92 | AUUUUGU CUGAUGAGGCCGAAAGGCCGAA AUCUAAC | 155 |
| 93 | AAUUUUG CUGAUGAGGCCGAAAGGCCGAA AAUCUAA | 156 |
| 100 | UCAAACA CUGAUGAGGCCGAAAGGCCGAA AUUUUGU | 157 |
| 101 | GUCAAAC CUGAUGAGGCCGAAAGGCCGAA AAUUUUG | 158 |
| 104 | AUUGUCA CUGAUGAGGCCGAAAGGCCGAA ACAAAUU | 159 |
| 105 | CAUUGUC CUGAUGAGGCCGAAAGGCCGAA AACAAAU | 160 |
| 120 | ACAAUGC CUGAUGAGGCCGAAAGGCCGAA ACUUCAU | 161 |
| 125 | UUUUAAC CUGAUGAGGCCGAAAGGCCGAA AUGCUAC | 162 |
| 128 | UAUUUUU CUGAUGAGGCCGAAAGGCCGAA ACAAUGC | 163 |
| 129 | UUAUUUU CUGAUGAGGCCGAAAGGCCGAA AACAAUG | 164 |
| 135 | AGCAUGU CUGAUGAGGCCGAAAGGCCGAA AUUUUUA | 165 |
| 143 | AUCAGUA CUGAUGAGGCCGAAAGGCCGAA AGCAUGU | 166 |
| 145 | UUAUCAG CUGAUGAGGCCGAAAGGCCGAA AUAGCAU | 167 |
| 151 | AUUAAUU CUGAUGAGGCCGAAAGGCCGAA AUCAGUA | 168 |
| 155 | AUGUAUU CUGAUGAGGCCGAAAGGCCGAA AUUUAUC | 169 |
| 156 | AAUGUAU CUGAUGAGGCCGAAAGGCCGAA AAUUUAU | 170 |
| 159 | UUAAAUG CUGAUGAGGCCGAAAGGCCGAA AUUAAUU | 171 |
| 163 | UUAGUUA CUGAUGAGGCCGAAAGGCCGAA AUGUAUU | 172 |
| 164 | GUUAGUU CUGAUGAGGCCGAAAGGCCGAA AAUGUAU | 173 |
| 165 | CGUUAGU CUGAUGAGGCCGAAAGGCCGAA AAAUGUA | 174 |
| 169 | AAAGCGU CUGAUGAGGCCGAAAGGCCGAA AGUUAAA | 175 |
| 175 | UUAGCCA CUGAUGAGGCCGAAAGGCCGAA AGCGUUA | 176 |
| 176 | CUUAGCC CUGAUGAGGCCGAAAGGCCGAA AAGCGUU | 177 |
| 181 | ACUGCCU CUGAUGAGGCCGAAAGGCCGAA AGCCAAA | 178 |
| 192 | UUGUAUG CUGAUGAGGCCGAAAGGCCGAA AUCACUG | 179 |
| 196 | UUGAUUG CUGAUGAGGCCGAAAGGCCGAA AUGUAUC | 180 |
| 201 | UCAAUUU CUGAUGAGGCCGAAAGGCCGAA AUUGUAU | 181 |
| 206 | GCCAUUC CUGAUGAGGCCGAAAGGCCGAA AUUUGAU | 182 |
| 216 | CAAACAC CUGAUGAGGCCGAAAGGCCGAA AUGCCAU | 183 |
| 221 | AUGCACA CUGAUGAGGCCGAAAGGCCGAA ACACAAU | 184 |
| 222 | CAUGCAC CUGAUGAGGCCGAAAGGCCGAA AACACAA | 185 |
| 231 | UUGUAAU CUGAUGAGGCCGAAAGGCCGAA ACAUGCA | 186 |
| 232 | CUUGUAA CUGAUGAGGCCGAAAGGCCGAA AACAUGC | 187 |
| 234 | UACUUGU CUGAUGAGGCCGAAAGGCCGAA AUAACAU | 188 |
| 235 | CUACUUG CUGAUGAGGCCGAAAGGCCGAA AAUAACA | 189 |
| 241 | AUAUCAC CUGAUGAGGCCGAAAGGCCGAA ACUUGUA | 190 |
| 247 | GGGCAAA CUGAUGAGGCCGAAAGGCCGAA AUCACUA | 191 |
| 249 | UAGGGCA CUGAUGAGGCCGAAAGGCCGAA AUAUCAC | 192 |
| 250 | UUAGGGC CUGAUGAGGCCGAAAGGCCGAA AAUAUCA | 193 |
| 256 | UUAUUAU CUGAUGAGGCCGAAAGGCCGAA AGGGCAA | 194 |
| 259 | AUAUUAU CUGAUGAGGCCGAAAGGCCGAA AUUAGGG | 195 |
| 262 | ACAAUAU CUGAUGAGGCCGAAAGGCCGAA AUUAUUA | 196 |
| 265 | ACUACAA CUGAUGAGGCCGAAAGGCCGAA AUUAUUA | 197 |
| 267 | UUACUAC CUGAUGAGGCCGAAAGGCCGAA AUAUUAU | 198 |
| 270 | AUUUUAC CUGAUGAGGCCGAAAGGCCGAA ACAAUAU | 199 |
| 273 | UGGAUUU CUGAUGAGGCCGAAAGGCCGAA ACUACAA | 200 |
| 278 | GAAAUUG CUGAUGAGGCCGAAAGGCCGAA AUUUUAC | 201 |
| 283 | GUUGUGA CUGAUGAGGCCGAAAGGCCGAA AUUGGAU | 202 |
| 284 | UGUUGUG CUGAUGAGGCCGAAAGGCCGAA AAUUGGA | 203 |
| 285 | UUGUUGU CUGAUGAGGCCGAAAGGCCGAA AAAUUGG | 204 |
| 300 | UUUGUAG CUGAUGAGGCCGAAAGGCCGAA ACUGGCA | 205 |
| 303 | CAUUUUG CUGAUGAGGCCGAAAGGCCGAA AGUACUG | 206 |
| 316 | CAUAUAU CUGAUGAGGCCGAAAGGCCGAA ACCUCCA | 207 |

TABLE III-continued

RSV (1C) HH Ribozyme Sequence

| nt. Position | HH Ribozyme Sequence | Sequence ID No. |
|---|---|---|
| 317 | CCAUAUA CUGAUGAGGCCGAAAGGCCGAA AACCUCC | 208 |
| 319 | UCCCAUA CUGAUGAGGCCGAAAGGCCGAA AUAACCU | 209 |
| 321 | UUUCCCA CUGAUGAGGCCGAAAGGCCGAA AUAUAAC | 210 |
| 338 | AUGUGUU CUGAUGAGGCCGAAAGGCCGAA AUUCCAU | 211 |
| 339 | AAUGUGU CUGAUGAGGCCGAAAGGCCGAA AAUUCCA | 212 |
| 346 | UGAGAGC CUGAUGAGGCCGAAAGGCCGAA AUGUGUU | 213 |
| 350 | AGGUUGA CUGAUGAGGCCGAAAGGCCGAA AGCAAUG | 214 |
| 352 | UUAGGUU CUGAUGAGGCCGAAAGGCCGAA AGAGCAA | 215 |
| 358 | AGACCAU CUGAUGAGGCCGAAAGGCCGAA AGGUUGA | 216 |
| 364 | UCUAGUA CUGAUGAGGCCGAAAGGCCGAA ACCAUUA | 217 |
| 366 | CAUCUAG CUGAUGAGGCCGAAAGGCCGAA AGACCAU | 218 |
| 369 | UGUCAUC CUGAUGAGGCCGAAAGGCCGAA AGUAGAC | 219 |
| 379 | AUUUCAC CUGAUGAGGCCGAAAGGCCGAA AUUGUCA | 220 |
| 387 | AGAAUUU CUGAUGAGGCCGAAAGGCCGAA AUUUCAC | 221 |
| 388 | GAGAAUU CUGAUGAGGCCGAAAGGCCGAA AAUUUCA | 222 |
| 392 | UUUGGAG CUGAUGAGGCCGAAAGGCCGAA AUUUAAU | 223 |
| 393 | UUUUGGA CUGAUGAGGCCGAAAGGCCGAA AAUUUAA | 224 |
| 395 | UUUUUUG CUGAUGAGGCCGAAAGGCCGAA AGAAUUU | 225 |
| 405 | AAUCACU CUGAUGAGGCCGAAAGGCCGAA AGUUUUU | 226 |
| 412 | AUUGUUG CUGAUGAGGCCGAAAGGCCGAA AUCACUU | 227 |
| 413 | CAUUGUU CUGAUGAGGCCGAAAGGCCGAA AAUCACU | 228 |
| 427 | UUCAUAU CUGAUGAGGCCGAAAGGCCGAA AUUGGUC | 229 |
| 428 | AUUCAUA CUGAUGAGGCCGAAAGGCCGAA AAUUGGU | 230 |
| 430 | UGAUUCA CUGAUGAGGCCGAAAGGCCGAA AUAAUUG | 231 |
| 436 | GAUAAUU CUGAUGAGGCCGAAAGGCCGAA AUUCAUA | 232 |
| 440 | UUCAGAU CUGAUGAGGCCGAAAGGCCGAA AUUGAUU | 233 |
| 441 | AUUCAGA CUGAUGAGGCCGAAAGGCCGAA AAUUGAU | 234 |
| 443 | UAAUUCA CUGAUGAGGCCGAAAGGCCGAA AUAAUUG | 235 |
| 449 | UCCAAGU CUGAUGAGGCCGAAAGGCCGAA AUUCAGA | 236 |
| 450 | AUCCAAG CUGAUGAGGCCGAAAGGCCGAA AAUUCAG | 237 |
| 453 | CAAAUCC CUGAUGAGGCCGAAAGGCCGAA AGUAAUU | 238 |
| 458 | AAGAUCA CUGAUGAGGCCGAAAGGCCGAA AUCCAAG | 239 |
| 459 | UAAGAUC CUGAUGAGGCCGAAAGGCCGAA AAUCCAA | 240 |
| 463 | GGAUUAA CUGAUGAGGCCGAAAGGCCGAA AUCAAAU | 241 |
| 465 | AUGGAUU CUGAUGAGGCCGAAAGGCCGAA AGAUCAA | 242 |
| 466 | UAUGGAU CUGAUGAGGCCGAAAGGCCGAA AAGAUCA | 243 |
| 469 | AUUUAUG CUGAUGAGGCCGAAAGGCCGAA AUUAAGA | 244 |
| 473 | UAUAAUU CUGAUGAGGCCGAAAGGCCGAA AUGGAUU | 245 |
| 477 | UAAUUAU CUGAUGAGGCCGAAAGGCCGAA AUUUAUG | 246 |
| 478 | UUAAUUA CUGAUGAGGCCGAAAGGCCGAA AAUUUAU | 247 |
| 480 | UAUUAAU CUGAUGAGGCCGAAAGGCCGAA AUAAUUU | 248 |
| 483 | UGAUAUU CUGAUGAGGCCGAAAGGCCGAA AUUAUAA | 249 |
| 484 | UUGAUAU CUGAUGAGGCCGAAAGGCCGAA AAUUAUA | 250 |
| 487 | UAGUUGA CUGAUGAGGCCGAAAGGCCGAA AUUAAUU | 251 |
| 489 | GCUAGUU CUGAUGAGGCCGAAAGGCCGAA AUAUUAA | 252 |
| 494 | GAUUUGC CUGAUGAGGCCGAAAGGCCGAA AGUUGAU | 253 |
| 501 | UGACAUU CUGAUGAGGCCGAAAGGCCGAA AUUUGCU | 254 |
| 507 | UGUUAGU CUGAUGAGGCCGAAAGGCCGAA ACAUUGA | 255 |
| 511 | AUGGUGU CUGAUGAGGCCGAAAGGCCGAA AGUGACA | 256 |
| 519 | AUUAACU CUGAUGAGGCCGAAAGGCCGAA AUGGUGU | 257 |
| 520 | UAUUAAC CUGAUGAGGCCGAAAGGCCGAA AAUGGUG | 258 |
| 523 | UUAUAUU CUGAUGAGGCCGAAAGGCCGAA ACUAAUG | 259 |
| 524 | UUUAUAU CUGAUGAGGCCGAAAGGCCGAA AACUAAU | 260 |

TABLE IV

RSV (1B) HH Target Sequence

| nt. Position | Target Sequence | Sequence ID No. | nt. Position | Target Sequence | Sequence ID No. |
|---|---|---|---|---|---|
| 10 | GGCAAAU A AAUCAAU | 261 | 276 | AAAAUAU A CUGAAUA | 302 |
| 14 | AAUAAAU C AAUUCAG | 262 | 283 | ACUGAAU A CAACACA | 303 |
| 18 | AAUCAAU U CAGCCAA | 263 | 295 | ACAAAAU A UGGCACU | 304 |
| 19 | AUCAAUU C AGCCAAC | 264 | 303 | UGGCACU U UCCCUAU | 305 |
| 54 | CAAUGAU A AUACACC | 265 | 304 | GGCACUU U CCCUAUG | 306 |
| 57 | UGAUAAU A CACCACA | 266 | 305 | GCACUUU C CCUAUGC | 307 |
| 77 | UGAUGAU C ACAGACA | 267 | 309 | UUUCCCU A UGCCAAU | 308 |
| 94 | AGACCGU U GUCACUU | 268 | 317 | UGCCAAU A UUCAUCA | 309 |
| 97 | CCGUUGU C ACUUGAG | 269 | 319 | CCAAUAU U CAUCAAU | 310 |
| 101 | UGUCACU U GAGACCA | 270 | 320 | CAAUAUU C AUCAAUC | 311 |

TABLE IV-continued

RSV (1B) HH Target Sequence

| nt. Position | Target Sequence | Sequence ID No. | nt. Position | Target Sequence | Sequence ID No. |
|---|---|---|---|---|---|
| 110 | AGACCAU A AUAACAU | 271 | 323 | UAUUCAU C AAUCAUG | 312 |
| 113 | CCAUAAU A ACAUCAC | 272 | 327 | CAUCAAU C AUGAUGG | 313 |
| 118 | AUAACAU C ACUAACC | 273 | 337 | GAUGGGU U CUUAGAA | 314 |
| 122 | CAUCACU A ACCAGAG | 274 | 338 | AUGGGUU C UUAGAAU | 315 |
| 134 | GAGACAU C AUAACAC | 275 | 340 | GGGUUCU U AGAAUGC | 316 |
| 137 | ACAUCAU A ACACACA | 276 | 341 | GGUUCUU A GAAUGCA | 317 |
| 148 | CACAAAU U UAUAUAC | 277 | 350 | AAUGCAU U GGCAUUA | 318 |
| 149 | ACAAAUU U AUAUACU | 278 | 356 | UUGGCAU U AAGCCUA | 319 |
| 150 | CAAAUUU A UAUACUU | 279 | 357 | UGGCAUU A AGCCUAC | 320 |
| 152 | AAUUUAU A UACUUGA | 280 | 363 | UAAGCCU A CAAAGCA | 321 |
| 154 | UUUAUAU A CUUGAUA | 281 | 372 | AAAGCAU A CUCCCAU | 322 |
| 157 | AUAUACU U GAUAAAU | 282 | 375 | GCAUACU C CCAUAAU | 323 |
| 161 | ACUUGAU A AAUCAUG | 283 | 380 | CUCCCAU A AUAUACA | 324 |
| 165 | GAUAAAU C AUGAAUG | 284 | 383 | CCAUAAU A UACAAGU | 325 |
| 176 | AAUGCAU A GUGAGAA | 285 | 385 | AUAAUAU A CAAGUAU | 326 |
| 188 | GAAAACU U GAUGAAA | 286 | 391 | UACAAGU A UGAUCUC | 327 |
| 208 | GCCACAU U UACAUUC | 287 | 396 | GUAUGAU C UCAAUCC | 328 |
| 209 | CCACAUU U ACAUUCC | 288 | 398 | AUGAUCU C AAUCCAU | 329 |
| 210 | CACAUUU A CAUUCCU | 289 | 402 | UCUCAAU C CAUAAAU | 330 |
| 214 | UUUACAU U CCUGGUC | 290 | 406 | AAUCCAU A AAUUUCA | 331 |
| 215 | UUACAUU C CUGGUCA | 291 | 410 | CAUAAAU U UCAACAC | 332 |
| 221 | UCCUGGU C AACUAUG | 292 | 411 | AUAAAUU U CAACACA | 333 |
| 226 | GUCAACU A UGAAAUG | 293 | 412 | UAAAUUU C AACACAA | 334 |
| 239 | UGAAACU A UUACACA | 294 | 421 | ACACAAU A UUCACAC | 335 |
| 241 | AAACUAU U ACACAAA | 295 | 423 | ACAAUAU U CACACAA | 336 |
| 242 | AACUAUU A CACAAAG | 296 | 424 | CAAUAUU C ACACAAU | 337 |
| 251 | ACAAAGU A GGAAGCA | 297 | 432 | ACACAAU C UAAAACA | 338 |
| 261 | AAGCACU A AAUAUAA | 298 | 434 | ACAAUCU A AAACAAC | 339 |
| 265 | ACUAAAU A UAAAAAA | 299 | 446 | AACAACU C UAUGCAU | 340 |
| 267 | UAAAUAU A AAAAAUA | 300 | 448 | CAACUCU A UGCAUAA | 341 |
| 274 | AAAAAAU A UACUGAA | 301 | 454 | UAUGCAU A ACUAUAC | 342 |
| 458 | CAUAACU A UACUCCA | 343 | | | |
| 460 | UAACUAU A CUCCAUA | 344 | | | |
| 463 | CUAUACU C CAUAGUC | 345 | | | |
| 467 | ACUCCAU A GUCCAGA | 346 | | | |
| 470 | CCAUAGU C CAGAUGG | 347 | | | |
| 489 | UGAAAAU U AUAGUAA | 348 | | | |
| 490 | GAAAAUU A UAGUAAU | 349 | | | |
| 492 | AAAUUAU A GUAAUUU | 350 | | | |
| 495 | UUAUAGU A AUUUAAA | 351 | | | |

TABLE V

RSV (1B) HH Ribozyme Sequence

| nt. Position | HH Ribozyme Sequence | Sequence ID No. |
|---|---|---|
| 10 | AUUGAUU CUGAUGAGGCCGAAAGGCCGAA AUUUGCC | 352 |
| 14 | CUGAAUU CUGAUGAGGCCGAAAGGCCGAA AUUUAUU | 353 |
| 18 | UUGGCUG CUGAUGAGGCCGAAAGGCCGAA AUUGAUU | 354 |
| 19 | GUUGGCU CUGAUGAGGCCGAAAGGCCGAA AAUUGAU | 355 |
| 54 | GGUGUAU CUGAUGAGGCCGAAAGGCCGAA AUCAUUG | 356 |
| 57 | UGUGGUG CUGAUGAGGCCGAAAGGCCGAA AUUAUCA | 357 |
| 77 | UGUCUGU CUGAUGAGGCCGAAAGGCCGAA AUCAUCA | 358 |
| 94 | AAGUGAC CUGAUGAGGCCGAAAGGCCGAA ACGGUCU | 359 |
| 97 | CUCAAGU CUGAUGAGGCCGAAAGGCCGAA ACAACGG | 360 |
| 101 | UGGUCUC CUGAUGAGGCCGAAAGGCCGAA AGUGACA | 361 |
| 110 | AUGUUAU CUGAUGAGGCCGAAAGGCCGAA AUGGUCU | 362 |
| 113 | GUGAUGU CUGAUGAGGCCGAAAGGCCGAA AUUAUGG | 363 |
| 118 | GGUUAGU CUGAUGAGGCCGAAAGGCCGAA AUGUUAU | 364 |
| 122 | CUCUGGU CUGAUGAGGCCGAAAGGCCGAA AGUGAUG | 365 |
| 134 | GUGUUAU CUGAUGAGGCCGAAAGGCCGAA AUGUCUC | 366 |
| 137 | UGUGUGU CUGAUGAGGCCGAAAGGCCGAA AUGAUGU | 367 |
| 148 | GUAUAUA CUGAUGAGGCCGAAAGGCCGAA AUUUGUG | 368 |
| 149 | AGUAUAU CUGAUGAGGCCGAAAGGCCGAA AAUUUGU | 369 |
| 150 | AAGUAUA CUGAUGAGGCCGAAAGGCCGAA AAAUUUG | 370 |
| 152 | UCAAGUA CUGAUGAGGCCGAAAGGCCGAA AUAAAUU | 371 |
| 154 | UAUCAAG CUGAUGAGGCCGAAAGGCCGAA AUAUAAA | 372 |
| 157 | AUUUAUC CUGAUGAGGCCGAAAGGCCGAA AGUAUAU | 373 |
| 161 | CAUGAUU CUGAUGAGGCCGAAAGGCCGAA AUCAAGU | 374 |

TABLE V-continued

RSV (1B) HH Ribozyme Sequence

| nt. Position | HH Ribozyme Sequence | Sequence ID No. |
|---|---|---|
| 165 | CAUUCAU CUGAUGAGGCCGAAAGGCCGAA AUUUAUC | 375 |
| 176 | UUCUCAC CUGAUGAGGCCGAAAGGCCGAA AUGCAUU | 376 |
| 188 | UUUCAUC CUGAUGAGGCCGAAAGGCCGAA AGUUUUC | 377 |
| 208 | GAAUGUA CUGAUGAGGCCGAAAGGCCGAA AUGUGGC | 378 |
| 209 | GGAAUGU CUGAUGAGGCCGAAAGGCCGAA AAUGUGG | 379 |
| 210 | AGGAAUG CUGAUGAGGCCGAAAGGCCGAA AAAUGUG | 380 |
| 214 | GACCAGG CUGAUGAGGCCGAAAGGCCGAA AUGUAAA | 381 |
| 215 | UGACCAG CUGAUGAGGCCGAAAGGCCGAA AAUGUAA | 382 |
| 221 | CAUAGUU CUGAUGAGGCCGAAAGGCCGAA ACCAGGA | 383 |
| 226 | CAUUUCA CUGAUGAGGCCGAAAGGCCGAA AGUUGAC | 384 |
| 239 | UGUGUAA CUGAUGAGGCCGAAAGGCCGAA AGUUUCA | 385 |
| 241 | UUUGUGU CUGAUGAGGCCGAAAGGCCGAA AUAGUUU | 386 |
| 242 | CUUUGUG CUGAUGAGGCCGAAAGGCCGAA AAUAGUU | 387 |
| 251 | UGCUUCC CUGAUGAGGCCGAAAGGCCGAA ACUUUGU | 388 |
| 261 | UUAUAUU CUGAUGAGGCCGAAAGGCCGAA AGUGCUU | 389 |
| 265 | UUUUUUA CUGAUGAGGCCGAAAGGCCGAA AUUUAGU | 390 |
| 267 | UAUUUUU CUGAUGAGGCCGAAAGGCCGAA AUAUUUA | 391 |
| 274 | UUCAGUA CUGAUGAGGCCGAAAGGCCGAA AUUUUUU | 392 |
| 276 | UAUUCAG CUGAUGAGGCCGAAAGGCCGAA AUAUUUU | 393 |
| 283 | UGUGUUG CUGAUGAGGCCGAAAGGCCGAA AUUCAGU | 394 |
| 295 | AGUGCCA CUGAUGAGGCCGAAAGGCCGAA AUUUUGU | 395 |
| 303 | AUAGGGA CUGAUGAGGCCGAAAGGCCGAA AGUGCCA | 396 |
| 304 | CAUAGGG CUGAUGAGGCCGAAAGGCCGAA AAGUGCC | 397 |
| 305 | GCAUAGG CUGAUGAGGCCGAAAGGCCGAA AAAGUGC | 398 |
| 309 | AUUGGCA CUGAUGAGGCCGAAAGGCCGAA AGGGAAA | 399 |
| 317 | UGAUGAA CUGAUGAGGCCGAAAGGCCGAA AUUGGCA | 400 |
| 319 | AUUGAUG CUGAUGAGGCCGAAAGGCCGAA AUAUUGG | 401 |
| 320 | GAUUGAU CUGAUGAGGCCGAAAGGCCGAA AAUAUUG | 402 |
| 323 | CAUGAUU CUGAUGAGGCCGAAAGGCCGAA AUGAAUA | 403 |
| 327 | CCAUCAU CUGAUGAGGCCGAAAGGCCGAA AUUGAUG | 404 |
| 337 | UUCUAAG CUGAUGAGGCCGAAAGGCCGAA ACCCAUC | 405 |
| 338 | AUUCUAA CUGAUGAGGCCGAAAGGCCGAA AACCCAU | 406 |
| 340 | GCAUUCU CUGAUGAGGCCGAAAGGCCGAA AGAACCC | 407 |
| 341 | UGCAUUC CUGAUGAGGCCGAAAGGCCGAA AAGAACC | 408 |
| 350 | UAAUGCC CUGAUGAGGCCGAAAGGCCGAA AUGCAUU | 409 |
| 356 | UAGGCUU CUGAUGAGGCCGAAAGGCCGAA AUGCCAA | 410 |
| 357 | GUAGGCU CUGAUGAGGCCGAAAGGCCGAA AAUGCCA | 411 |
| 363 | UGCUUUG CUGAUGAGGCCGAAAGGCCGAA AGGCUUA | 412 |
| 372 | AUGGGAG CUGAUGAGGCCGAAAGGCCGAA AUGCUUU | 413 |
| 375 | AUUAUGG CUGAUGAGGCCGAAAGGCCGAA AGUAUGC | 414 |
| 380 | UGUAUAU CUGAUGAGGCCGAAAGGCCGAA AUGGGAG | 415 |
| 383 | ACUUGUA CUGAUGAGGCCGAAAGGCCGAA AUUAUGG | 416 |
| 385 | AUACUUG CUGAUGAGGCCGAAAGGCCGAA AUAUUAU | 417 |
| 391 | GAGAUCA CUGAUGAGGCCGAAAGGCCGAA ACUUGUA | 418 |
| 396 | GGAUUGA CUGAUGAGGCCGAAAGGCCGAA AUCAUAC | 419 |
| 398 | AUGGAUU CUGAUGAGGCCGAAAGGCCGAA AGAUCAU | 420 |
| 402 | AUUUAUG CUGAUGAGGCCGAAAGGCCGAA AUUGAGA | 421 |
| 406 | UGAAAUU CUGAUGAGGCCGAAAGGCCGAA AUGGAUU | 422 |
| 410 | GUGUUGA CUGAUGAGGCCGAAAGGCCGAA AUUUAUG | 423 |
| 411 | UGUGUUG CUGAUGAGGCCGAAAGGCCGAA AAUUUAU | 424 |
| 412 | UUGUGUU CUGAUGAGGCCGAAAGGCCGAA AAAUUUA | 425 |
| 421 | GUGUGAA CUGAUGAGGCCGAAAGGCCGAA AUUGUGU | 426 |
| 423 | UUGUGUG CUGAUGAGGCCGAAAGGCCGAA AUAUUGU | 427 |
| 424 | AUUGUGU CUGAUGAGGCCGAAAGGCCGAA AAUAUUG | 428 |
| 432 | UGUUUUA CUGAUGAGGCCGAAAGGCCGAA AUUGUGU | 429 |
| 434 | GUUGUUU CUGAUGAGGCCGAAAGGCCGAA AGAUUGU | 430 |
| 446 | AUGCAUA CUGAUGAGGCCGAAAGGCCGAA AGUUGUU | 431 |
| 448 | UUAUGCA CUGAUGAGGCCGAAAGGCCGAA AGAGUUG | 432 |
| 454 | GUAUAGU CUGAUGAGGCCGAAAGGCCGAA AUGCAUA | 433 |
| 458 | UGGAGUA CUGAUGAGGCCGAAAGGCCGAA AGUUAUG | 434 |
| 460 | UAUGGAG CUGAUGAGGCCGAAAGGCCGAA AUAGUUA | 435 |
| 463 | GACUAUG CUGAUGAGGCCGAAAGGCCGAA AGUAUAG | 436 |
| 467 | UCUGGAC CUGAUGAGGCCGAAAGGCCGAA AUGGAGU | 437 |
| 470 | CCAUCUG CUGAUGAGGCCGAAAGGCCGAA ACUAUGG | 438 |
| 489 | UUACUAU CUGAUGAGGCCGAAAGGCCGAA AUUUUCA | 439 |
| 490 | AUUACUA CUGAUGAGGCCGAAAGGCCGAA AAUUUUC | 440 |
| 492 | AAAUUAC CUGAUGAGGCCGAAAGGCCGAA AUAAUUU | 441 |
| 495 | UUUAAAU CUGAUGAGGCCGAAAGGCCGAA ACUAUAA | 442 |

TABLE VI

RSV (N) HH Target Sequence

| nt. Position | Target Sequence | Sequence ID No. | nt. Position | Target Sequence | Sequence ID No. |
|---|---|---|---|---|---|
| 9 | GGCAAAU A CAAAGAU | 443 | 217 | GGUAUGU U AUAUGCG | 484 |
| 21 | GAUGGCU C UUAGCAA | 444 | 218 | GUAUGUU A UAUGCGA | 485 |
| 23 | UGGCUCU U AGCAAAG | 445 | 220 | AUGUUAU A UGCGAUG | 486 |
| 24 | GGCUCUU A GCAAAGU | 446 | 229 | GCGAUGU C UAGGUUA | 487 |
| 32 | GCAAAGU C AAGUUGA | 447 | 231 | GAUGUCU A GGUUAGG | 488 |
| 37 | GUCAAGU U GAAUGAU | 448 | 235 | UCUAGGU U AGGAAGA | 489 |
| 45 | GAAUGAU A CACUCAA | 449 | 236 | CUAGGUU A GGAAGAG | 490 |
| 50 | AUACACU C AACAAAG | 450 | 254 | ACACCAU A AAAAUAC | 491 |
| 60 | CAAAGAU C AACUUCU | 451 | 260 | UAAAAAU A CUCAGAG | 492 |
| 65 | AUCAACU U CUGUCAU | 452 | 263 | AAAUACU C AGAGAUG | 493 |
| 66 | UCAACUU C UGUCAUC | 453 | 277 | GCGGGAU A UCAUGUA | 494 |
| 70 | CUUCUGU C AUCCAGC | 454 | 279 | GGGAUAU C AUGUAAA | 495 |
| 73 | CUGUCAU C CAGCAAA | 455 | 284 | AUCAUGU A AAAGCAA | 496 |
| 82 | AGCAAAU A CACCAUC | 456 | 299 | AUGGAGU A GAUGUAA | 497 |
| 89 | ACACCAU C CAACGGA | 457 | 305 | UAGAUGU A ACAACAC | 498 |
| 108 | AGGAGAU A GUAUUGA | 458 | 315 | AACACAU C GUCAAGA | 499 |
| 111 | AGAUAGU A UUGAUAC | 459 | 318 | ACAUCGU C AAGACAU | 500 |
| 113 | AUAGUAU U GAUACUC | 460 | 326 | AAGACAU U AAUGGAA | 501 |
| 117 | UAUUGAU A CUCCUAA | 461 | 327 | AGACAUU A AUGGAAA | 502 |
| 120 | UGAUACU C CUAAUUA | 462 | 346 | AUGAAAU U UGAAGUG | 503 |
| 123 | UACUCCU A AUUAUGA | 463 | 347 | UGAAAUU U GAAGUGU | 504 |
| 126 | UCCUAAU U AUGAUGU | 464 | 355 | GAAGUGU U AACAUUG | 505 |
| 127 | CCUAAUU A UGAUGUG | 465 | 356 | AAGUGUU A ACAUUGG | 506 |
| 146 | AACACAU C AAUAAGU | 466 | 361 | UUAACAU U GGCAAGC | 507 |
| 150 | CAUCAAU A AGUUAUG | 467 | 370 | GCAAGCU U AACAACU | 508 |
| 154 | AAUAAGU U AUGUGGC | 468 | 371 | CAAGCUU A ACAACUG | 509 |
| 155 | AUAAGUU A UGUGGCA | 469 | 383 | CUGAAAU U CAAAUCA | 510 |
| 166 | GGCAUGU U AUUAAUC | 470 | 384 | UGAAAUU C AAAUCAA | 511 |
| 167 | GCAUGUU A UUAAUCA | 471 | 389 | UUCAAAU C AACAUUG | 512 |
| 169 | AUGUUAU U AAUCACA | 472 | 395 | UCAACAU U GAGAUAG | 513 |
| 170 | UGUUAUU A AUCACAG | 473 | 401 | UUGAGAU A GAAUCUA | 514 |
| 173 | UAUUAAU C ACAGAAG | 474 | 406 | AUAGAAU C UAGAAAA | 515 |
| 186 | AGAUGCU A AUCAUAA | 475 | 408 | AGAAUCU A GAAAAUC | 516 |
| 189 | UGCUAAU C AUAAAUU | 476 | 415 | AGAAAAU C CUACAAA | 517 |
| 192 | UAAUCAU A AAUUCAC | 477 | 418 | AAAUCCU A CAAAAAA | 518 |
| 196 | CAUAAAU U CACUGGG | 478 | 431 | AAAUGCU A AAAGAAA | 519 |
| 197 | AUAAAUU C ACUGGGU | 479 | 449 | GAGAGGU A GCUCCAG | 520 |
| 205 | ACUGGGU U AAUAGGU | 480 | 453 | GGUAGCU C CAGAAUA | 521 |
| 206 | CUGGGUU A AUAGGUA | 481 | 460 | CCAGAAU A CAGGCAU | 522 |
| 209 | GGUUAAU A GGUAUGU | 482 | 472 | CAUGACU C UCCUGAU | 523 |
| 213 | AAUAGGU A UGUUAUA | 483 | 474 | UGACUCU C CUGAUUG | 524 |
| 480 | UCCUGAU U GUGGGAU | 525 | 696 | UUUUGGU A UAGCACA | 574 |
| 491 | GGAUGAU A AUAUUAU | 526 | 698 | UUGGUAU A GCACAAU | 575 |
| 494 | UGAUAAU A UUAUGUA | 527 | 706 | GCACAAU C UUCUACC | 576 |
| 496 | AUAAUAU U AUGUAUA | 528 | 708 | ACAAUCU U CUACCAG | 577 |
| 497 | UAAUAUU A UGUAUAG | 529 | 709 | CAAUCUU C UACCAGA | 578 |
| 501 | AUUAUGU A UAGCAGC | 530 | 711 | AUCUUCU A CCAGAGG | 579 |
| 503 | UAUGUAU A GCAGCAU | 531 | 726 | UGGCAGU A GAGUUGA | 580 |
| 511 | GCAGCAU U AGUAAUA | 532 | 731 | GUAGAGU U GAAGGGA | 581 |
| 512 | CAGCAUU A GUAAUAA | 533 | 740 | AAGGGAU U UUUGCAG | 582 |
| 515 | CAUUAGU A AUAACUA | 534 | 741 | AGGGAUU U UUGCAGG | 583 |
| 518 | UAGUAAU A ACUAAAU | 535 | 742 | GGGAUUU U UGCAGGA | 584 |
| 522 | AAUAACU A AAUUAGC | 536 | 743 | GGAUUUU U GCAGGAU | 585 |
| 526 | ACUAAAU U AGCAGCA | 537 | 751 | GCAGGAU U GUUUAUG | 586 |
| 527 | CUAAAUU A GCAGCAG | 538 | 754 | GGAUUGU U UAUGAAU | 587 |
| 544 | GACAGAU C UGGUCUU | 539 | 755 | GAUUGUU U AUGAAUG | 588 |
| 549 | AUCUGGU C UUACAGC | 540 | 756 | AUUGUUU A UGAAUGC | 589 |
| 551 | CUGGUCU U ACAGCCG | 541 | 766 | AAUGCCU A UGGUGCA | 590 |
| 552 | UGGUCUU A CAGCCGU | 542 | 787 | GUGAUGU U ACGGUGG | 591 |
| 563 | CCGUGAU U AGGAGAG | 543 | 788 | UGAUGUU A CGGUGGG | 592 |
| 564 | CGUGAUU A GGAGAGC | 544 | 800 | GGGGAGU C UUAGCAA | 593 |
| 573 | GAGAGCU A AUAAUGU | 545 | 802 | GGAGUCU U AGCAAAA | 594 |
| 576 | AGCUAAU A AUGUCCU | 546 | 803 | GAGUCUU A GCAAAAU | 595 |
| 581 | AUAAUGU C CUAAAAA | 547 | 811 | GCAAAAU C AGUUAAA | 596 |
| 584 | AUGUCCU A AAAAAUG | 548 | 815 | AAUCAGU U AAAAAUA | 597 |
| 603 | GAAACGU U ACAAAGG | 549 | 816 | AUCAGUU A AAAAUAU | 598 |
| 604 | AAACGUU A CAAAGGC | 550 | 822 | UAAAAAU A UUAUGUU | 599 |
| 613 | AAAGGCU U ACUACCC | 551 | 824 | AAAAUAU U AUGUUAG | 600 |
| 614 | AAGGCUU A CUACCCA | 552 | 825 | AAAUAUU A UGUUAGG | 601 |
| 617 | GCUUACU A CCCAAGG | 553 | 829 | AUUAUGU U AGGACAU | 602 |
| 629 | AGGACAU A GCCAACA | 554 | 830 | UUAUGUU A GGACAUG | 603 |
| 640 | AACAGCU U CUAUGAA | 555 | 840 | ACAUGCU A GUGUGCA | 604 |
| 641 | ACAGCUU C UAUGAAG | 556 | 866 | AACAAGU U GUUGAGG | 605 |
| 643 | AGCUUCU A UGAAGUG | 557 | 869 | AAGUUGU U GAGGUUU | 606 |

TABLE VI-continued

RSV (N) HH Target Sequence

| nt. Position | Target Sequence | Sequence ID No. | nt. Position | Target Sequence | Sequence ID No. |
|---|---|---|---|---|---|
| 652 | GAAGUGU U UGAAAAA | 558 | 875 | UUGAGGU U UAUGAAU | 607 |
| 653 | AAGUGUU U GAAAAAC | 559 | 876 | UGAGGUU U AUGAAUA | 608 |
| 663 | AAAACAU C CCCACUU | 560 | 877 | GAGGUUU A UGAAUAU | 609 |
| 670 | CCCCACU U UAUAGAU | 561 | 883 | UAUGAAU A UGCCCAA | 610 |
| 671 | CCCACUU U AUAGAUG | 562 | 895 | CAAAAAU U GGGUGGU | 611 |
| 672 | CCACUUU A UAGAUGU | 563 | 913 | GCAGGAU U CUACCAU | 612 |
| 674 | ACUUUAU A GAUGUUU | 564 | 914 | CAGGAUU C UACCAUA | 613 |
| 680 | UAGAUGU U UUUGUUC | 565 | 916 | GGAUUCU A CCAUAUA | 614 |
| 681 | AGAUGUU U UUGUUCA | 566 | 921 | CUACCAU A UAUUGAA | 615 |
| 682 | GAUGUUU U UGUUCAU | 567 | 923 | ACCAUAU A UUGAACA | 616 |
| 683 | AUGUUUU U GUUCAUU | 568 | 925 | CAUAUAU U GAACAAC | 617 |
| 686 | UUUUUGU U CAUUUUG | 569 | 943 | AAAGCAU C AUUAUUA | 618 |
| 687 | UUUUGUU C AUUUUGG | 570 | 946 | GCAUCAU U AUUAUCU | 619 |
| 690 | UGUUCAU U UUGGUAU | 571 | 947 | CAUCAUU A UUAUCUU | 620 |
| 691 | GUUCAUU U UGGUAUA | 572 | 949 | UCAUUAU U AUCUUUG | 621 |
| 692 | UUCAUUU U GGUAUAG | 573 | 950 | CAUUAUU A UCUUUGA | 622 |
| 952 | UUAUUAU C UUUGACU | 623 | | | |
| 954 | AUUAUCU U UGACUCA | 624 | | | |
| 955 | UUAUCUU U GACUCAA | 625 | | | |
| 960 | UUUGACU C AAUUUCC | 626 | | | |
| 964 | ACUCAAU U UCCUCAC | 627 | | | |
| 965 | CUCAAUU U CCUCACU | 628 | | | |
| 966 | UCAAUUU C CUCACUU | 629 | | | |
| 969 | AUUUCCU C ACUUCUC | 630 | | | |
| 973 | CCUCACU U CUCCAGU | 631 | | | |
| 974 | CUCACUU C UCCAGUG | 632 | | | |
| 976 | CACUUCU C CAGUGUA | 633 | | | |
| 983 | CCAGUGU A GUAUUAG | 634 | | | |
| 986 | GUGUAGU A UUAGGCA | 635 | | | |
| 988 | GUAGUAU U AGGCAAU | 636 | | | |
| 989 | UAGUAUU A GGCAAUG | 637 | | | |
| 1007 | CUGGCCU A GGCAUAA | 638 | | | |
| 1013 | UAGGCAU A AUGGGAG | 639 | | | |
| 1024 | GGAGAGU A CAGAGGU | 640 | | | |
| 1032 | CAGAGGU A CACCGAG | 641 | | | |
| 1044 | GAGGAAU C AAGAUCU | 642 | | | |
| 1050 | UCAAGAU C UAUAUGA | 643 | | | |
| 1052 | AAGAUCU A UAUGAUG | 644 | | | |
| 1054 | GAUCUAU A UGAUGCA | 645 | | | |
| 1072 | AAGGCAU A UGCUGAA | 646 | | | |
| 1085 | AACAACU C AAAGAAA | 647 | | | |
| 1103 | GUGUGAU U AACUACA | 648 | | | |
| 1104 | UGUGAUU A ACUACAG | 649 | | | |
| 1108 | AUUAACU A CAGUGUA | 650 | | | |
| 1115 | ACAGUGU A CUAGACU | 651 | | | |
| 1118 | GUGUACU A GACUUGA | 652 | | | |
| 1123 | CUAGACU U GACAGCA | 653 | | | |
| 1139 | AAGAACU A GAGGCUA | 654 | | | |
| 1146 | AGAGGCU A UCAAACA | 655 | | | |
| 1148 | AGGCUAU C AAACAUC | 656 | | | |
| 1155 | CAAACAU C AGCUUAA | 657 | | | |
| 1160 | AUCAGCU U AAUCCAA | 658 | | | |
| 1161 | UCAGCUU A AUCCAAA | 659 | | | |
| 1164 | GCUUAAU C CAAAAGA | 660 | | | |
| 1173 | AAAAGAU A AUGAUGU | 661 | | | |
| 1181 | AUGAUGU A GAGCUUU | 662 | | | |
| 1187 | UAGAGCU U UGAGUUA | 663 | | | |
| 1188 | AGAGCUU U GAGUUAA | 664 | | | |
| 1193 | UUUGAGU U AAUAAAA | 665 | | | |
| 1194 | UUGAGUU A AUAAAAA | 666 | | | |

TABLE VIII

RSV (1B) HP Ribozyme/Substrate Sequence

| nt. Position | HP Ribozyme Sequence | Sequence ID No. |
|---|---|---|
| 70 | CUGUGAUC AGAA GUCUUU ACCAGAGAAACACACGUUGUGGUACAUUACCUGGUA | 891 |
| 91 | CAAGUGAC AGAA GUCUCA ACCAGAGAAACACACGUUGUGGUACAUUACCUGGUA | 892 |
| 472 | CAGGCUCC AGAA GGACUA ACCAGAGAAACACACGUUGUGGUACAUUACCUGGUA | 893 |

TABLE VIII-continued

RSV (1B) HP Ribozyme/Substrate Sequence

| nt. Position | Substrate | Sequence ID No. |
|---|---|---|
| 70 | AAAGACU GAU GAUCACAG | 894 |
| 91 | UGAGACC GUU GUCACUUG | 895 |
| 472 | UAGUCCA GAU GGAGCCUG | 896 |

TABLE IX

RSV (N) HP Ribozyme/Substrate Sequence

| nt. Position | HP Ribozyme Sequence | Sequence ID No. |
|---|---|---|
| 476 | AUCCCACA AGAA GGAGAG ACCAGAGAAACACACGUUGUGGUACAUUACCUGGUA | 897 |
| 540 | AAGACCAG AGAA GUCCCC ACCAGAGAAACACACGUUGUGGUACAUUACCUGGUA | 898 |
| 554 | CUAAUCAC AGAA GUAAGA ACCAGAGAAACACACGUUGUGGUACAUUACCUGGUA | 899 |
| 636 | UUCAUAGA AGAA GUUGGC ACCAGAGAAACACACGUUGUGGUACAUUACCUGGUA | 900 |
| 998 | CCUAGGCC AGAA GCAUUG ACCAGAGAAACACACGUUGUGGUACAUUACCUGGUA | 901 |
| 1156 | UUGGAUUA AGAA GAUGUU ACCAGAGAAACACACGUUGUGGUACAUUACCUGGUA | 902 |

| nt. Position | Substrate | Sequence ID No. |
|---|---|---|
| 476 | CUCUCCU GAU UGUGGGAU | 903 |
| 540 | GGGGACA GAU CUGGUCUU | 904 |
| 554 | UCUUACA GCC GUGAUUAG | 905 |
| 636 | GCCAACA GCU UCUAUGAA | 906 |
| 998 | CAAUGCU GCU GGCCUAGG | 907 |
| 1156 | AACAUCA GCU UAAUCCAA | 908 |

TABLE VII

RSV (N) HH Ribozyme Sequence

| nt. Position | HH Ribozyme Sequence | Sequence ID No. |
|---|---|---|
| 9 | AUCUUUG CUGAUGAGGCCGAAAGGCCGAA AUUUGCC | 667 |
| 21 | UUGCUAA CUGAUGAGGCCGAAAGGCCGAA AGCCAUC | 668 |
| 23 | CUUUGCU CUGAUGAGGCCGAAAGGCCGAA AGAGCCA | 669 |
| 24 | ACUUUGC CUGAUGAGGCCGAAAGGCCGAA AAGAGCC | 670 |
| 32 | UCAACUU CUGAUGAGGCCGAAAGGCCGAA ACUUUGC | 671 |
| 37 | AUCAUUC CUGAUGAGGCCGAAAGGCCGAA ACUUGAC | 672 |
| 45 | UUGAGUG CUGAUGAGGCCGAAAGGCCGAA AUCAUUC | 673 |
| 50 | CUUUGUU CUGAUGAGGCCGAAAGGCCGAA AGUGUAU | 674 |
| 60 | AGAAGUU CUGAUGAGGCCGAAAGGCCGAA AUCUUUG | 675 |
| 65 | AUGACAG CUGAUGAGGCCGAAAGGCCGAA AGUUGAU | 676 |
| 66 | GAUGACA CUGAUGAGGCCGAAAGGCCGAA AAGUUGA | 677 |
| 70 | GCUGGAU CUGAUGAGGCCGAAAGGCCGAA ACAGAAG | 678 |
| 73 | UUUGCUG CUGAUGAGGCCGAAAGGCCGAA AUGACAG | 679 |
| 82 | GAUGGUG CUGAUGAGGCCGAAAGGCCGAA AUUUGCU | 680 |
| 89 | UCCGUUG CUGAUGAGGCCGAAAGGCCGAA AUGGUGU | 681 |
| 108 | UCAAUAC CUGAUGAGGCCGAAAGGCCGAA AUCUCCU | 682 |
| 111 | GUAUCAA CUGAUGAGGCCGAAAGGCCGAA ACUAUCU | 683 |
| 113 | GAGUAUC CUGAUGAGGCCGAAAGGCCGAA AUACUAU | 684 |
| 117 | UUAGGAG CUGAUGAGGCCGAAAGGCCGAA AUCAAUA | 685 |
| 120 | UAAUUAG CUGAUGAGGCCGAAAGGCCGAA AGUAUCA | 686 |
| 123 | UCAUAAU CUGAUGAGGCCGAAAGGCCGAA AGGAGUA | 687 |
| 126 | ACAUCAU CUGAUGAGGCCGAAAGGCCGAA AUUAGGA | 688 |
| 127 | CACAUCA CUGAUGAGGCCGAAAGGCCGAA AAUUAGG | 689 |
| 146 | ACUUAUU CUGAUGAGGCCGAAAGGCCGAA AUGUGUU | 690 |
| 150 | CAUAACU CUGAUGAGGCCGAAAGGCCGAA AUUGAUG | 691 |
| 154 | GCCACAU CUGAUGAGGCCGAAAGGCCGAA ACUUAUU | 692 |
| 155 | UGCCACA CUGAUGAGGCCGAAAGGCCGAA AACUUAU | 693 |
| 166 | GAUUAAU CUGAUGAGGCCGAAAGGCCGAA ACAUGCC | 694 |
| 167 | UGAUUAA CUGAUGAGGCCGAAAGGCCGAA AACAUGC | 695 |
| 169 | UGUGAUU CUGAUGAGGCCGAAAGGCCGAA AUAACAU | 696 |
| 170 | CUGUGAU CUGAUGAGGCCGAAAGGCCGAA AAUAACA | 697 |
| 173 | CUUCUGU CUGAUGAGGCCGAAAGGCCGAA AUUAAUA | 698 |

TABLE VII-continued

RSV (N) HH Ribozyme Sequence

| nt. Position | HH Ribozyme Sequence | Sequence ID No. |
|---|---|---|
| 186 | UUAUGAU CUGAUGAGGCCGAAAGGCCGAA AGCAUCU | 699 |
| 189 | AAUUUAU CUGAUGAGGCCGAAAGGCCGAA AUUAGCA | 700 |
| 192 | GUGAAUU CUGAUGAGGCCGAAAGGCCGAA AUGAUUA | 701 |
| 196 | CCCAGUG CUGAUGAGGCCGAAAGGCCGAA AUUUAUG | 702 |
| 197 | ACCCAGU CUGAUGAGGCCGAAAGGCCGAA AAUUUAU | 703 |
| 205 | ACCUAUU CUGAUGAGGCCGAAAGGCCGAA ACCCAGU | 704 |
| 206 | UACCUAU CUGAUGAGGCCGAAAGGCCGAA AACCCAG | 705 |
| 209 | ACAUACC CUGAUGAGGCCGAAAGGCCGAA AUUAACC | 706 |
| 213 | UAUAACA CUGAUGAGGCCGAAAGGCCGAA ACCUAUU | 707 |
| 217 | CGCAUAU CUGAUGAGGCCGAAAGGCCGAA ACAUACC | 708 |
| 218 | UCGCAUA CUGAUGAGGCCGAAAGGCCGAA AACAUAC | 709 |
| 220 | CAUCGCA CUGAUGAGGCCGAAAGGCCGAA AUAACAU | 710 |
| 229 | UAACCUA CUGAUGAGGCCGAAAGGCCGAA ACAUCGC | 711 |
| 231 | CCUAACC CUGAUGAGGCCGAAAGGCCGAA AGACAUC | 712 |
| 235 | UCUUCCU CUGAUGAGGCCGAAAGGCCGAA ACCUAGA | 713 |
| 236 | CUCUUCC CUGAUGAGGCCGAAAGGCCGAA AACCUAG | 714 |
| 254 | GUAUUUU CUGAUGAGGCCGAAAGGCCGAA AUGGUGU | 715 |
| 260 | CUCUGAG CUGAUGAGGCCGAAAGGCCGAA AUUUUUA | 716 |
| 263 | CAUCUCU CUGAUGAGGCCGAAAGGCCGAA AGUAUUU | 717 |
| 277 | UACAUGA CUGAUGAGGCCGAAAGGCCGAA AUCCCGC | 718 |
| 279 | UUUACAU CUGAUGAGGCCGAAAGGCCGAA AUAUCCC | 719 |
| 284 | UUGCUUU CUGAUGAGGCCGAAAGGCCGAA ACAUGAU | 720 |
| 299 | UUACAUC CUGAUGAGGCCGAAAGGCCGAA ACUCCAU | 721 |
| 305 | GUGUUGU CUGAUGAGGCCGAAAGGCCGAA ACAUCUA | 722 |
| 315 | UCUUGAC CUGAUGAGGCCGAAAGGCCGAA AUGUGUU | 723 |
| 318 | AUGUCUU CUGAUGAGGCCGAAAGGCCGAA ACGAUGU | 724 |
| 326 | UUCCAUU CUGAUGAGGCCGAAAGGCCGAA AUGUCUU | 725 |
| 327 | UUUCCAU CUGAUGAGGCCGAAAGGCCGAA AAUGUCU | 726 |
| 346 | CACUUCA CUGAUGAGGCCGAAAGGCCGAA AUUUCAU | 727 |
| 347 | ACACUUC CUGAUGAGGCCGAAAGGCCGAA AAUUUCA | 728 |
| 355 | CAAUGUU CUGAUGAGGCCGAAAGGCCGAA ACACUUC | 729 |
| 356 | CCAAUGU CUGAUGAGGCCGAAAGGCCGAA AACACUU | 730 |
| 361 | GCUUGCC CUGAUGAGGCCGAAAGGCCGAA AUGUUAA | 731 |
| 370 | AGUUGUU CUGAUGAGGCCGAAAGGCCGAA AGCUUGC | 732 |
| 371 | CAGUUGU CUGAUGAGGCCGAAAGGCCGAA AAGCUUG | 733 |
| 383 | UGAUUUG CUGAUGAGGCCGAAAGGCCGAA AUUUCAG | 734 |
| 384 | UUGAUUU CUGAUGAGGCCGAAAGGCCGAA AAUUUCA | 735 |
| 389 | CAAUGUU CUGAUGAGGCCGAAAGGCCGAA AUUUGAA | 736 |
| 395 | CUAUCUC CUGAUGAGGCCGAAAGGCCGAA AUGUUGA | 737 |
| 401 | UAGAUUC CUGAUGAGGCCGAAAGGCCGAA AUCUCAA | 738 |
| 406 | UUUUCUA CUGAUGAGGCCGAAAGGCCGAA AUUCUAU | 739 |
| 408 | GAUUUUC CUGAUGAGGCCGAAAGGCCGAA AGAUUCU | 740 |
| 415 | UUUUUAG CUGAUGAGGCCGAAAGGCCGAA AUUUUCU | 741 |
| 418 | UUUUUUG CUGAUGAGGCCGAAAGGCCGAA AGGAUUU | 742 |
| 431 | UUUCUUU CUGAUGAGGCCGAAAGGCCGAA AGCAUUU | 743 |
| 449 | CUGGAGC CUGAUGAGGCCGAAAGGCCGAA ACCUCUC | 744 |
| 453 | UAUUCUG CUGAUGAGGCCGAAAGGCCGAA AGCUACC | 745 |
| 460 | AUGCCUG CUGAUGAGGCCGAAAGGCCGAA AUUCUGG | 746 |
| 472 | AUCAGGA CUGAUGAGGCCGAAAGGCCGAA AGUCAUG | 747 |
| 474 | CAAUCAG CUGAUGAGGCCGAAAGGCCGAA AGAGUCA | 748 |
| 480 | AUCCCAC CUGAUGAGGCCGAAAGGCCGAA AUCAGGA | 749 |
| 491 | AUAAUAU CUGAUGAGGCCGAAAGGCCGAA AUCAUCC | 750 |
| 494 | UACAUAA CUGAUGAGGCCGAAAGGCCGAA AUUAUCA | 751 |
| 496 | UAUACAU CUGAUGAGGCCGAAAGGCCGAA AUAUUAU | 752 |
| 497 | CUAUACA CUGAUGAGGCCGAAAGGCCGAA AAUAUUA | 753 |
| 501 | GCUGCUA CUGAUGAGGCCGAAAGGCCGAA ACAUAAU | 754 |
| 503 | AUGCUGC CUGAUGAGGCCGAAAGGCCGAA AUACAUA | 755 |
| 511 | UAUUACU CUGAUGAGGCCGAAAGGCCGAA AUGCUGC | 756 |
| 512 | UUAUUAC CUGAUGAGGCCGAAAGGCCGAA AAUGCUG | 757 |
| 515 | UAGUUAU CUGAUGAGGCCGAAAGGCCGAA ACUAAUG | 758 |
| 518 | AUUUAGU CUGAUGAGGCCGAAAGGCCGAA AUUACUA | 759 |
| 522 | GCUAAUU CUGAUGAGGCCGAAAGGCCGAA AGUUAUU | 760 |
| 526 | UGCUGCU CUGAUGAGGCCGAAAGGCCGAA AUUUAGU | 761 |
| 527 | CUGCUGC CUGAUGAGGCCGAAAGGCCGAA AAUUUAG | 762 |
| 544 | AAGACCA CUGAUGAGGCCGAAAGGCCGAA AUCUGUC | 763 |
| 549 | GCUGUAA CUGAUGAGGCCGAAAGGCCGAA ACCAGAU | 764 |
| 551 | CGGCUGU CUGAUGAGGCCGAAAGGCCGAA AGACCAG | 765 |
| 552 | ACGGCUG CUGAUGAGGCCGAAAGGCCGAA AAGACCA | 766 |
| 563 | CUCUCCU CUGAUGAGGCCGAAAGGCCGAA AUCACGG | 767 |
| 564 | GCUCUCC CUGAUGAGGCCGAAAGGCCGAA AAUCACG | 768 |
| 573 | ACAUUAU CUGAUGAGGCCGAAAGGCCGAA AGCUCUC | 769 |
| 576 | AGGACAU CUGAUGAGGCCGAAAGGCCGAA AUUAGCU | 770 |
| 581 | UUUUUAG CUGAUGAGGCCGAAAGGCCGAA ACAUUAU | 771 |
| 584 | CAUUUUU CUGAUGAGGCCGAAAGGCCGAA AGGACAU | 772 |

TABLE VII-continued

RSV (N) HH Ribozyme Sequence

| nt. Position | HH Ribozyme Sequence | Sequence ID No. |
|---|---|---|
| 603 | CCUUUGU CUGAUGAGGCCGAAAGGCCGAA ACGUUUC | 773 |
| 604 | GCCUUUG CUGAUGAGGCCGAAAGGCCGAA AACGUUU | 774 |
| 613 | GGGUAGU CUGAUGAGGCCGAAAGGCCGAA AGCCUUU | 775 |
| 614 | UGGGUAG CUGAUGAGGCCGAAAGGCCGAA AAGCCUU | 776 |
| 617 | CCUUGGG CUGAUGAGGCCGAAAGGCCGAA AGUAAGC | 777 |
| 629 | UGUUGGC CUGAUGAGGCCGAAAGGCCGAA AUGUCCU | 778 |
| 640 | UUCAUAG CUGAUGAGGCCGAAAGGCCGAA AGCUGUU | 779 |
| 641 | CUUCAUA CUGAUGAGGCCGAAAGGCCGAA AAGCUGU | 780 |
| 643 | CACUUCA CUGAUGAGGCCGAAAGGCCGAA AGAAGCU | 781 |
| 652 | UUUUUCA CUGAUGAGGCCGAAAGGCCGAA ACACUUC | 782 |
| 653 | GUUUUUC CUGAUGAGGCCGAAAGGCCGAA AACACUU | 783 |
| 663 | AAGUGGG CUGAUGAGGCCGAAAGGCCGAA AUGUUUU | 784 |
| 670 | AUCUAUA CUGAUGAGGCCGAAAGGCCGAA AGUGGGG | 785 |
| 671 | CAUCUAU CUGAUGAGGCCGAAAGGCCGAA AAGUGGG | 786 |
| 672 | ACAUCUA CUGAUGAGGCCGAAAGGCCGAA AAAGUGG | 787 |
| 674 | AAACAUC CUGAUGAGGCCGAAAGGCCGAA AUAAAGU | 788 |
| 680 | GAACAAA CUGAUGAGGCCGAAAGGCCGAA ACAUCUA | 789 |
| 681 | UGAACAA CUGAUGAGGCCGAAAGGCCGAA AACAUCU | 790 |
| 682 | AUGAACA CUGAUGAGGCCGAAAGGCCGAA AAACAUC | 791 |
| 683 | AAUGAAC CUGAUGAGGCCGAAAGGCCGAA AAAACAU | 792 |
| 686 | CAAAAUG CUGAUGAGGCCGAAAGGCCGAA ACAAAAA | 793 |
| 687 | CCAAAAU CUGAUGAGGCCGAAAGGCCGAA AACAAAA | 794 |
| 690 | AUACCAA CUGAUGAGGCCGAAAGGCCGAA AUGAACA | 795 |
| 691 | UAUACCA CUGAUGAGGCCGAAAGGCCGAA AAUGAAC | 796 |
| 692 | CUAUACC CUGAUGAGGCCGAAAGGCCGAA AAAUGAA | 797 |
| 696 | UGUGCUA CUGAUGAGGCCGAAAGGCCGAA ACCAAAA | 798 |
| 698 | AUUGUGC CUGAUGAGGCCGAAAGGCCGAA AUACCAA | 799 |
| 706 | GGUAGAA CUGAUGAGGCCGAAAGGCCGAA AUUGUGC | 800 |
| 708 | CUGGUAG CUGAUGAGGCCGAAAGGCCGAA AGAUUGU | 801 |
| 709 | UCUGGUA CUGAUGAGGCCGAAAGGCCGAA AAGAUUG | 802 |
| 711 | CCUCUGG CUGAUGAGGCCGAAAGGCCGAA AGAAGAU | 803 |
| 726 | UCAACUC CUGAUGAGGCCGAAAGGCCGAA ACUGCCA | 804 |
| 731 | UCCCUUC CUGAUGAGGCCGAAAGGCCGAA ACUCUAC | 805 |
| 740 | CUGCAAA CUGAUGAGGCCGAAAGGCCGAA AUCCCUU | 806 |
| 741 | CCUGCAA CUGAUGAGGCCGAAAGGCCGAA AAUCCCU | 807 |
| 742 | UCCUGCA CUGAUGAGGCCGAAAGGCCGAA AAAUCCC | 808 |
| 743 | AUCCUGC CUGAUGAGGCCGAAAGGCCGAA AAAAUCC | 809 |
| 751 | CAUAAAC CUGAUGAGGCCGAAAGGCCGAA AUCCUGC | 810 |
| 754 | AUUCAUA CUGAUGAGGCCGAAAGGCCGAA ACAAUCC | 811 |
| 755 | CAUUCAU CUGAUGAGGCCGAAAGGCCGAA AACAAUC | 812 |
| 756 | GCAUUCA CUGAUGAGGCCGAAAGGCCGAA AAACAAU | 813 |
| 766 | UGCACCA CUGAUGAGGCCGAAAGGCCGAA AGGCAUU | 814 |
| 787 | CCACCGU CUGAUGAGGCCGAAAGGCCGAA ACAUCAC | 815 |
| 788 | CCCACCG CUGAUGAGGCCGAAAGGCCGAA AACAUCA | 816 |
| 800 | UUGCUAA CUGAUGAGGCCGAAAGGCCGAA ACUCCCC | 817 |
| 802 | UUUUGCU CUGAUGAGGCCGAAAGGCCGAA AGACUCC | 818 |
| 803 | AUUUUGC CUGAUGAGGCCGAAAGGCCGAA AAGACUC | 819 |
| 811 | UUUAACU CUGAUGAGGCCGAAAGGCCGAA AUUUUGC | 820 |
| 815 | UAUUUUU CUGAUGAGGCCGAAAGGCCGAA ACUGAUU | 821 |
| 816 | AUAUUUU CUGAUGAGGCCGAAAGGCCGAA AACUGAU | 822 |
| 822 | AACAUAA CUGAUGAGGCCGAAAGGCCGAA AUUUUUA | 823 |
| 824 | CUAACAU CUGAUGAGGCCGAAAGGCCGAA AUAUUUU | 824 |
| 825 | CCUAACA CUGAUGAGGCCGAAAGGCCGAA AAUAUUU | 825 |
| 829 | AUGUCCU CUGAUGAGGCCGAAAGGCCGAA ACAUAAU | 826 |
| 830 | CAUGUCC CUGAUGAGGCCGAAAGGCCGAA AACAUAA | 827 |
| 840 | UGCACAC CUGAUGAGGCCGAAAGGCCGAA AGCAUGU | 828 |
| 866 | CCUCAAC CUGAUGAGGCCGAAAGGCCGAA ACUUGUU | 829 |
| 869 | AAACCUC CUGAUGAGGCCGAAAGGCCGAA ACAACUU | 830 |
| 875 | AUUCAUA CUGAUGAGGCCGAAAGGCCGAA ACCUCAA | 831 |
| 876 | UAUUCAU CUGAUGAGGCCGAAAGGCCGAA AACCUCA | 832 |
| 877 | AUAUUCA CUGAUGAGGCCGAAAGGCCGAA AAACCUC | 833 |
| 883 | UUGGGCA CUGAUGAGGCCGAAAGGCCGAA AUUCAUA | 834 |
| 895 | ACCACCC CUGAUGAGGCCGAAAGGCCGAA AUUUUUG | 835 |
| 913 | AUGGUAG CUGAUGAGGCCGAAAGGCCGAA AUCCUGC | 836 |
| 914 | UAUGGUA CUGAUGAGGCCGAAAGGCCGAA AAUCCUG | 837 |
| 916 | UAUAUGG CUGAUGAGGCCGAAAGGCCGAA AGAAUCC | 838 |
| 921 | UUCAAUA CUGAUGAGGCCGAAAGGCCGAA AUGGUAG | 839 |
| 923 | UGUUCAA CUGAUGAGGCCGAAAGGCCGAA AUAUGGU | 840 |
| 925 | GUUGUUC CUGAUGAGGCCGAAAGGCCGAA AUAUAUG | 841 |
| 943 | UAAUAAU CUGAUGAGGCCGAAAGGCCGAA AUGCUUU | 842 |
| 946 | AGAUAAU CUGAUGAGGCCGAAAGGCCGAA AUGAUGC | 843 |
| 947 | AAGAUAA CUGAUGAGGCCGAAAGGCCGAA AAUGAUG | 844 |
| 949 | CAAAGAU CUGAUGAGGCCGAAAGGCCGAA AUAAUGA | 845 |
| 950 | UCAAAGA CUGAUGAGGCCGAAAGGCCGAA AAUAAUG | 846 |

TABLE VII-continued

RSV (N) HH Ribozyme Sequence

| nt. Position | HH Ribozyme Sequence | Sequence ID No. |
|---|---|---|
| 952 | AGUCAAA CUGAUGAGGCCGAAAGGCCGAA AUAAUAA | 847 |
| 954 | UGAGUCA CUGAUGAGGCCGAAAGGCCGAA AGAUAAU | 848 |
| 955 | UUGAGUC CUGAUGAGGCCGAAAGGCCGAA AAGAUAA | 849 |
| 960 | GGAAAUU CUGAUGAGGCCGAAAGGCCGAA AGUCAAA | 850 |
| 964 | GUGAGGA CUGAUGAGGCCGAAAGGCCGAA AUUGAGU | 851 |
| 965 | AGUGAGG CUGAUGAGGCCGAAAGGCCGAA AAUUGAG | 852 |
| 966 | AAGUGAG CUGAUGAGGCCGAAAGGCCGAA AAAUUGA | 853 |
| 969 | GAGAAGU CUGAUGAGGCCGAAAGGCCGAA AGGAAAU | 854 |
| 973 | ACUGGAG CUGAUGAGGCCGAAAGGCCGAA AGUGAGG | 855 |
| 974 | CACUGGA CUGAUGAGGCCGAAAGGCCGAA AAGUGAG | 856 |
| 976 | UACACUG CUGAUGAGGCCGAAAGGCCGAA AGAAGUG | 857 |
| 983 | CUAAUAC CUGAUGAGGCCGAAAGGCCGAA ACACUGG | 858 |
| 986 | UGCCUAA CUGAUGAGGCCGAAAGGCCGAA ACUACAC | 859 |
| 988 | AUUGCCU CUGAUGAGGCCGAAAGGCCGAA AUACUAC | 860 |
| 989 | CAUUGCC CUGAUGAGGCCGAAAGGCCGAA AAUACUA | 861 |
| 1007 | UUAUGCC CUGAUGAGGCCGAAAGGCCGAA AGGCCAG | 862 |
| 1013 | CUCCCAU CUGAUGAGGCCGAAAGGCCGAA AUGCCUA | 863 |
| 1024 | ACCUCUG CUGAUGAGGCCGAAAGGCCGAA ACUCUCC | 864 |
| 1032 | CUCGGUG CUGAUGAGGCCGAAAGGCCGAA ACCUCUG | 865 |
| 1044 | AGAUCUU CUGAUGAGGCCGAAAGGCCGAA AUUCCUC | 866 |
| 1050 | UCAUAUA CUGAUGAGGCCGAAAGGCCGAA AUCUUGA | 867 |
| 1052 | CAUCAUA CUGAUGAGGCCGAAAGGCCGAA AGAUCUU | 868 |
| 1054 | UGCAUCA CUGAUGAGGCCGAAAGGCCGAA AUAGAUC | 869 |
| 1072 | UUCAGCA CUGAUGAGGCCGAAAGGCCGAA AUGCCUU | 870 |
| 1085 | UUUCUUU CUGAUGAGGCCGAAAGGCCGAA AGUUGUU | 871 |
| 1103 | UGUAGUU CUGAUGAGGCCGAAAGGCCGAA AUCACAC | 872 |
| 1104 | CUGUAGU CUGAUGAGGCCGAAAGGCCGAA AAUCACA | 873 |
| 1108 | UACACUG CUGAUGAGGCCGAAAGGCCGAA AGUUAAU | 874 |
| 1115 | AGUCUAG CUGAUGAGGCCGAAAGGCCGAA ACACUGU | 875 |
| 1118 | UCAAGUC CUGAUGAGGCCGAAAGGCCGAA AGUACAC | 876 |
| 1123 | UGCUGUC CUGAUGAGGCCGAAAGGCCGAA AGUCUAG | 877 |
| 1139 | UAGCCUC CUGAUGAGGCCGAAAGGCCGAA AGUUCUU | 878 |
| 1146 | UGUUUGA CUGAUGAGGCCGAAAGGCCGAA AGCCUCU | 879 |
| 1148 | GAUGUUU CUGAUGAGGCCGAAAGGCCGAA AUAGCCU | 880 |
| 1155 | UUAAGCU CUGAUGAGGCCGAAAGGCCGAA AUGUUUG | 881 |
| 1160 | UUGGAUU CUGAUGAGGCCGAAAGGCCGAA AGCUGAU | 882 |
| 1161 | UUUGGAU CUGAUGAGGCCGAAAGGCCGAA AAGCUGA | 883 |
| 1164 | UCUUUUG CUGAUGAGGCCGAAAGGCCGAA AUUAAGC | 884 |
| 1173 | ACAUCAU CUGAUGAGGCCGAAAGGCCGAA AUCUUUU | 885 |
| 1181 | AAAGCUC CUGAUGAGGCCGAAAGGCCGAA ACAUCAU | 886 |
| 1187 | UAACUCA CUGAUGAGGCCGAAAGGCCGAA AGCUCUA | 887 |
| 1188 | UUAACUC CUGAUGAGGCCGAAAGGCCGAA AAGCUCU | 888 |
| 1193 | UUUUAUU CUGAUGAGGCCGAAAGGCCGAA ACUCAAA | 889 |
| 1194 | UUUUUAU CUGAUGAGGCCGAAAGGCCGAA AACUCAA | 890 |

We claim:

1. An enzymatic RNA molecule which specifically cleaves genomic RNA of RSV or mRNA encoded by RSV in a region selected from the group consisting of 1C, 1B and N.

2. The enzymatic RNA molecule of claim 1, wherein said enzymatic RNA molecule comprises at least one sugar modification.

3. The enzymatic RNA molecule of claim 1, wherein said RNA molecule is in a hammerhead motif.

4. The hammerhead enzymatic RNA molecule of claim 3, wherein said hammerhead RNA molecule comprises sequences complementary to any of sequences defined as Seq ID Nos. 7–133, 261–351, and 443–666.

5. The enzymatic RNA molecule of claim 1, wherein said RNA molecule is in a hairpin, hepatitis Delta virus, group 1 intron, Neurospora VS RNA or RNaseP RNA motif.

6. The enzymatic RNA molecule of claim 5, wherein said enzymatic RNA molecule is in a hairpin motif and wherein said hairpin motif comprises sequences complementary to any of sequences defined as Seq ID Nos. 894–896 and 903–908.

7. The enzymatic RNA molecule of claim 1, wherein said ribozyme comprises between 12 and 100 bases complementary to the RNA of said region.

8. The enzymatic RNA of claim 7, wherein said ribozyme comprises between 14 and 24 bases complementary to the RNA of said region.

9. The enzymatic RNA molecule of claim 1 wherein said enzymatic RNA molecule comprises any sequence selected from the group consisting of SEQ ID Nos. 134–260, 352–442, 667–890, 894–896, and 897–902.

10. A mammalian cell including an enzymatic RNA molecule of claim 1 in vitro.

11. The cell of claim 10, wherein said cell is a human cell.

12. An expression vector comprising nucleic acid encoding the enzymatic RNA molecule of claim 1, in a manner which allows expression and/or delivery of that enzymatic RNA molecule within a mammalian cell in vitro.

13. A mammalian cell in vitro including an expression vector of claim 12.

14. The cell of claim 13, wherein said cell is a human cell.

* * * * *

UNITED STATES PATENT AND TRADEMARK OFFICE
CERTIFICATE OF CORRECTION

PATENT NO. : 5,693,532
DATED : December 2, 1997
INVENTOR(S) : James MCWIGGEN, KENNETH DRAPER, PAM PAVCO, TOD WOOLF It is certified that error appears in the above-identified patent and that said Letters Patent is hereby corrected as shown below:

Column 1, Line 8: Delete "ad" and insert --art--

Column 4, Line 36: Delete "Ceil" and insert --Cell--

Column 6, Line 35: Delete " "" " and insert -- ---- --

Claim 1, Column 329, Line 57: Delete "specitically" and insert --specifically--

Signed and Sealed this

Thirteenth Day of October 1998

Attest:

BRUCE LEHMAN

Attesting Officer          Commissioner of Patents and Trademarks

SEQUENCE LISTING ( 1 ) GENERAL INFORMATION:

( i i i ) NUMBER OF SEQUENCES: 909

( 2 ) INFORMATION FOR SEQ ID NO: 1:

( i ) SEQUENCE CHARACTERISTICS:
        ( A ) LENGTH: 11
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for
        any base. "H" represents
        nucleotide C, A, or U.

( x i ) SEQUENCE DESCRIPTION: SEQ ID NO: 1:

NNNNUHNNNN N        1 1

( 2 ) INFORMATION FOR SEQ ID NO: 2:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for
        any base.

( x i ) SEQUENCE DESCRIPTION: SEQ ID NO: 2:

| | |
|---|---:|
| NNNNNCUGAN GAGNNNNNNC GAAANNNN | 28 |

( 2 ) INFORMATION FOR SEQ ID NO: 3:

( i ) SEQUENCE CHARACTERISTICS:
        ( A ) LENGTH: 15
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for
        any base. The letter "Y"is
        U or C. The letter "H"is
        A, U, or C.

( x i ) SEQUENCE DESCRIPTION: SEQ ID NO: 3:

| | |
|---|---:|
| NNNNNNNYNG HYNNN | 15 |

( 2 ) INFORMATION FOR SEQ ID NO: 4:

( i ) SEQUENCE CHARACTERISTICS:
        ( A ) LENGTH: 47
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for
        any base.

( x i ) SEQUENCE DESCRIPTION: SEQ ID NO: 4:

| | |
|---|---:|
| NNNNGAAGNN NNNNNNNNNA AAHANNNNNN NACAUUACNN NNNNNNN | 47 |

( 2 ) INFORMATION FOR SEQ ID NO: 5:

( i ) SEQUENCE CHARACTERISTICS:
        ( A ) LENGTH: 85
        ( B ) TYPE: nucleic acid
        ( C ) STRANDEDNESS: single
        ( D ) TOPOLOGY: linear ( x i ) SEQUENCE DESCRIPTION: SEQ ID NO: 5:

| | |
|---|---:|
| UGGCCGGCAU GGUCCCAGCC UCCUCGCUGG CGCCGGCUGG GCAACAUUCC GAGGGGACCG | 60 |
| UCCCCUCGGU AAUGGCGAAU GGGAC | 85 |

( 2 ) INFORMATION FOR SEQ ID NO: 6:

( i ) SEQUENCE CHARACTERISTICS:
        ( A ) LENGTH: 176
        ( B ) TYPE: nucleic acid
        ( C ) STRANDEDNESS: single
        ( D ) TOPOLOGY: linear ( x i ) SEQUENCE DESCRIPTION: SEQ ID NO: 6:

| | |
|---|---:|
| GGGAAAGCUU GCGAAGGGCG UCGUCGCCCC GAGCGGUAGU AAGCAGGGAA CUCACCUCCA | 60 |

| AUUUCAGUAC | UGAAAUUGUC | GUAGCAGUUG | ACUACUGUUA | UGUGAUUGGU | AGAGGCUAAG | 120 |
| UGACGGUAUU | GGCGUAAGUC | AGUAUUGCAG | CACAGCACAA | GCCCGCUUGC | GAGAAU | 176 |

( 2 ) INFORMATION FOR SEQ ID NO: 7:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 7:

GGCAAAUAAG AAUUU                              15

( 2 ) INFORMATION FOR SEQ ID NO: 8:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 8:

UAAGAAUUUG AUAAG                              15

( 2 ) INFORMATION FOR SEQ ID NO: 9:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 9:

AAGAAUUUGA UAAGU                              15

( 2 ) INFORMATION FOR SEQ ID NO: 10:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 10:

AUUUGAUAAG UACCA                              15

( 2 ) INFORMATION FOR SEQ ID NO: 11:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 11:

GAUAAGUACC ACUUA                              15

( 2 ) INFORMATION FOR SEQ ID NO: 12:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 12:

UACCACUUAA AUUUA 15

( 2 ) INFORMATION FOR SEQ ID NO: 13:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 13:

ACCACUUAAA UUUAA 15

( 2 ) INFORMATION FOR SEQ ID NO: 14:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 14:

CUUAAAUUUA ACUCC 15

( 2 ) INFORMATION FOR SEQ ID NO: 15:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 15:

UUAAAUUUAA CUCCC 15

( 2 ) INFORMATION FOR SEQ ID NO: 16:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 16:

UAAAUUUAAC UCCCU 15

( 2 ) INFORMATION FOR SEQ ID NO: 17:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 17:

UUUAACUCCC UUGGU 15

( 2 ) INFORMATION FOR SEQ ID NO: 18:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 18:

ACUCCCUUGG UUAGA 15

( 2 ) INFORMATION FOR SEQ ID NO: 19:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 19:

CCUUGGUUAG AGAUG         15

( 2 ) INFORMATION FOR SEQ ID NO: 20:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 20:

CUUGGUUAGA GAUGG         15

( 2 ) INFORMATION FOR SEQ ID NO: 21:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 21:

CAGCAAUUCA UUGAG         15

( 2 ) INFORMATION FOR SEQ ID NO: 22:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 22:

AGCAAUUCAU UGAGU         15

( 2 ) INFORMATION FOR SEQ ID NO: 23:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 23:

AAUUCAUUGA GUAUG         15

( 2 ) INFORMATION FOR SEQ ID NO: 24:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 24:

AUUGAGUAUG AUAAA         15

( 2 ) INFORMATION FOR SEQ ID NO: 25:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 25:

GUAUGAUAAA AGUUA 15

( 2 ) INFORMATION FOR SEQ ID NO: 26:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 26:

UAAAGUUAG AUUAC 15

( 2 ) INFORMATION FOR SEQ ID NO: 27:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 27:

AAAGUUAGA UUACA 15

( 2 ) INFORMATION FOR SEQ ID NO: 28:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 28:

GUUAGAUUAC AAAAU 15

( 2 ) INFORMATION FOR SEQ ID NO: 29:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 29:

UUAGAUUACA AAAUU 15

( 2 ) INFORMATION FOR SEQ ID NO: 30:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 30:

ACAAAAUUUG UUUGA 15

( 2 ) INFORMATION FOR SEQ ID NO: 31:

( i ) SEQUENCE CHARACTERISTICS:
   ( A ) LENGTH: 15 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 31:

CAAAAUUUGU UUGAC  15

( 2 ) INFORMATION FOR SEQ ID NO: 32:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 32:

AAUUUGUUUG ACAAU  15

( 2 ) INFORMATION FOR SEQ ID NO: 33:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 33:

AUUUGUUUGA CAAUG  15

( 2 ) INFORMATION FOR SEQ ID NO: 34:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 34:

AUGAAGUAGC AUUGU  15

( 2 ) INFORMATION FOR SEQ ID NO: 35:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 35:

GUAGCAUUGU UAAAA  15

( 2 ) INFORMATION FOR SEQ ID NO: 36:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 36:

GCAUUGUUAA AAAUA  15

( 2 ) INFORMATION FOR SEQ ID NO: 37:

( i ) SEQUENCE CHARACTERISTICS:
      ( A ) LENGTH: 15 base pairs (B) TYPE: nucleic acid
            (C) STRANDEDNESS: single
            (D) TOPOLOGY: linear (x i) SEQUENCE DESCRIPTION: SEQ ID NO: 37:

CAUUGUUAAA AAUAA								15

(2) INFORMATION FOR SEQ ID NO: 38:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (x i) SEQUENCE DESCRIPTION: SEQ ID NO: 38:

UAAAAAUAAC AUGCU								15

(2) INFORMATION FOR SEQ ID NO: 39:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (x i) SEQUENCE DESCRIPTION: SEQ ID NO: 39:

ACAUGCUAUA CUGAU								15

(2) INFORMATION FOR SEQ ID NO: 40:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (x i) SEQUENCE DESCRIPTION: SEQ ID NO: 40:

AUGCUAUACU GAUAA								15

(2) INFORMATION FOR SEQ ID NO: 41:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (x i) SEQUENCE DESCRIPTION: SEQ ID NO: 41:

UACUGAUAAA UUAAU								15

(2) INFORMATION FOR SEQ ID NO: 42:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (x i) SEQUENCE DESCRIPTION: SEQ ID NO: 42:

GAUAAAUUAA UACAU								15

(2) INFORMATION FOR SEQ ID NO: 43:

(i) SEQUENCE CHARACTERISTICS:
            (A) LENGTH: 15 base pairs
            (B) TYPE: nucleic acid
            (C) STRANDEDNESS: single 5,693,532

49

-continued ( D ) TOPOLOGY: linear ( x i ) SEQUENCE DESCRIPTION: SEQ ID NO: 43:

AUAAAUUAAU ACAUU                                                              15

( 2 ) INFORMATION FOR SEQ ID NO: 44:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 44:

AAUUAAUACA UUUAA                                                              15

( 2 ) INFORMATION FOR SEQ ID NO: 45:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 45:

AAUACAUUUA ACUAA                                                              15

( 2 ) INFORMATION FOR SEQ ID NO: 46:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 46:

AUACAUUUAA CUAAC                                                              15

( 2 ) INFORMATION FOR SEQ ID NO: 47:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 47:

UACAUUUAAC UAACG                                                              15

( 2 ) INFORMATION FOR SEQ ID NO: 48:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 48:

UUUAACUAAC GCUUU                                                              15

( 2 ) INFORMATION FOR SEQ ID NO: 49:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 49:

UAACGCUUUG GCUAA  15

( 2 ) INFORMATION FOR SEQ ID NO: 50:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 50:

AACGCUUUGG CUAAG  15

( 2 ) INFORMATION FOR SEQ ID NO: 51:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 51:

UUUGGCUAAG GCAGU  15

( 2 ) INFORMATION FOR SEQ ID NO: 52:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 52:

CAGUGAUACA UACAA  15

( 2 ) INFORMATION FOR SEQ ID NO: 53:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 53:

GAUACAUACA AUCAA  15

( 2 ) INFORMATION FOR SEQ ID NO: 54:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 54:

AUACAAUCAA AUUGA  15

( 2 ) INFORMATION FOR SEQ ID NO: 55:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 55:

AUCAAAUUGA AUGGC 15

(2) INFORMATION FOR SEQ ID NO: 56:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 56:

AUGGCAUUGU GUUUG 15

(2) INFORMATION FOR SEQ ID NO: 57:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 57:

AUUGUGUUUG UGCAU 15

(2) INFORMATION FOR SEQ ID NO: 58:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 58:

UUGUGUUUGU GCAUG 15

(2) INFORMATION FOR SEQ ID NO: 59:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 59:

UGCAUGUUAU UACAA 15

(2) INFORMATION FOR SEQ ID NO: 60:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 60:

GCAUGUUAUU ACAAG 15

(2) INFORMATION FOR SEQ ID NO: 61:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 61:

AUGUUAUUAC AAGUA 15

( 2 ) INFORMATION FOR SEQ ID NO: 62:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 62:

UGUUAUUACA AGUAG                                               15

( 2 ) INFORMATION FOR SEQ ID NO: 63:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 63:

UACAAGUAGU GAUAU                                               15

( 2 ) INFORMATION FOR SEQ ID NO: 64:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 64:

UAGUGAUAUU UGCCC                                               15

( 2 ) INFORMATION FOR SEQ ID NO: 65:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 65:

GUGAUAUUUG CCCUA                                               15

( 2 ) INFORMATION FOR SEQ ID NO: 66:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 66:

UGAUAUUUGC CCUAA                                               15

( 2 ) INFORMATION FOR SEQ ID NO: 67:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 67:

UUGCCCUAAU AAUAA                                               15

( 2 ) INFORMATION FOR SEQ ID NO: 68:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 68:

CCCUAAUAAU AAUAU    15

( 2 ) INFORMATION FOR SEQ ID NO: 69:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 69:

UAAUAAUAAU AUUGU    15

( 2 ) INFORMATION FOR SEQ ID NO: 70:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 70:

UAAUAAUAUU GUAGU    15

( 2 ) INFORMATION FOR SEQ ID NO: 71:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 71:

AUAAUAUUGU AGUAA    15

( 2 ) INFORMATION FOR SEQ ID NO: 72:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 72:

AUAUUGUAGU AAAAU    15

( 2 ) INFORMATION FOR SEQ ID NO: 73:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 73:

UUGUAGUAAA AUCCA    15

( 2 ) INFORMATION FOR SEQ ID NO: 74:

( i ) SEQUENCE CHARACTERISTICS:

(A) LENGTH: 15 base pairs
(B) TYPE: nucleic acid
(C) STRANDEDNESS: single
(D) TOPOLOGY: linear (x i) SEQUENCE DESCRIPTION: SEQ ID NO: 74:

GUAAAAUCCA AUUUC            15

(2) INFORMATION FOR SEQ ID NO: 75:

(i) SEQUENCE CHARACTERISTICS:
(A) LENGTH: 15 base pairs
(B) TYPE: nucleic acid
(C) STRANDEDNESS: single
(D) TOPOLOGY: linear (x i) SEQUENCE DESCRIPTION: SEQ ID NO: 75:

AUCCAAUUUC ACAAC            15

(2) INFORMATION FOR SEQ ID NO: 76:

(i) SEQUENCE CHARACTERISTICS:
(A) LENGTH: 15 base pairs
(B) TYPE: nucleic acid
(C) STRANDEDNESS: single
(D) TOPOLOGY: linear (x i) SEQUENCE DESCRIPTION: SEQ ID NO: 76:

UCCAAUUUCA CAACA            15

(2) INFORMATION FOR SEQ ID NO: 77:

(i) SEQUENCE CHARACTERISTICS:
(A) LENGTH: 15 base pairs
(B) TYPE: nucleic acid
(C) STRANDEDNESS: single
(D) TOPOLOGY: linear (x i) SEQUENCE DESCRIPTION: SEQ ID NO: 77:

CCAAUUUCAC AACAA            15

(2) INFORMATION FOR SEQ ID NO: 78:

(i) SEQUENCE CHARACTERISTICS:
(A) LENGTH: 15 base pairs
(B) TYPE: nucleic acid
(C) STRANDEDNESS: single
(D) TOPOLOGY: linear (x i) SEQUENCE DESCRIPTION: SEQ ID NO: 78:

UGCCAGUACU ACAAA            15

(2) INFORMATION FOR SEQ ID NO: 79:

(i) SEQUENCE CHARACTERISTICS:
(A) LENGTH: 15 base pairs
(B) TYPE: nucleic acid
(C) STRANDEDNESS: single
(D) TOPOLOGY: linear (x i) SEQUENCE DESCRIPTION: SEQ ID NO: 79:

CAGUACUACA AAAUG            15

(2) INFORMATION FOR SEQ ID NO: 80:

(i) SEQUENCE CHARACTERISTICS:
(A) LENGTH: 15 base pairs
(B) TYPE: nucleic acid (C) STRANDEDNESS: single
        (D) TOPOLOGY: linear (xi) SEQUENCE DESCRIPTION: SEQ ID NO: 80:

UGGAGGUUAU AUAUG                                                                                15

(2) INFORMATION FOR SEQ ID NO: 81:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 81:

GGAGGUUAUA UAUGG                                                                                15

(2) INFORMATION FOR SEQ ID NO: 82:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 82:

AGGUUAUAUA UGGGA                                                                                15

(2) INFORMATION FOR SEQ ID NO: 83:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 83:

GUUAUAUAUG GGAAA                                                                                15

(2) INFORMATION FOR SEQ ID NO: 84:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 84:

AUGGAAUUAA CACAU                                                                                15

(2) INFORMATION FOR SEQ ID NO: 85:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 85:

UGGAAUUAAC ACAUU                                                                                15

(2) INFORMATION FOR SEQ ID NO: 86:

(i) SEQUENCE CHARACTERISTICS:
        (A) LENGTH: 15 base pairs
        (B) TYPE: nucleic acid
        (C) STRANDEDNESS: single
        (D) TOPOLOGY: linear ( x i ) SEQUENCE DESCRIPTION: SEQ ID NO: 86:

AACACAUUGC UCUCA    15

( 2 ) INFORMATION FOR SEQ ID NO: 87:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 87:

CAUUGCUCUC AACCU    15

( 2 ) INFORMATION FOR SEQ ID NO: 88:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 88:

UUGCUCUCAA CCUAA    15

( 2 ) INFORMATION FOR SEQ ID NO: 89:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 89:

UCAACCUAAU GGUCU    15

( 2 ) INFORMATION FOR SEQ ID NO: 90:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 90:

UAAUGGUCUA CUAGA    15

( 2 ) INFORMATION FOR SEQ ID NO: 91:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 91:

AUGGUCUACU AGAUG    15

( 2 ) INFORMATION FOR SEQ ID NO: 92:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 92:

GUCUACUAGA UGACA 15

( 2 ) INFORMATION FOR SEQ ID NO: 93:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 93:

UGACAAUUGU GAAAU 15

( 2 ) INFORMATION FOR SEQ ID NO: 94:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 94:

GUGAAAUUAA AUUCU 15

( 2 ) INFORMATION FOR SEQ ID NO: 95:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 95:

UGAAAUUAAA UUCUC 15

( 2 ) INFORMATION FOR SEQ ID NO: 96:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 96:

AUUAAAUUCU CCAAA 15

( 2 ) INFORMATION FOR SEQ ID NO: 97:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 97:

UUAAAUUCUC CAAAA 15

( 2 ) INFORMATION FOR SEQ ID NO: 98:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 98:

AAAUUCUCCA AAAAA 15

( 2 ) INFORMATION FOR SEQ ID NO: 99:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 99:

AAAAACUAAG UGAUU        15

( 2 ) INFORMATION FOR SEQ ID NO: 100:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 100:

AAGUGAUUCA ACAAU        15

( 2 ) INFORMATION FOR SEQ ID NO: 101:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 101:

AGUGAUUCAA CAAUG        15

( 2 ) INFORMATION FOR SEQ ID NO: 102:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 102:

GACCAAUUAU AUGAA        15

( 2 ) INFORMATION FOR SEQ ID NO: 103:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 103:

ACCAAUUAUA UGAAU        15

( 2 ) INFORMATION FOR SEQ ID NO: 104:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 104:

CAAUUAUAUG AAUCA        15

( 2 ) INFORMATION FOR SEQ ID NO: 105:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 105:

UAUGAAUCAA UUAUC 15

( 2 ) INFORMATION FOR SEQ ID NO: 106:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 106:

AAUCAAUUAU CUGAA 15

( 2 ) INFORMATION FOR SEQ ID NO: 107:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 107:

AUCAAUUAUC UGAAU 15

( 2 ) INFORMATION FOR SEQ ID NO: 108:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 108:

CAAUUAUCUG AAUUA 15

( 2 ) INFORMATION FOR SEQ ID NO: 109:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 109:

UCUGAAUUAC UUGGA 15

( 2 ) INFORMATION FOR SEQ ID NO: 110:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 110:

CUGAAUUACU UGGAU 15

( 2 ) INFORMATION FOR SEQ ID NO: 111:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 111:

AAUUACUUGG AUUUG     15

( 2 ) INFORMATION FOR SEQ ID NO: 112:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 112:

CUUGGAUUUG AUCUU     15

( 2 ) INFORMATION FOR SEQ ID NO: 113:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 113:

UUGGAUUUGA UCUUA     15

( 2 ) INFORMATION FOR SEQ ID NO: 114:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 114:

AUUUGAUCUU AAUCC     15

( 2 ) INFORMATION FOR SEQ ID NO: 115:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 115:

UUGAUCUUAA UCCAU     15

( 2 ) INFORMATION FOR SEQ ID NO: 116:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 116:

UGAUCUUAAU CCAUA     15

( 2 ) INFORMATION FOR SEQ ID NO: 117:

( i ) SEQUENCE CHARACTERISTICS:
    ( A ) LENGTH: 15 base pairs ( B ) TYPE: nucleic acid
                ( C ) STRANDEDNESS: single
                ( D ) TOPOLOGY: linear ( x i ) SEQUENCE DESCRIPTION: SEQ ID NO: 117:

UCUUAAUCCA UAAAU                                                                                          15

( 2 ) INFORMATION FOR SEQ ID NO: 118:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 118:

AAUCCAUAAA UUAUA                                                                                          15

( 2 ) INFORMATION FOR SEQ ID NO: 119:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 119:

CAUAAAUUAU AAUUA                                                                                          15

( 2 ) INFORMATION FOR SEQ ID NO: 120:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 120:

AUAAAUUAUA AUUAA                                                                                          15

( 2 ) INFORMATION FOR SEQ ID NO: 121:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 121:

AAAUUAUAAU UAAUA                                                                                          15

( 2 ) INFORMATION FOR SEQ ID NO: 122:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 122:

UUAUAAUUAA UAUCA                                                                                          15

( 2 ) INFORMATION FOR SEQ ID NO: 123:

( i ) SEQUENCE CHARACTERISTICS:
                ( A ) LENGTH: 15 base pairs
                ( B ) TYPE: nucleic acid
                ( C ) STRANDEDNESS: single (D) TOPOLOGY: linear (xi) SEQUENCE DESCRIPTION: SEQ ID NO: 123:

UAUAAUUAAU AUCAA 15

(2) INFORMATION FOR SEQ ID NO: 124:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 124:

AAUUAAUAUC AACUA 15

(2) INFORMATION FOR SEQ ID NO: 125:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 125:

UUAAUAUCAA CUAGC 15

(2) INFORMATION FOR SEQ ID NO: 126:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 126:

AUCAACUAGC AAAUC 15

(2) INFORMATION FOR SEQ ID NO: 127:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 127:

AGCAAAUCAA UGUCA 15

(2) INFORMATION FOR SEQ ID NO: 128:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 128:

UCAAUGUCAC UAACA 15

(2) INFORMATION FOR SEQ ID NO: 129:

(i) SEQUENCE CHARACTERISTICS:
        (A) LENGTH: 15 base pairs
        (B) TYPE: nucleic acid
        (C) STRANDEDNESS: single
        (D) TOPOLOGY: linear ( x i ) SEQUENCE DESCRIPTION: SEQ ID NO: 129:

UGUCACUAAC ACCAU                                                           15

( 2 ) INFORMATION FOR SEQ ID NO: 130:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 130:

ACACCAUUAG UUAAU                                                           15

( 2 ) INFORMATION FOR SEQ ID NO: 131:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 131:

CACCAUUAGU UAAUA                                                           15

( 2 ) INFORMATION FOR SEQ ID NO: 132:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 132:

CAUUAGUUAA UAUAA                                                           15

( 2 ) INFORMATION FOR SEQ ID NO: 133:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 133:

AUUAGUUAAU AUAAA                                                           15

( 2 ) INFORMATION FOR SEQ ID NO: 134:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 134:

AAAUUCUCUG AUGAGGCCGA AAGGCCGAAA UUUGCC                                    36

( 2 ) INFORMATION FOR SEQ ID NO: 135:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 135:

CUUAUCACUG AUGAGGCCGA AAGGCCGAAA UUCUUA 36

(2) INFORMATION FOR SEQ ID NO: 136:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 136:

ACUUAUCCUG AUGAGGCCGA AAGGCCGAAA AUUCUU 36

(2) INFORMATION FOR SEQ ID NO: 137:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 137:

UGGUACUCUG AUGAGGCCGA AAGGCCGAAA UCAAAU 36

(2) INFORMATION FOR SEQ ID NO: 138:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 138:

UAAGUGGCUG AUGAGGCCGA AAGGCCGAAA CUUAUC 36

(2) INFORMATION FOR SEQ ID NO: 139:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 139:

UAAAUUUCUG AUGAGGCCGA AAGGCCGAAA GUGGUA 36

(2) INFORMATION FOR SEQ ID NO: 140:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 140:

UUAAAUUCUG AUGAGGCCGA AAGGCCGAAA AGUGGU 36

(2) INFORMATION FOR SEQ ID NO: 141:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 141:

GGAGUUACUG AUGAGGCCGA AAGGCCGAAA UUUAAG 36

( 2 ) INFORMATION FOR SEQ ID NO: 142:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 142:

GGGAGUUCUG AUGAGGCCGA AAGGCCGAAA AUUUAA    36

( 2 ) INFORMATION FOR SEQ ID NO: 143:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 143:

AGGGAGUCUG AUGAGGCCGA AAGGCCGAAA AAUUUA    36

( 2 ) INFORMATION FOR SEQ ID NO: 144:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 144:

ACCAAGGCUG AUGAGGCCGA AAGGCCGAAA GUUAAA    36

( 2 ) INFORMATION FOR SEQ ID NO: 145:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 145:

UCUAACCCUG AUGAGGCCGA AAGGCCGAAA GGGAGU    36

( 2 ) INFORMATION FOR SEQ ID NO: 146:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 146:

CAUCUCUCUG AUGAGGCCGA AAGGCCGAAA CCAAGG    36

( 2 ) INFORMATION FOR SEQ ID NO: 147:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 147:

CCAUCUCCUG AUGAGGCCGA AAGGCCGAAA ACCAAG    36

( 2 ) INFORMATION FOR SEQ ID NO: 148:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 148:

CUCAAUGCUG AUGAGGCCGA AAGGCCGAAA UUGCUG      36

( 2 ) INFORMATION FOR SEQ ID NO: 149:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 149:

ACUCAAUCUG AUGAGGCCGA AAGGCCGAAA AUUGCU      36

( 2 ) INFORMATION FOR SEQ ID NO: 150:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 150:

CAUACUCCUG AUGAGGCCGA AAGGCCGAAA UGAAUU      36

( 2 ) INFORMATION FOR SEQ ID NO: 151:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 151:

UUUAUCACUG AUGAGGCCGA AAGGCCGAAA CUCAAU      36

( 2 ) INFORMATION FOR SEQ ID NO: 152:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 152:

UAACUUUCUG AUGAGGCCGA AAGGCCGAAA UCAUAC      36

( 2 ) INFORMATION FOR SEQ ID NO: 153:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 153:

GUAAUCUCUG AUGAGGCCGA AAGGCCGAAA CUUUUA      36

( 2 ) INFORMATION FOR SEQ ID NO: 154:

( i ) SEQUENCE CHARACTERISTICS:

(A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 154:

UGUAAUCCUG AUGAGGCCGA AAGGCCGAAA ACUUUU                36

(2) INFORMATION FOR SEQ ID NO: 155:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 155:

AUUUUGUCUG AUGAGGCCGA AAGGCCGAAA UCUAAC                36

(2) INFORMATION FOR SEQ ID NO: 156:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 156:

AAUUUUGCUG AUGAGGCCGA AAGGCCGAAA AUCUAA                36

(2) INFORMATION FOR SEQ ID NO: 157:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 157:

UCAAACACUG AUGAGGCCGA AAGGCCGAAA UUUUGU                36

(2) INFORMATION FOR SEQ ID NO: 158:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 158:

GUCAAACCUG AUGAGGCCGA AAGGCCGAAA AUUUUG                36

(2) INFORMATION FOR SEQ ID NO: 159:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 159:

AUUGUCACUG AUGAGGCCGA AAGGCCGAAA CAAAUU                36

(2) INFORMATION FOR SEQ ID NO: 160:

(i) SEQUENCE CHARACTERISTICS:
        (A) LENGTH: 36 base pairs
        (B) TYPE: nucleic acid ( C ) STRANDEDNESS: single
        ( D ) TOPOLOGY: linear ( x i ) SEQUENCE DESCRIPTION: SEQ ID NO: 160:

CAUUGUCCUG AUGAGGCCGA AAGGCCGAAA ACAAAU  36

( 2 ) INFORMATION FOR SEQ ID NO: 161:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 161:

ACAAUGCCUG AUGAGGCCGA AAGGCCGAAA CUUCAU  36

( 2 ) INFORMATION FOR SEQ ID NO: 162:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 162:

UUUUAACCUG AUGAGGCCGA AAGGCCGAAA UGCUAC  36

( 2 ) INFORMATION FOR SEQ ID NO: 163:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 163:

UAUUUUCUG AUGAGGCCGA AAGGCCGAAA CAAUGC  36

( 2 ) INFORMATION FOR SEQ ID NO: 164:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 164:

UUAUUUUCUG AUGAGGCCGA AAGGCCGAAA ACAAUG  36

( 2 ) INFORMATION FOR SEQ ID NO: 165:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 165:

AGCAUGUCUG AUGAGGCCGA AAGGCCGAAA UUUUUA  36

( 2 ) INFORMATION FOR SEQ ID NO: 166:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 166:

AUCAGUACUG AUGAGGCCGA AAGGCCGAAA GCAUGU    36

( 2 ) INFORMATION FOR SEQ ID NO: 167:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 167:

UUAUCAGCUG AUGAGGCCGA AAGGCCGAAA UAGCAU    36

( 2 ) INFORMATION FOR SEQ ID NO: 168:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 168:

AUUAAUUCUG AUGAGGCCGA AAGGCCGAAA UCAGUA    36

( 2 ) INFORMATION FOR SEQ ID NO: 169:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 169:

AUGUAUUCUG AUGAGGCCGA AAGGCCGAAA UUUAUC    36

( 2 ) INFORMATION FOR SEQ ID NO: 170:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 170:

AAUGUAUCUG AUGAGGCCGA AAGGCCGAAA AUUUAU    36

( 2 ) INFORMATION FOR SEQ ID NO: 171:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 171:

UUAAAUGCUG AUGAGGCCGA AAGGCCGAAA UUAAUU    36

( 2 ) INFORMATION FOR SEQ ID NO: 172:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 172:

UUAGUUACUG AUGAGGCCGA AAGGCCGAAA UGUAUU                36

( 2 ) INFORMATION FOR SEQ ID NO: 173:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 173:

GUUAGUUCUG AUGAGGCCGA AAGGCCGAAA AUGUAU                36

( 2 ) INFORMATION FOR SEQ ID NO: 174:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 174:

CGUUAGUCUG AUGAGGCCGA AAGGCCGAAA AAUGUA                36

( 2 ) INFORMATION FOR SEQ ID NO: 175:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 175:

AAAGCGUCUG AUGAGGCCGA AAGGCCGAAA GUUAAA                36

( 2 ) INFORMATION FOR SEQ ID NO: 176:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 176:

UUAGCCACUG AUGAGGCCGA AAGGCCGAAA GCGUUA                36

( 2 ) INFORMATION FOR SEQ ID NO: 177:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 177:

CUUAGCCCUG AUGAGGCCGA AAGGCCGAAA AGCGUU                36

( 2 ) INFORMATION FOR SEQ ID NO: 178:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 178:

ACUGCCUCUG AUGAGGCCGA AAGGCCGAAA GCCAAA                36

( 2 ) INFORMATION FOR SEQ ID NO: 179:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 179:

UUGUAUGCUG AUGAGGCCGA AAGGCCGAAA UCACUG      36

( 2 ) INFORMATION FOR SEQ ID NO: 180:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 180:

UUGAUUGCUG AUGAGGCCGA AAGGCCGAAA UGUAUC      36

( 2 ) INFORMATION FOR SEQ ID NO: 181:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 181:

UCAAUUUCUG AUGAGGCCGA AAGGCCGAAA UUGUAU      36

( 2 ) INFORMATION FOR SEQ ID NO: 182:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 182:

GCCAUUCCUG AUGAGGCCGA AAGGCCGAAA UUUGAU      36

( 2 ) INFORMATION FOR SEQ ID NO: 183:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 183:

CAAACACCUG AUGAGGCCGA AAGGCCGAAA UGCCAU      36

( 2 ) INFORMATION FOR SEQ ID NO: 184:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 184:

AUGCACACUG AUGAGGCCGA AAGGCCGAAA CACAAU      36

( 2 ) INFORMATION FOR SEQ ID NO: 185:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 185:

CAUGCACCUG AUGAGGCCGA AAGGCCGAAA ACACAA     36

( 2 ) INFORMATION FOR SEQ ID NO: 186:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 186:

UUGUAAUCUG AUGAGGCCGA AAGGCCGAAA CAUGCA     36

( 2 ) INFORMATION FOR SEQ ID NO: 187:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 187:

CUUGUAACUG AUGAGGCCGA AAGGCCGAAA ACAUGC     36

( 2 ) INFORMATION FOR SEQ ID NO: 188:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 188:

UACUUGUCUG AUGAGGCCGA AAGGCCGAAA UAACAU     36

( 2 ) INFORMATION FOR SEQ ID NO: 189:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 189:

CUACUUGCUG AUGAGGCCGA AAGGCCGAAA AUAACA     36

( 2 ) INFORMATION FOR SEQ ID NO: 190:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 190:

AUAUCACCUG AUGAGGCCGA AAGGCCGAAA CUUGUA     36

( 2 ) INFORMATION FOR SEQ ID NO: 191:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 191:

GGGCAAACUG AUGAGGCCGA AAGGCCGAAA UCACUA    36

( 2 ) INFORMATION FOR SEQ ID NO: 192:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 192:

UAGGGCACUG AUGAGGCCGA AAGGCCGAAA UAUCAC    36

( 2 ) INFORMATION FOR SEQ ID NO: 193:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 193:

UUAGGGCCUG AUGAGGCCGA AAGGCCGAAA AUAUCA    36

( 2 ) INFORMATION FOR SEQ ID NO: 194:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 194:

UUAUUAUCUG AUGAGGCCGA AAGGCCGAAA GGGCAA    36

( 2 ) INFORMATION FOR SEQ ID NO: 195:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 195:

AUAUUAUCUG AUGAGGCCGA AAGGCCGAAA UUAGGG    36

( 2 ) INFORMATION FOR SEQ ID NO: 196:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 196:

ACAAUAUCUG AUGAGGCCGA AAGGCCGAAA UUAUUA    36

( 2 ) INFORMATION FOR SEQ ID NO: 197:

( i ) SEQUENCE CHARACTERISTICS:
      ( A ) LENGTH: 36 base pairs ( B ) TYPE: nucleic acid
        ( C ) STRANDEDNESS: single
        ( D ) TOPOLOGY: linear ( x i ) SEQUENCE DESCRIPTION: SEQ ID NO: 197:

ACUACAACUG AUGAGGCCGA AAGGCCGAAA UUAUUA    36

( 2 ) INFORMATION FOR SEQ ID NO: 198:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 198:

UUACUACCUG AUGAGGCCGA AAGGCCGAAA UAUUAU    36

( 2 ) INFORMATION FOR SEQ ID NO: 199:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 199:

AUUUUACCUG AUGAGGCCGA AAGGCCGAAA CAAUAU    36

( 2 ) INFORMATION FOR SEQ ID NO: 200:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 200:

UGGAUUUCUG AUGAGGCCGA AAGGCCGAAA CUACAA    36

( 2 ) INFORMATION FOR SEQ ID NO: 201:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 201:

GAAAUUGCUG AUGAGGCCGA AAGGCCGAAA UUUUAC    36

( 2 ) INFORMATION FOR SEQ ID NO: 202:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 202:

GUUGUGACUG AUGAGGCCGA AAGGCCGAAA UUGGAU    36

( 2 ) INFORMATION FOR SEQ ID NO: 203:

( i ) SEQUENCE CHARACTERISTICS:
        ( A ) LENGTH: 36 base pairs
        ( B ) TYPE: nucleic acid
        ( C ) STRANDEDNESS: single ( D ) TOPOLOGY: linear ( x i ) SEQUENCE DESCRIPTION: SEQ ID NO: 203:

UGUUGUGCUG AUGAGGCCGA AAGGCCGAAA AUUGGA 36

( 2 ) INFORMATION FOR SEQ ID NO: 204:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 204:

UUGUUGUCUG AUGAGGCCGA AAGGCCGAAA AAUUGG 36

( 2 ) INFORMATION FOR SEQ ID NO: 205:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 205:

UUUGUAGCUG AUGAGGCCGA AAGGCCGAAA CUGGCA 36

( 2 ) INFORMATION FOR SEQ ID NO: 206:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 206:

CAUUUUGCUG AUGAGGCCGA AAGGCCGAAA GUACUG 36

( 2 ) INFORMATION FOR SEQ ID NO: 207:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 207:

CAUAUAUCUG AUGAGGCCGA AAGGCCGAAA CCUCCA 36

( 2 ) INFORMATION FOR SEQ ID NO: 208:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 208:

CCAUAUACUG AUGAGGCCGA AAGGCCGAAA ACCUCC 36

( 2 ) INFORMATION FOR SEQ ID NO: 209:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 209:

UCCCAUACUG AUGAGGCCGA AAGGCCGAAA UAACCU                                36

( 2 ) INFORMATION FOR SEQ ID NO: 210:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 210:

UUUCCCACUG AUGAGGCCGA AAGGCCGAAA UAUAAC                                36

( 2 ) INFORMATION FOR SEQ ID NO: 211:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 211:

AUGUGUUCUG AUGAGGCCGA AAGGCCGAAA UUCCAU                                36

( 2 ) INFORMATION FOR SEQ ID NO: 212:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 212:

AAUGUGUCUG AUGAGGCCGA AAGGCCGAAA AUUCCA                                36

( 2 ) INFORMATION FOR SEQ ID NO: 213:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 213:

UGAGAGCCUG AUGAGGCCGA AAGGCCGAAA UGUGUU                                36

( 2 ) INFORMATION FOR SEQ ID NO: 214:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 214:

AGGUUGACUG AUGAGGCCGA AAGGCCGAAA GCAAUG                                36

( 2 ) INFORMATION FOR SEQ ID NO: 215:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 215:

```
UUAGGUUCUG AUGAGGCCGA AAGGCCGAAA GAGCAA                                    36
```

( 2 ) INFORMATION FOR SEQ ID NO: 216:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 216:

```
AGACCAUCUG AUGAGGCCGA AAGGCCGAAA GGUUGA                                    36
```

( 2 ) INFORMATION FOR SEQ ID NO: 217:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 217:

```
UCUAGUACUG AUGAGGCCGA AAGGCCGAAA CCAUUA                                    36
```

( 2 ) INFORMATION FOR SEQ ID NO: 218:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 218:

```
CAUCUAGCUG AUGAGGCCGA AAGGCCGAAA GACCAU                                    36
```

( 2 ) INFORMATION FOR SEQ ID NO: 219:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 219:

```
UGUCAUCCUG AUGAGGCCGA AAGGCCGAAA GUAGAC                                    36
```

( 2 ) INFORMATION FOR SEQ ID NO: 220:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 220:

```
AUUUCACCUG AUGAGGCCGA AAGGCCGAAA UUGUCA                                    36
```

( 2 ) INFORMATION FOR SEQ ID NO: 221:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 221:

```
AGAAUUUCUG AUGAGGCCGA AAGGCCGAAA UUUCAC                                    36
```

( 2 ) INFORMATION FOR SEQ ID NO: 222:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 222:

GAGAAUUCUG AUGAGGCCGA AAGGCCGAAA AUUUCA      36

( 2 ) INFORMATION FOR SEQ ID NO: 223:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 223:

UUUGGAGCUG AUGAGGCCGA AAGGCCGAAA UUUAAU      36

( 2 ) INFORMATION FOR SEQ ID NO: 224:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 224:

UUUUGGACUG AUGAGGCCGA AAGGCCGAAA AUUUAA      36

( 2 ) INFORMATION FOR SEQ ID NO: 225:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 225:

UUUUUUGCUG AUGAGGCCGA AAGGCCGAAA GAAUUU      36

( 2 ) INFORMATION FOR SEQ ID NO: 226:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 226:

AAUCACUCUG AUGAGGCCGA AAGGCCGAAA GUUUUU      36

( 2 ) INFORMATION FOR SEQ ID NO: 227:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 227:

AUUGUUGCUG AUGAGGCCGA AAGGCCGAAA UCACUU      36

( 2 ) INFORMATION FOR SEQ ID NO: 228:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 228:

CAUUGUUCUG AUGAGGCCGA AAGGCCGAAA AUCACU      36

( 2 ) INFORMATION FOR SEQ ID NO: 229:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 229:

UUCAUAUCUG AUGAGGCCGA AAGGCCGAAA UUGGUC      36

( 2 ) INFORMATION FOR SEQ ID NO: 230:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 230:

AUUCAUACUG AUGAGGCCGA AAGGCCGAAA AUUGGU      36

( 2 ) INFORMATION FOR SEQ ID NO: 231:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 231:

UGAUUCACUG AUGAGGCCGA AAGGCCGAAA UAAUUG      36

( 2 ) INFORMATION FOR SEQ ID NO: 232:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 232:

GAUAAUUCUG AUGAGGCCGA AAGGCCGAAA UUCAUA      36

( 2 ) INFORMATION FOR SEQ ID NO: 233:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 233:

UUCAGAUCUG AUGAGGCCGA AAGGCCGAAA UUGAUU      36

( 2 ) INFORMATION FOR SEQ ID NO: 234:

( i ) SEQUENCE CHARACTERISTICS:

(A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 234:

AUUCAGACUG AUGAGGCCGA AAGGCCGAAA AUUGAU 36

(2) INFORMATION FOR SEQ ID NO: 235:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 235:

UAAUUCACUG AUGAGGCCGA AAGGCCGAAA UAAUUG 36

(2) INFORMATION FOR SEQ ID NO: 236:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 236:

UCCAAGUCUG AUGAGGCCGA AAGGCCGAAA UUCAGA 36

(2) INFORMATION FOR SEQ ID NO: 237:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 237:

AUCCAAGCUG AUGAGGCCGA AAGGCCGAAA AUUCAG 36

(2) INFORMATION FOR SEQ ID NO: 238:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 238:

CAAAUCCCUG AUGAGGCCGA AAGGCCGAAA GUAAUU 36

(2) INFORMATION FOR SEQ ID NO: 239:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 239:

AAGAUCACUG AUGAGGCCGA AAGGCCGAAA UCCAAG 36

(2) INFORMATION FOR SEQ ID NO: 240:

(i) SEQUENCE CHARACTERISTICS:
        (A) LENGTH: 36 base pairs
        (B) TYPE: nucleic acid ( C ) STRANDEDNESS: single
( D ) TOPOLOGY: linear ( x i ) SEQUENCE DESCRIPTION: SEQ ID NO: 240:

UAAGAUCCUG AUGAGGCCGA AAGGCCGAAA AUCCAA    36

( 2 ) INFORMATION FOR SEQ ID NO: 241:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 241:

GGAUUAACUG AUGAGGCCGA AAGGCCGAAA UCAAAU    36

( 2 ) INFORMATION FOR SEQ ID NO: 242:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 242:

AUGGAUUCUG AUGAGGCCGA AAGGCCGAAA GAUCAA    36

( 2 ) INFORMATION FOR SEQ ID NO: 243:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 243:

UAUGGAUCUG AUGAGGCCGA AAGGCCGAAA AGAUCA    36

( 2 ) INFORMATION FOR SEQ ID NO: 244:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 244:

AUUUAUGCUG AUGAGGCCGA AAGGCCGAAA UUAAGA    36

( 2 ) INFORMATION FOR SEQ ID NO: 245:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 245:

UAUAAUUCUG AUGAGGCCGA AAGGCCGAAA UGGAUU    36

( 2 ) INFORMATION FOR SEQ ID NO: 246:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 246:

UAAUUAUCUG AUGAGGCCGA AAGGCCGAAA UUUAUG  36

( 2 ) INFORMATION FOR SEQ ID NO: 247:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 247:

UUAAUUACUG AUGAGGCCGA AAGGCCGAAA AUUUAU  36

( 2 ) INFORMATION FOR SEQ ID NO: 248:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 248:

UAUUAAUCUG AUGAGGCCGA AAGGCCGAAA UAAUUU  36

( 2 ) INFORMATION FOR SEQ ID NO: 249:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 249:

UGAUAUUCUG AUGAGGCCGA AAGGCCGAAA UUAUAA  36

( 2 ) INFORMATION FOR SEQ ID NO: 250:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 250:

UUGAUAUCUG AUGAGGCCGA AAGGCCGAAA AUUAUA  36

( 2 ) INFORMATION FOR SEQ ID NO: 251:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 251:

UAGUUGACUG AUGAGGCCGA AAGGCCGAAA UUAAUU  36

( 2 ) INFORMATION FOR SEQ ID NO: 252:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 252:

GCUAGUUCUG AUGAGGCCGA AAGGCCGAAA UAUUAA    36

( 2 ) INFORMATION FOR SEQ ID NO: 253:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 253:

GAUUUGCCUG AUGAGGCCGA AAGGCCGAAA GUUGAU    36

( 2 ) INFORMATION FOR SEQ ID NO: 254:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 254:

UGACAUUCUG AUGAGGCCGA AAGGCCGAAA UUUGCU    36

( 2 ) INFORMATION FOR SEQ ID NO: 255:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 255:

UGUUAGUCUG AUGAGGCCGA AAGGCCGAAA CAUUGA    36

( 2 ) INFORMATION FOR SEQ ID NO: 256:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 256:

AUGGUGUCUG AUGAGGCCGA AAGGCCGAAA GUGACA    36

( 2 ) INFORMATION FOR SEQ ID NO: 257:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 257:

AUUAACUCUG AUGAGGCCGA AAGGCCGAAA UGGUGU    36

( 2 ) INFORMATION FOR SEQ ID NO: 258:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 258:

UAUUAACCUG AUGAGGCCGA AAGGCCGAAA AUGGUG    36

( 2 ) INFORMATION FOR SEQ ID NO: 259:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 259:

UUAUAUUCUG AUGAGGCCGA AAGGCCGAAA CUAAUG    36

( 2 ) INFORMATION FOR SEQ ID NO: 260:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 260:

UUUAUAUCUG AUGAGGCCGA AAGGCCGAAA ACUAAU    36

( 2 ) INFORMATION FOR SEQ ID NO: 261:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 261:

GGCAAAUAAA UCAAU    15

( 2 ) INFORMATION FOR SEQ ID NO: 262:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 262:

AAUAAAUCAA UUCAG    15

( 2 ) INFORMATION FOR SEQ ID NO: 263:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 263:

AAUCAAUUCA GCCAA    15

( 2 ) INFORMATION FOR SEQ ID NO: 264:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 264:

AUCAAUUCAG CCAAC    15

( 2 ) INFORMATION FOR SEQ ID NO: 265:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 265:

CAAUGAUAAU ACACC      15

( 2 ) INFORMATION FOR SEQ ID NO: 266:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 266:

UGAUAAUACA CCACA      15

( 2 ) INFORMATION FOR SEQ ID NO: 267:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 267:

UGAUGAUCAC AGACA      15

( 2 ) INFORMATION FOR SEQ ID NO: 268:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 268:

AGACCGUUGU CACUU      15

( 2 ) INFORMATION FOR SEQ ID NO: 269:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 269:

CCGUUGUCAC UUGAG      15

( 2 ) INFORMATION FOR SEQ ID NO: 270:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 270:

UGUCACUUGA GACCA      15

( 2 ) INFORMATION FOR SEQ ID NO: 271:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 271:

AGACCAUAAU AACAU    15

( 2 ) INFORMATION FOR SEQ ID NO: 272:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 272:

CCAUAAUAAC AUCAC    15

( 2 ) INFORMATION FOR SEQ ID NO: 273:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 273:

AUAACAUCAC UAACC    15

( 2 ) INFORMATION FOR SEQ ID NO: 274:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 274:

CAUCACUAAC CAGAG    15

( 2 ) INFORMATION FOR SEQ ID NO: 275:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 275:

GAGACAUCAU AACAC    15

( 2 ) INFORMATION FOR SEQ ID NO: 276:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 276:

ACAUCAUAAC ACACA    15

( 2 ) INFORMATION FOR SEQ ID NO: 277:

( i ) SEQUENCE CHARACTERISTICS:
    ( A ) LENGTH: 15 base pairs ( B ) TYPE: nucleic acid
( C ) STRANDEDNESS: single
( D ) TOPOLOGY: linear ( x i ) SEQUENCE DESCRIPTION: SEQ ID NO: 277:

CACAAAUUUA UAUAC 15

( 2 ) INFORMATION FOR SEQ ID NO: 278:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 278:

ACAAAUUUAU AUACU 15

( 2 ) INFORMATION FOR SEQ ID NO: 279:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 279:

CAAAUUUAUA UACUU 15

( 2 ) INFORMATION FOR SEQ ID NO: 280:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 280:

AAUUUAUAUA CUUGA 15

( 2 ) INFORMATION FOR SEQ ID NO: 281:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 281:

UUUAUAUACU UGAUA 15

( 2 ) INFORMATION FOR SEQ ID NO: 282:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 282:

AUAUACUUGA UAAAU 15

( 2 ) INFORMATION FOR SEQ ID NO: 283:

( i ) SEQUENCE CHARACTERISTICS:
( A ) LENGTH: 15 base pairs
( B ) TYPE: nucleic acid
( C ) STRANDEDNESS: single ( D ) TOPOLOGY: linear ( x i ) SEQUENCE DESCRIPTION: SEQ ID NO: 283:

ACUUGAUAAA UCAUG    15

( 2 ) INFORMATION FOR SEQ ID NO: 284:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 284:

GAUAAAUCAU GAAUG    15

( 2 ) INFORMATION FOR SEQ ID NO: 285:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 285:

AAUGCAUAGU GAGAA    15

( 2 ) INFORMATION FOR SEQ ID NO: 286:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 286:

GAAACUUGA UGAAA    15

( 2 ) INFORMATION FOR SEQ ID NO: 287:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 287:

GCCACAUUUA CAUUC    15

( 2 ) INFORMATION FOR SEQ ID NO: 288:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 288:

CCACAUUUAC AUUCC    15

( 2 ) INFORMATION FOR SEQ ID NO: 289:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 289:

CACAUUUACA UUCCU                                                                                          15

( 2 ) INFORMATION FOR SEQ ID NO: 290:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 290:

UUUACAUUCC UGGUC                                                                                          15

( 2 ) INFORMATION FOR SEQ ID NO: 291:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 291:

UUACAUUCCU GGUCA                                                                                          15

( 2 ) INFORMATION FOR SEQ ID NO: 292:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 292:

UCCUGGUCAA CUAUG                                                                                          15

( 2 ) INFORMATION FOR SEQ ID NO: 293:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 293:

GUCAACUAUG AAAUG                                                                                          15

( 2 ) INFORMATION FOR SEQ ID NO: 294:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 294:

UGAAACUAUU ACACA                                                                                          15

( 2 ) INFORMATION FOR SEQ ID NO: 295:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 295:

AAACUAUUAC ACAAA 15

( 2 ) INFORMATION FOR SEQ ID NO: 296:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 296:

AACUAUUACA CAAAG 15

( 2 ) INFORMATION FOR SEQ ID NO: 297:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 297:

ACAAAGUAGG AAGCA 15

( 2 ) INFORMATION FOR SEQ ID NO: 298:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 298:

AAGCACUAAA UAUAA 15

( 2 ) INFORMATION FOR SEQ ID NO: 299:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 299:

ACUAAAUAUA AAAAA 15

( 2 ) INFORMATION FOR SEQ ID NO: 300:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 300:

UAAAUAUAAA AAAUA 15

( 2 ) INFORMATION FOR SEQ ID NO: 301:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 301:

AAAAAUAUA CUGAA 15

( 2 ) INFORMATION FOR SEQ ID NO: 302:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 302:

AAAAUAUACU GAAUA  15

( 2 ) INFORMATION FOR SEQ ID NO: 303:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 303:

ACUGAAUACA ACACA  15

( 2 ) INFORMATION FOR SEQ ID NO: 304:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 304:

ACAAAUAUG GCACU  15

( 2 ) INFORMATION FOR SEQ ID NO: 305:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 305:

UGGCACUUUC CCUAU  15

( 2 ) INFORMATION FOR SEQ ID NO: 306:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 306:

GGCACUUUCC CUAUG  15

( 2 ) INFORMATION FOR SEQ ID NO: 307:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 307:

GCACUUUCCC UAUGC  15

( 2 ) INFORMATION FOR SEQ ID NO: 308:

( i ) SEQUENCE CHARACTERISTICS:
   ( A ) LENGTH: 15 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 308:

UUUCCCUAUG CCAAU    15

( 2 ) INFORMATION FOR SEQ ID NO: 309:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 309:

UGCCAAUAUU CAUCA    15

( 2 ) INFORMATION FOR SEQ ID NO: 310:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 310:

CCAAUAUUCA UCAAU    15

( 2 ) INFORMATION FOR SEQ ID NO: 311:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 311:

CAAUAUUCAU CAAUC    15

( 2 ) INFORMATION FOR SEQ ID NO: 312:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 312:

UAUUCAUCAA UCAUG    15

( 2 ) INFORMATION FOR SEQ ID NO: 313:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 313:

CAUCAAUCAU GAUGG    15

( 2 ) INFORMATION FOR SEQ ID NO: 314:

( i ) SEQUENCE CHARACTERISTICS:

-continued (A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 314:

GAUGGGUUCU UAGAA                                      15

(2) INFORMATION FOR SEQ ID NO: 315:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 315:

AUGGGUUCUU AGAAU                                      15

(2) INFORMATION FOR SEQ ID NO: 316:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 316:

GGGUUCUUAG AAUGC                                      15

(2) INFORMATION FOR SEQ ID NO: 317:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 317:

GGUUCUUAGA AUGCA                                      15

(2) INFORMATION FOR SEQ ID NO: 318:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 318:

AAUGCAUUGG CAUUA                                      15

(2) INFORMATION FOR SEQ ID NO: 319:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 319:

UUGGCAUUAA GCCUA                                      15

(2) INFORMATION FOR SEQ ID NO: 320:

(i) SEQUENCE CHARACTERISTICS:
(A) LENGTH: 15 base pairs
(B) TYPE: nucleic acid (C) STRANDEDNESS: single
                (D) TOPOLOGY: linear (xi) SEQUENCE DESCRIPTION: SEQ ID NO: 320:

UGGCAUUAAG CCUAC               15

(2) INFORMATION FOR SEQ ID NO: 321:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO: 321:

UAAGCCUACA AAGCA               15

(2) INFORMATION FOR SEQ ID NO: 322:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO: 322:

AAAGCAUACU CCCAU               15

(2) INFORMATION FOR SEQ ID NO: 323:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO: 323:

GCAUACUCCC AUAAU               15

(2) INFORMATION FOR SEQ ID NO: 324:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO: 324:

CUCCCAUAAU AUACA               15

(2) INFORMATION FOR SEQ ID NO: 325:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO: 325:

CCAUAAUAUA CAAGU               15

(2) INFORMATION FOR SEQ ID NO: 326:

(i) SEQUENCE CHARACTERISTICS:
                (A) LENGTH: 15 base pairs
                (B) TYPE: nucleic acid
                (C) STRANDEDNESS: single
                (D) TOPOLOGY: linear ( x i ) SEQUENCE DESCRIPTION: SEQ ID NO: 326:

AUAAUAUACA AGUAU                                                                            15

( 2 ) INFORMATION FOR SEQ ID NO: 327:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 327:

UACAAGUAUG AUCUC                                                                            15

( 2 ) INFORMATION FOR SEQ ID NO: 328:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 328:

GUAUGAUCUC AAUCC                                                                            15

( 2 ) INFORMATION FOR SEQ ID NO: 329:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 329:

AUGAUCUCAA UCCAU                                                                            15

( 2 ) INFORMATION FOR SEQ ID NO: 330:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 330:

UCUCAAUCCA UAAAU                                                                            15

( 2 ) INFORMATION FOR SEQ ID NO: 331:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 331:

AAUCCAUAAA UUUCA                                                                            15

( 2 ) INFORMATION FOR SEQ ID NO: 332:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 332:

CAUAAAUUUC AACAC 15

( 2 ) INFORMATION FOR SEQ ID NO: 333:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 333:

AUAAAUUUCA ACACA 15

( 2 ) INFORMATION FOR SEQ ID NO: 334:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 334:

UAAAUUUCAA CACAA 15

( 2 ) INFORMATION FOR SEQ ID NO: 335:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 335:

ACACAAUAUU CACAC 15

( 2 ) INFORMATION FOR SEQ ID NO: 336:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 336:

ACAAUAUUCA CACAA 15

( 2 ) INFORMATION FOR SEQ ID NO: 337:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 337:

CAAUAUUCAC ACAAU 15

( 2 ) INFORMATION FOR SEQ ID NO: 338:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 338:

ACACAAUCUA AAACA 15

( 2 ) INFORMATION FOR SEQ ID NO: 339:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 339:

ACAAUCUAAA ACAAC              15

( 2 ) INFORMATION FOR SEQ ID NO: 340:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 340:

AACAACUCUA UGCAU              15

( 2 ) INFORMATION FOR SEQ ID NO: 341:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 341:

CAACUCUAUG CAUAA              15

( 2 ) INFORMATION FOR SEQ ID NO: 342:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 342:

UAUGCAUAAC UAUAC              15

( 2 ) INFORMATION FOR SEQ ID NO: 343:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 343:

CAUAACUAUA CUCCA              15

( 2 ) INFORMATION FOR SEQ ID NO: 344:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 344:

UAACUAUACU CCAUA              15

( 2 ) INFORMATION FOR SEQ ID NO: 345:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 345:

CUAUACUCCA UAGUC 15

( 2 ) INFORMATION FOR SEQ ID NO: 346:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 346:

ACUCCAUAGU CCAGA 15

( 2 ) INFORMATION FOR SEQ ID NO: 347:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 347:

CCAUAGUCCA GAUGG 15

( 2 ) INFORMATION FOR SEQ ID NO: 348:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 348:

UGAAAAUUAU AGUAA 15

( 2 ) INFORMATION FOR SEQ ID NO: 349:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 349:

GAAAAUUAUA GUAAU 15

( 2 ) INFORMATION FOR SEQ ID NO: 350:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 350:

AAAUUAUAGU AAUUU 15

( 2 ) INFORMATION FOR SEQ ID NO: 351:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 351:

UUAUAGUAAU UUAAA 15

( 2 ) INFORMATION FOR SEQ ID NO: 352:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 352:

AUUGAUUCUG AUGAGGCCGA AAGGCCGAAA UUUGCC 36

( 2 ) INFORMATION FOR SEQ ID NO: 353:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 353:

CUGAAUUCUG AUGAGGCCGA AAGGCCGAAA UUUAUU 36

( 2 ) INFORMATION FOR SEQ ID NO: 354:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 354:

UUGGCUGCUG AUGAGGCCGA AAGGCCGAAA UUGAUU 36

( 2 ) INFORMATION FOR SEQ ID NO: 355:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 355:

GUUGGCUCUG AUGAGGCCGA AAGGCCGAAA AUUGAU 36

( 2 ) INFORMATION FOR SEQ ID NO: 356:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 356:

GGUGUAUCUG AUGAGGCCGA AAGGCCGAAA UCAUUG 36

( 2 ) INFORMATION FOR SEQ ID NO: 357:

( i ) SEQUENCE CHARACTERISTICS:
  ( A ) LENGTH: 36 base pairs (B) TYPE: nucleic acid
            (C) STRANDEDNESS: single
            (D) TOPOLOGY: linear (xi) SEQUENCE DESCRIPTION: SEQ ID NO: 357:

UGUGGUGCUG AUGAGGCCGA AAGGCCGAAA UUAUCA                              36

(2) INFORMATION FOR SEQ ID NO: 358:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 358:

UGUCUGUCUG AUGAGGCCGA AAGGCCGAAA UCAUCA                              36

(2) INFORMATION FOR SEQ ID NO: 359:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 359:

AAGUGACCUG AUGAGGCCGA AAGGCCGAAA CGGUCU                              36

(2) INFORMATION FOR SEQ ID NO: 360:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 360:

CUCAAGUCUG AUGAGGCCGA AAGGCCGAAA CAACGG                              36

(2) INFORMATION FOR SEQ ID NO: 361:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 361:

UGGUCUCCUG AUGAGGCCGA AAGGCCGAAA GUGACA                              36

(2) INFORMATION FOR SEQ ID NO: 362:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 362:

AUGUUAUCUG AUGAGGCCGA AAGGCCGAAA UGGUCU                              36

(2) INFORMATION FOR SEQ ID NO: 363:

(i) SEQUENCE CHARACTERISTICS:
            (A) LENGTH: 36 base pairs
            (B) TYPE: nucleic acid
            (C) STRANDEDNESS: single ( D ) TOPOLOGY: linear ( x i ) SEQUENCE DESCRIPTION: SEQ ID NO: 363:

GUGAUGUCUG AUGAGGCCGA AAGGCCGAAA UUAUGG     36

( 2 ) INFORMATION FOR SEQ ID NO: 364:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 364:

GGUUAGUCUG AUGAGGCCGA AAGGCCGAAA UGUUAU     36

( 2 ) INFORMATION FOR SEQ ID NO: 365:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 365:

CUCUGGUCUG AUGAGGCCGA AAGGCCGAAA GUGAUG     36

( 2 ) INFORMATION FOR SEQ ID NO: 366:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 366:

GUGUUAUCUG AUGAGGCCGA AAGGCCGAAA UGUCUC     36

( 2 ) INFORMATION FOR SEQ ID NO: 367:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 367:

UGUGUGUCUG AUGAGGCCGA AAGGCCGAAA UGAUGU     36

( 2 ) INFORMATION FOR SEQ ID NO: 368:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 368:

GUAUAUACUG AUGAGGCCGA AAGGCCGAAA UUUGUG     36

( 2 ) INFORMATION FOR SEQ ID NO: 369:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 369:

AGUAUAUCUG AUGAGGCCGA AAGGCCGAAA AUUUGU    36

( 2 ) INFORMATION FOR SEQ ID NO: 370:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 370:

AAGUAUACUG AUGAGGCCGA AAGGCCGAAA AAUUUG    36

( 2 ) INFORMATION FOR SEQ ID NO: 371:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 371:

UCAAGUACUG AUGAGGCCGA AAGGCCGAAA UAAAUU    36

( 2 ) INFORMATION FOR SEQ ID NO: 372:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 372:

UAUCAAGCUG AUGAGGCCGA AAGGCCGAAA UAUAAA    36

( 2 ) INFORMATION FOR SEQ ID NO: 373:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 373:

AUUUAUCCUG AUGAGGCCGA AAGGCCGAAA GUAUAU    36

( 2 ) INFORMATION FOR SEQ ID NO: 374:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 374:

CAUGAUUCUG AUGAGGCCGA AAGGCCGAAA UCAAGU    36

( 2 ) INFORMATION FOR SEQ ID NO: 375:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 375:

```
         CAUUCAUCUG AUGAGGCCGA AAGGCCGAAA UUUAUC                                       36
```

( 2 ) INFORMATION FOR SEQ ID NO: 376:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 376:

```
         UUCUCACCUG AUGAGGCCGA AAGGCCGAAA UGCAUU                                       36
```

( 2 ) INFORMATION FOR SEQ ID NO: 377:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 377:

```
         UUUCAUCCUG AUGAGGCCGA AAGGCCGAAA GUUUUC                                       36
```

( 2 ) INFORMATION FOR SEQ ID NO: 378:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 378:

```
         GAAUGUACUG AUGAGGCCGA AAGGCCGAAA UGUGGC                                       36
```

( 2 ) INFORMATION FOR SEQ ID NO: 379:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 379:

```
         GGAAUGUCUG AUGAGGCCGA AAGGCCGAAA AUGUGG                                       36
```

( 2 ) INFORMATION FOR SEQ ID NO: 380:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 380:

```
         AGGAAUGCUG AUGAGGCCGA AAGGCCGAAA AAUGUG                                       36
```

( 2 ) INFORMATION FOR SEQ ID NO: 381:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 381:

```
         GACCAGGCUG AUGAGGCCGA AAGGCCGAAA UGUAAA                                       36
```

(2) INFORMATION FOR SEQ ID NO: 382:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (xi) SEQUENCE DESCRIPTION: SEQ ID NO: 382:

UGACCAGCUG AUGAGGCCGA AAGGCCGAAA AUGUAA     36

(2) INFORMATION FOR SEQ ID NO: 383:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (xi) SEQUENCE DESCRIPTION: SEQ ID NO: 383:

CAUAGUUCUG AUGAGGCCGA AAGGCCGAAA CCAGGA     36

(2) INFORMATION FOR SEQ ID NO: 384:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (xi) SEQUENCE DESCRIPTION: SEQ ID NO: 384:

CAUUUCACUG AUGAGGCCGA AAGGCCGAAA GUUGAC     36

(2) INFORMATION FOR SEQ ID NO: 385:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (xi) SEQUENCE DESCRIPTION: SEQ ID NO: 385:

UGUGUAACUG AUGAGGCCGA AAGGCCGAAA GUUUCA     36

(2) INFORMATION FOR SEQ ID NO: 386:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (xi) SEQUENCE DESCRIPTION: SEQ ID NO: 386:

UUUGUGUCUG AUGAGGCCGA AAGGCCGAAA UAGUUU     36

(2) INFORMATION FOR SEQ ID NO: 387:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (xi) SEQUENCE DESCRIPTION: SEQ ID NO: 387:

CUUUGUGCUG AUGAGGCCGA AAGGCCGAAA AUAGUU     36

(2) INFORMATION FOR SEQ ID NO: 388:

( i ) SEQUENCE CHARACTERISTICS:
 ( A ) LENGTH: 36 base pairs
 ( B ) TYPE: nucleic acid
 ( C ) STRANDEDNESS: single
 ( D ) TOPOLOGY: linear ( x i ) SEQUENCE DESCRIPTION: SEQ ID NO: 388:

UGCUUCCCUG AUGAGGCCGA AAGGCCGAAA CUUUGU  36

( 2 ) INFORMATION FOR SEQ ID NO: 389:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 389:

UUAUAUUCUG AUGAGGCCGA AAGGCCGAAA GUGCUU  36

( 2 ) INFORMATION FOR SEQ ID NO: 390:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 390:

UUUUUUACUG AUGAGGCCGA AAGGCCGAAA UUUAGU  36

( 2 ) INFORMATION FOR SEQ ID NO: 391:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 391:

UAUUUUUCUG AUGAGGCCGA AAGGCCGAAA UAUUUA  36

( 2 ) INFORMATION FOR SEQ ID NO: 392:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 392:

UUCAGUACUG AUGAGGCCGA AAGGCCGAAA UUUUUU  36

( 2 ) INFORMATION FOR SEQ ID NO: 393:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 393:

UAUUCAGCUG AUGAGGCCGA AAGGCCGAAA UAUUUU  36

( 2 ) INFORMATION FOR SEQ ID NO: 394:

( i ) SEQUENCE CHARACTERISTICS:

(A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 394:

UGUGUUGCUG AUGAGGCCGA AAGGCCGAAA UUCAGU        36

(2) INFORMATION FOR SEQ ID NO: 395:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 395:

AGUGCCACUG AUGAGGCCGA AAGGCCGAAA UUUUGU        36

(2) INFORMATION FOR SEQ ID NO: 396:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 396:

AUAGGGACUG AUGAGGCCGA AAGGCCGAAA GUGCCA        36

(2) INFORMATION FOR SEQ ID NO: 397:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 397:

CAUAGGGCUG AUGAGGCCGA AAGGCCGAAA AGUGCC        36

(2) INFORMATION FOR SEQ ID NO: 398:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 398:

GCAUAGGCUG AUGAGGCCGA AAGGCCGAAA AAGUGC        36

(2) INFORMATION FOR SEQ ID NO: 399:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 399:

AUUGGCACUG AUGAGGCCGA AAGGCCGAAA GGGAAA        36

(2) INFORMATION FOR SEQ ID NO: 400:

(i) SEQUENCE CHARACTERISTICS:
            (A) LENGTH: 36 base pairs
            (B) TYPE: nucleic acid ( C ) STRANDEDNESS: single
         ( D ) TOPOLOGY: linear ( x i ) SEQUENCE DESCRIPTION: SEQ ID NO: 400:

UGAUGAACUG AUGAGGCCGA AAGGCCGAAA UUGGCA 36

( 2 ) INFORMATION FOR SEQ ID NO: 401:

( i ) SEQUENCE CHARACTERISTICS:
         ( A ) LENGTH: 36 base pairs
         ( B ) TYPE: nucleic acid
         ( C ) STRANDEDNESS: single
         ( D ) TOPOLOGY: linear ( x i ) SEQUENCE DESCRIPTION: SEQ ID NO: 401:

AUUGAUGCUG AUGAGGCCGA AAGGCCGAAA UAUUGG 36

( 2 ) INFORMATION FOR SEQ ID NO: 402:

( i ) SEQUENCE CHARACTERISTICS:
         ( A ) LENGTH: 36 base pairs
         ( B ) TYPE: nucleic acid
         ( C ) STRANDEDNESS: single
         ( D ) TOPOLOGY: linear ( x i ) SEQUENCE DESCRIPTION: SEQ ID NO: 402:

GAUUGAUCUG AUGAGGCCGA AAGGCCGAAA AUAUUG 36

( 2 ) INFORMATION FOR SEQ ID NO: 403:

( i ) SEQUENCE CHARACTERISTICS:
         ( A ) LENGTH: 36 base pairs
         ( B ) TYPE: nucleic acid
         ( C ) STRANDEDNESS: single
         ( D ) TOPOLOGY: linear ( x i ) SEQUENCE DESCRIPTION: SEQ ID NO: 403:

CAUGAUUCUG AUGAGGCCGA AAGGCCGAAA UGAAUA 36

( 2 ) INFORMATION FOR SEQ ID NO: 404:

( i ) SEQUENCE CHARACTERISTICS:
         ( A ) LENGTH: 36 base pairs
         ( B ) TYPE: nucleic acid
         ( C ) STRANDEDNESS: single
         ( D ) TOPOLOGY: linear ( x i ) SEQUENCE DESCRIPTION: SEQ ID NO: 404:

CCAUCAUCUG AUGAGGCCGA AAGGCCGAAA UUGAUG 36

( 2 ) INFORMATION FOR SEQ ID NO: 405:

( i ) SEQUENCE CHARACTERISTICS:
         ( A ) LENGTH: 36 base pairs
         ( B ) TYPE: nucleic acid
         ( C ) STRANDEDNESS: single
         ( D ) TOPOLOGY: linear ( x i ) SEQUENCE DESCRIPTION: SEQ ID NO: 405:

UUCUAAGCUG AUGAGGCCGA AAGGCCGAAA CCCAUC 36

( 2 ) INFORMATION FOR SEQ ID NO: 406:

( i ) SEQUENCE CHARACTERISTICS:
         ( A ) LENGTH: 36 base pairs
         ( B ) TYPE: nucleic acid
         ( C ) STRANDEDNESS: single
         ( D ) TOPOLOGY: linear ( x i ) SEQUENCE DESCRIPTION: SEQ ID NO: 406:

AUUCUAACUG AUGAGGCCGA AAGGCCGAAA ACCCAU      36

( 2 ) INFORMATION FOR SEQ ID NO: 407:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 407:

GCAUUCUCUG AUGAGGCCGA AAGGCCGAAA GAACCC      36

( 2 ) INFORMATION FOR SEQ ID NO: 408:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 408:

UGCAUUCCUG AUGAGGCCGA AAGGCCGAAA AGAACC      36

( 2 ) INFORMATION FOR SEQ ID NO: 409:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 409:

UAAUGCCCUG AUGAGGCCGA AAGGCCGAAA UGCAUU      36

( 2 ) INFORMATION FOR SEQ ID NO: 410:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 410:

UAGGCUUCUG AUGAGGCCGA AAGGCCGAAA UGCCAA      36

( 2 ) INFORMATION FOR SEQ ID NO: 411:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 411:

GUAGGCUCUG AUGAGGCCGA AAGGCCGAAA AUGCCA      36

( 2 ) INFORMATION FOR SEQ ID NO: 412:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 412:

```
UGCUUUGCUG AUGAGGCCGA AAGGCCGAAA GGCUUA                    36
```

( 2 ) INFORMATION FOR SEQ ID NO: 413:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 413:

```
AUGGGAGCUG AUGAGGCCGA AAGGCCGAAA UGCUUU                    36
```

( 2 ) INFORMATION FOR SEQ ID NO: 414:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 414:

```
AUUAUGGCUG AUGAGGCCGA AAGGCCGAAA GUAUGC                    36
```

( 2 ) INFORMATION FOR SEQ ID NO: 415:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 415:

```
UGUAUAUCUG AUGAGGCCGA AAGGCCGAAA UGGGAG                    36
```

( 2 ) INFORMATION FOR SEQ ID NO: 416:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 416:

```
ACUUGUACUG AUGAGGCCGA AAGGCCGAAA UUAUGG                    36
```

( 2 ) INFORMATION FOR SEQ ID NO: 417:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 417:

```
AUACUUGCUG AUGAGGCCGA AAGGCCGAAA UAUUAU                    36
```

( 2 ) INFORMATION FOR SEQ ID NO: 418:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 418:

```
GAGAUCACUG AUGAGGCCGA AAGGCCGAAA CUUGUA                    36
```

( 2 ) INFORMATION FOR SEQ ID NO: 419:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 419:

GGAUUGACUG AUGAGGCCGA AAGGCCGAAA UCAUAC       36

( 2 ) INFORMATION FOR SEQ ID NO: 420:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 420:

AUGGAUUCUG AUGAGGCCGA AAGGCCGAAA GAUCAU       36

( 2 ) INFORMATION FOR SEQ ID NO: 421:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 421:

AUUUAUGCUG AUGAGGCCGA AAGGCCGAAA UUGAGA       36

( 2 ) INFORMATION FOR SEQ ID NO: 422:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 422:

UGAAAUUCUG AUGAGGCCGA AAGGCCGAAA UGGAUU       36

( 2 ) INFORMATION FOR SEQ ID NO: 423:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 423:

GUGUUGACUG AUGAGGCCGA AAGGCCGAAA UUUAUG       36

( 2 ) INFORMATION FOR SEQ ID NO: 424:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 424:

UGUGUUGCUG AUGAGGCCGA AAGGCCGAAA AUUUAU       36

( 2 ) INFORMATION FOR SEQ ID NO: 425:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 425:

UUGUGUUCUG AUGAGGCCGA AAGGCCGAAA AAUUUA    36

( 2 ) INFORMATION FOR SEQ ID NO: 426:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 426:

GUGUGAACUG AUGAGGCCGA AAGGCCGAAA UUGUGU    36

( 2 ) INFORMATION FOR SEQ ID NO: 427:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 427:

UUGUGUGCUG AUGAGGCCGA AAGGCCGAAA UAUUGU    36

( 2 ) INFORMATION FOR SEQ ID NO: 428:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 428:

AUUGUGUCUG AUGAGGCCGA AAGGCCGAAA AUAUUG    36

( 2 ) INFORMATION FOR SEQ ID NO: 429:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 429:

UGUUUUACUG AUGAGGCCGA AAGGCCGAAA UUGUGU    36

( 2 ) INFORMATION FOR SEQ ID NO: 430:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 430:

GUUGUUUCUG AUGAGGCCGA AAGGCCGAAA GAUUGU    36

( 2 ) INFORMATION FOR SEQ ID NO: 431:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 431:

AUGCAUACUG AUGAGGCCGA AAGGCCGAAA GUUGUU                    36

( 2 ) INFORMATION FOR SEQ ID NO: 432:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 432:

UUAUGCACUG AUGAGGCCGA AAGGCCGAAA GAGUUG                    36

( 2 ) INFORMATION FOR SEQ ID NO: 433:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 433:

GUAUAGUCUG AUGAGGCCGA AAGGCCGAAA UGCAUA                    36

( 2 ) INFORMATION FOR SEQ ID NO: 434:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 434:

UGGAGUACUG AUGAGGCCGA AAGGCCGAAA GUUAUG                    36

( 2 ) INFORMATION FOR SEQ ID NO: 435:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 435:

UAUGGAGCUG AUGAGGCCGA AAGGCCGAAA UAGUUA                    36

( 2 ) INFORMATION FOR SEQ ID NO: 436:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 436:

GACUAUGCUG AUGAGGCCGA AAGGCCGAAA GUAUAG                    36

( 2 ) INFORMATION FOR SEQ ID NO: 437:

( i ) SEQUENCE CHARACTERISTICS:
    ( A ) LENGTH: 36 base pairs (B) TYPE: nucleic acid
(C) STRANDEDNESS: single
(D) TOPOLOGY: linear (xi) SEQUENCE DESCRIPTION: SEQ ID NO: 437:

UCUGGACCUG AUGAGGCCGA AAGGCCGAAA UGGAGU     36

(2) INFORMATION FOR SEQ ID NO: 438:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 438:

CCAUCUGCUG AUGAGGCCGA AAGGCCGAAA CUAUGG     36

(2) INFORMATION FOR SEQ ID NO: 439:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 439:

UUACUAUCUG AUGAGGCCGA AAGGCCGAAA UUUUCA     36

(2) INFORMATION FOR SEQ ID NO: 440:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 440:

AUUACUACUG AUGAGGCCGA AAGGCCGAAA AUUUUC     36

(2) INFORMATION FOR SEQ ID NO: 441:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 441:

AAAUUACCUG AUGAGGCCGA AAGGCCGAAA UAAUUU     36

(2) INFORMATION FOR SEQ ID NO: 442:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 442:

UUUAAAUCUG AUGAGGCCGA AAGGCCGAAA CUAUAA     36

(2) INFORMATION FOR SEQ ID NO: 443:

(i) SEQUENCE CHARACTERISTICS:
(A) LENGTH: 15 base pairs
(B) TYPE: nucleic acid
(C) STRANDEDNESS: single ( D ) TOPOLOGY: linear ( x i ) SEQUENCE DESCRIPTION: SEQ ID NO: 443:

GGCAAAUACA AAGAU 15

( 2 ) INFORMATION FOR SEQ ID NO: 444:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 444:

GAUGGCUCUU AGCAA 15

( 2 ) INFORMATION FOR SEQ ID NO: 445:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 445:

UGGCUCUUAG CAAAG 15

( 2 ) INFORMATION FOR SEQ ID NO: 446:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 446:

GGCUCUUAGC AAAGU 15

( 2 ) INFORMATION FOR SEQ ID NO: 447:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 447:

GCAAAGUCAA GUUGA 15

( 2 ) INFORMATION FOR SEQ ID NO: 448:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 448:

GUCAAGUUGA AUGAU 15

( 2 ) INFORMATION FOR SEQ ID NO: 449:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 449:

GAAUGAUACA CUCAA 15

( 2 ) INFORMATION FOR SEQ ID NO: 450:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 450:

AUACACUCAA CAAAG 15

( 2 ) INFORMATION FOR SEQ ID NO: 451:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 451:

CAAAGAUCAA CUUCU 15

( 2 ) INFORMATION FOR SEQ ID NO: 452:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 452:

AUCAACUUCU GUCAU 15

( 2 ) INFORMATION FOR SEQ ID NO: 453:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 453:

UCAACUUCUG UCAUC 15

( 2 ) INFORMATION FOR SEQ ID NO: 454:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 454:

CUUCUGUCAU CCAGC 15

( 2 ) INFORMATION FOR SEQ ID NO: 455:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 455:

```
CUGUCAUCCA GCAAA                                                                     15
```

(2) INFORMATION FOR SEQ ID NO: 456:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 456:

```
AGCAAAUACA CCAUC                                                                     15
```

(2) INFORMATION FOR SEQ ID NO: 457:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 457:

```
ACACCAUCCA ACGGA                                                                     15
```

(2) INFORMATION FOR SEQ ID NO: 458:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 458:

```
AGGAGAUAGU AUUGA                                                                     15
```

(2) INFORMATION FOR SEQ ID NO: 459:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 459:

```
AGAUAGUAUU GAUAC                                                                     15
```

(2) INFORMATION FOR SEQ ID NO: 460:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 460:

```
AUAGUAUUGA UACUC                                                                     15
```

(2) INFORMATION FOR SEQ ID NO: 461:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 461:

```
UAUUGAUACU CCUAA                                                                     15
```

( 2 ) INFORMATION FOR SEQ ID NO: 462:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 462:

UGAUACUCCU AAUUA      15

( 2 ) INFORMATION FOR SEQ ID NO: 463:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 463:

UACUCCUAAU UAUGA      15

( 2 ) INFORMATION FOR SEQ ID NO: 464:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 464:

UCCUAAUUAU GAUGU      15

( 2 ) INFORMATION FOR SEQ ID NO: 465:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 465:

CCUAAUUAUG AUGUG      15

( 2 ) INFORMATION FOR SEQ ID NO: 466:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 466:

AACACAUCAA UAAGU      15

( 2 ) INFORMATION FOR SEQ ID NO: 467:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 467:

CAUCAAUAAG UUAUG      15

( 2 ) INFORMATION FOR SEQ ID NO: 468:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 468:

AAUAAGUUAU GUGGC 15

( 2 ) INFORMATION FOR SEQ ID NO: 469:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 469:

AUAAGUUAUG UGGCA 15

( 2 ) INFORMATION FOR SEQ ID NO: 470:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 470:

GGCAUGUUAU UAAUC 15

( 2 ) INFORMATION FOR SEQ ID NO: 471:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 471:

GCAUGUUAUU AAUCA 15

( 2 ) INFORMATION FOR SEQ ID NO: 472:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 472:

AUGUUAUUAA UCACA 15

( 2 ) INFORMATION FOR SEQ ID NO: 473:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 473:

UGUUAUUAAU CACAG 15

( 2 ) INFORMATION FOR SEQ ID NO: 474:

( i ) SEQUENCE CHARACTERISTICS:

(A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO: 474:

UAUUAAUCAC AGAAG                                                                15

(2) INFORMATION FOR SEQ ID NO: 475:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO: 475:

AGAUGCUAAU CAUAA                                                                15

(2) INFORMATION FOR SEQ ID NO: 476:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO: 476:

UGCUAAUCAU AAAUU                                                                15

(2) INFORMATION FOR SEQ ID NO: 477:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO: 477:

UAAUCAUAAA UUCAC                                                                15

(2) INFORMATION FOR SEQ ID NO: 478:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO: 478:

CAUAAAUUCA CUGGG                                                                15

(2) INFORMATION FOR SEQ ID NO: 479:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO: 479:

AUAAAUUCAC UGGGU                                                                15

(2) INFORMATION FOR SEQ ID NO: 480:

(i) SEQUENCE CHARACTERISTICS:
                (A) LENGTH: 15 base pairs
                (B) TYPE: nucleic acid (C) STRANDEDNESS: single
        (D) TOPOLOGY: linear (xi) SEQUENCE DESCRIPTION: SEQ ID NO: 480:

ACUGGGUUAA UAGGU                                                                            15

(2) INFORMATION FOR SEQ ID NO: 481:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 481:

CUGGGUUAAU AGGUA                                                                            15

(2) INFORMATION FOR SEQ ID NO: 482:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 482:

GGUUAAUAGG UAUGU                                                                            15

(2) INFORMATION FOR SEQ ID NO: 483:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 483:

AAUAGGUAUG UUAUA                                                                            15

(2) INFORMATION FOR SEQ ID NO: 484:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 484:

GGUAUGUUAU AUGCG                                                                            15

(2) INFORMATION FOR SEQ ID NO: 485:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 485:

GUAUGUUAUA UGCGA                                                                            15

(2) INFORMATION FOR SEQ ID NO: 486:

(i) SEQUENCE CHARACTERISTICS:
        (A) LENGTH: 15 base pairs
        (B) TYPE: nucleic acid
        (C) STRANDEDNESS: single
        (D) TOPOLOGY: linear ( x i ) SEQUENCE DESCRIPTION: SEQ ID NO: 486:

AUGUUAUAUG CGAUG                                                                  15

( 2 ) INFORMATION FOR SEQ ID NO: 487:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 487:

GCGAUGUCUA GGUUA                                                                  15

( 2 ) INFORMATION FOR SEQ ID NO: 488:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 488:

GAUGUCUAGG UUAGG                                                                  15

( 2 ) INFORMATION FOR SEQ ID NO: 489:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 489:

UCUAGGUUAG GAAGA                                                                  15

( 2 ) INFORMATION FOR SEQ ID NO: 490:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 490:

CUAGGUUAGG AAGAG                                                                  15

( 2 ) INFORMATION FOR SEQ ID NO: 491:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 491:

ACACCAUAAA AAUAC                                                                  15

( 2 ) INFORMATION FOR SEQ ID NO: 492:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 492:

UAAAAAUACU CAGAG                                                                15

( 2 ) INFORMATION FOR SEQ ID NO: 493:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 493:

AAAUACUCAG AGAUG                                                                15

( 2 ) INFORMATION FOR SEQ ID NO: 494:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 494:

GCGGGAUAUC AUGUA                                                                15

( 2 ) INFORMATION FOR SEQ ID NO: 495:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 495:

GGGAUAUCAU GUAAA                                                                15

( 2 ) INFORMATION FOR SEQ ID NO: 496:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 496:

AUCAUGUAAA AGCAA                                                                15

( 2 ) INFORMATION FOR SEQ ID NO: 497:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 497:

AUGGAGUAGA UGUAA                                                                15

( 2 ) INFORMATION FOR SEQ ID NO: 498:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 498:

UAGAUGUAAC AACAC                                                                15

( 2 ) INFORMATION FOR SEQ ID NO: 499:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 499:

AACACAUCGU CAAGA         15

( 2 ) INFORMATION FOR SEQ ID NO: 500:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 500:

ACAUCGUCAA GACAU         15

( 2 ) INFORMATION FOR SEQ ID NO: 501:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 501:

AAGACAUUAA UGGAA         15

( 2 ) INFORMATION FOR SEQ ID NO: 502:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 502:

AGACAUUAAU GGAAA         15

( 2 ) INFORMATION FOR SEQ ID NO: 503:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 503:

AUGAAAUUUG AAGUG         15

( 2 ) INFORMATION FOR SEQ ID NO: 504:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 504:

UGAAAUUUGA AGUGU         15

( 2 ) INFORMATION FOR SEQ ID NO: 505:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 505:

GAAGUGUUAA CAUUG  15

( 2 ) INFORMATION FOR SEQ ID NO: 506:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 506:

AAGUGUUAAC AUUGG  15

( 2 ) INFORMATION FOR SEQ ID NO: 507:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 507:

UUAACAUUGG CAAGC  15

( 2 ) INFORMATION FOR SEQ ID NO: 508:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 508:

GCAAGCUUAA CAACU  15

( 2 ) INFORMATION FOR SEQ ID NO: 509:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 509:

CAAGCUUAAC AACUG  15

( 2 ) INFORMATION FOR SEQ ID NO: 510:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 510:

CUGAAAUUCA AAUCA  15

( 2 ) INFORMATION FOR SEQ ID NO: 511:

```
        ( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 511:

UGAAAUUCAA  AUCAA                                                                        15

( 2 ) INFORMATION FOR SEQ ID NO: 512:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 512:

UUCAAAUCAA  CAUUG                                                                        15

( 2 ) INFORMATION FOR SEQ ID NO: 513:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 513:

UCAACAUUGA  GAUAG                                                                        15

( 2 ) INFORMATION FOR SEQ ID NO: 514:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 514:

UUGAGAUAGA  AUCUA                                                                        15

( 2 ) INFORMATION FOR SEQ ID NO: 515:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 515:

AUAGAAUCUA  GAAAA                                                                        15

( 2 ) INFORMATION FOR SEQ ID NO: 516:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 516:

AGAAUCUAGA  AAAUC                                                                        15

( 2 ) INFORMATION FOR SEQ ID NO: 517:

( i ) SEQUENCE CHARACTERISTICS:
                ( A ) LENGTH: 15 base pairs
```

-continued (B) TYPE: nucleic acid
(C) STRANDEDNESS: single
(D) TOPOLOGY: linear (xi) SEQUENCE DESCRIPTION: SEQ ID NO: 517:

AGAAAAUCCU ACAAA     15

(2) INFORMATION FOR SEQ ID NO: 518:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 518:

AAAUCCUACA AAAAA     15

(2) INFORMATION FOR SEQ ID NO: 519:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 519:

AAAUGCUAAA AGAAA     15

(2) INFORMATION FOR SEQ ID NO: 520:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 520:

GAGAGGUAGC UCCAG     15

(2) INFORMATION FOR SEQ ID NO: 521:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 521:

GGUAGCUCCA GAAUA     15

(2) INFORMATION FOR SEQ ID NO: 522:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 522:

CCAGAAUACA GGCAU     15

(2) INFORMATION FOR SEQ ID NO: 523:

(i) SEQUENCE CHARACTERISTICS:
(A) LENGTH: 15 base pairs
(B) TYPE: nucleic acid
(C) STRANDEDNESS: single (D) TOPOLOGY: linear (xi) SEQUENCE DESCRIPTION: SEQ ID NO: 523:

CAUGACUCUC CUGAU                                                                    15

(2) INFORMATION FOR SEQ ID NO: 524:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO: 524:

UGACUCUCCU GAUUG                                                                    15

(2) INFORMATION FOR SEQ ID NO: 525:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO: 525:

UCCUGAUUGU GGGAU                                                                    15

(2) INFORMATION FOR SEQ ID NO: 526:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO: 526:

GGAUGAUAAU AUUAU                                                                    15

(2) INFORMATION FOR SEQ ID NO: 527:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO: 527:

UGAUAAUAUU AUGUA                                                                    15

(2) INFORMATION FOR SEQ ID NO: 528:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO: 528:

AUAAUAUUAU GUAUA                                                                    15

(2) INFORMATION FOR SEQ ID NO: 529:

(i) SEQUENCE CHARACTERISTICS:
                (A) LENGTH: 15 base pairs
                (B) TYPE: nucleic acid
                (C) STRANDEDNESS: single
                (D) TOPOLOGY: linear ( x i ) SEQUENCE DESCRIPTION: SEQ ID NO: 529:

UAAUAUUAUG UAUAG     15

( 2 ) INFORMATION FOR SEQ ID NO: 530:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 530:

AUUAUGUAUA GCAGC     15

( 2 ) INFORMATION FOR SEQ ID NO: 531:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 531:

UAUGUAUAGC AGCAU     15

( 2 ) INFORMATION FOR SEQ ID NO: 532:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 532:

GCAGCAUUAG UAAUA     15

( 2 ) INFORMATION FOR SEQ ID NO: 533:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 533:

CAGCAUUAGU AAUAA     15

( 2 ) INFORMATION FOR SEQ ID NO: 534:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 534:

CAUUAGUAAU AACUA     15

( 2 ) INFORMATION FOR SEQ ID NO: 535:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 535:

-continued

UAGUAAUAAC UAAAU　　　　　　　　　　　　　　　　　　　　　　　　　　　　　15

( 2 ) INFORMATION FOR SEQ ID NO: 536:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 536:

AAUAACUAAA UUAGC　　　　　　　　　　　　　　　　　　　　　　　　　　　　　15

( 2 ) INFORMATION FOR SEQ ID NO: 537:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 537:

ACUAAAUUAG CAGCA　　　　　　　　　　　　　　　　　　　　　　　　　　　　　15

( 2 ) INFORMATION FOR SEQ ID NO: 538:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 538:

CUAAAUUAGC AGCAG　　　　　　　　　　　　　　　　　　　　　　　　　　　　　15

( 2 ) INFORMATION FOR SEQ ID NO: 539:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 539:

GACAGAUCUG GUCUU　　　　　　　　　　　　　　　　　　　　　　　　　　　　　15

( 2 ) INFORMATION FOR SEQ ID NO: 540:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 540:

AUCUGGUCUU ACAGC　　　　　　　　　　　　　　　　　　　　　　　　　　　　　15

( 2 ) INFORMATION FOR SEQ ID NO: 541:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 541:

CUGGUCUUAC AGCCG　　　　　　　　　　　　　　　　　　　　　　　　　　　　　15

( 2 ) INFORMATION FOR SEQ ID NO: 542:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 542:

UGGUCUUACA GCCGU        15

( 2 ) INFORMATION FOR SEQ ID NO: 543:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 543:

CCGUGAUUAG GAGAG        15

( 2 ) INFORMATION FOR SEQ ID NO: 544:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 544:

CGUGAUUAGG AGAGC        15

( 2 ) INFORMATION FOR SEQ ID NO: 545:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 545:

GAGAGCUAAU AAUGU        15

( 2 ) INFORMATION FOR SEQ ID NO: 546:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 546:

AGCUAAUAAU GUCCU        15

( 2 ) INFORMATION FOR SEQ ID NO: 547:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 547:

AUAAUGUCCU AAAAA        15

( 2 ) INFORMATION FOR SEQ ID NO: 548:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 548:

AUGUCCUAAA AAAUG 15

( 2 ) INFORMATION FOR SEQ ID NO: 549:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 549:

GAAACGUUAC AAAGG 15

( 2 ) INFORMATION FOR SEQ ID NO: 550:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 550:

AAACGUUACA AAGGC 15

( 2 ) INFORMATION FOR SEQ ID NO: 551:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 551:

AAAGGCUUAC UACCC 15

( 2 ) INFORMATION FOR SEQ ID NO: 552:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 552:

AAGGCUUACU ACCCA 15

( 2 ) INFORMATION FOR SEQ ID NO: 553:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 553:

GCUUACUACC CAAGG 15

( 2 ) INFORMATION FOR SEQ ID NO: 554:

( i ) SEQUENCE CHARACTERISTICS:

( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 554:

AGGACAUAGC CAACA                                                                                   15

( 2 ) INFORMATION FOR SEQ ID NO: 555:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 555:

AACAGCUUCU AUGAA                                                                                   15

( 2 ) INFORMATION FOR SEQ ID NO: 556:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 556:

ACAGCUUCUA UGAAG                                                                                   15

( 2 ) INFORMATION FOR SEQ ID NO: 557:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 557:

AGCUUCUAUG AAGUG                                                                                   15

( 2 ) INFORMATION FOR SEQ ID NO: 558:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 558:

GAAGUGUUUG AAAAA                                                                                   15

( 2 ) INFORMATION FOR SEQ ID NO: 559:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 559:

AAGUGUUUGA AAAAC                                                                                   15

( 2 ) INFORMATION FOR SEQ ID NO: 560:

( i ) SEQUENCE CHARACTERISTICS:
        ( A ) LENGTH: 15 base pairs
        ( B ) TYPE: nucleic acid (C) STRANDEDNESS: single
(D) TOPOLOGY: linear (xi) SEQUENCE DESCRIPTION: SEQ ID NO: 560:

AAAACAUCCC CACUU 15

(2) INFORMATION FOR SEQ ID NO: 561:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (xi) SEQUENCE DESCRIPTION: SEQ ID NO: 561:

CCCCACUUUA UAGAU 15

(2) INFORMATION FOR SEQ ID NO: 562:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (xi) SEQUENCE DESCRIPTION: SEQ ID NO: 562:

CCCACUUUAU AGAUG 15

(2) INFORMATION FOR SEQ ID NO: 563:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (xi) SEQUENCE DESCRIPTION: SEQ ID NO: 563:

CCACUUUAUA GAUGU 15

(2) INFORMATION FOR SEQ ID NO: 564:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (xi) SEQUENCE DESCRIPTION: SEQ ID NO: 564:

ACUUUAUAGA UGUUU 15

(2) INFORMATION FOR SEQ ID NO: 565:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (xi) SEQUENCE DESCRIPTION: SEQ ID NO: 565:

UAGAUGUUUU UGUUC 15

(2) INFORMATION FOR SEQ ID NO: 566:

(i) SEQUENCE CHARACTERISTICS:
  (A) LENGTH: 15 base pairs
  (B) TYPE: nucleic acid
  (C) STRANDEDNESS: single
  (D) TOPOLOGY: linear ( x i ) SEQUENCE DESCRIPTION: SEQ ID NO: 566:

AGAUGUUUUU GUUCA                                                                15

( 2 ) INFORMATION FOR SEQ ID NO: 567:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 567:

GAUGUUUUUG UUCAU                                                                15

( 2 ) INFORMATION FOR SEQ ID NO: 568:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 568:

AUGUUUUUGU UCAUU                                                                15

( 2 ) INFORMATION FOR SEQ ID NO: 569:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 569:

UUUUUGUUCA UUUUG                                                                15

( 2 ) INFORMATION FOR SEQ ID NO: 570:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 570:

UUUUGUUCAU UUUGG                                                                15

( 2 ) INFORMATION FOR SEQ ID NO: 571:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 571:

UGUUCAUUUU GGUAU                                                                15

( 2 ) INFORMATION FOR SEQ ID NO: 572:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 572:

GUUCAUUUUG GUAUA    15

(2) INFORMATION FOR SEQ ID NO: 573:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO: 573:

UUCAUUUUGG UAUAG    15

(2) INFORMATION FOR SEQ ID NO: 574:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO: 574:

UUUUGGUAUA GCACA    15

(2) INFORMATION FOR SEQ ID NO: 575:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO: 575:

UUGGUAUAGC ACAAU    15

(2) INFORMATION FOR SEQ ID NO: 576:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO: 576:

GCACAAUCUU CUACC    15

(2) INFORMATION FOR SEQ ID NO: 577:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO: 577:

ACAAUCUUCU ACCAG    15

(2) INFORMATION FOR SEQ ID NO: 578:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO: 578:

CAAUCUUCUA CCAGA    15

( 2 ) INFORMATION FOR SEQ ID NO: 579:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 579:

AUCUUCUACC AGAGG        15

( 2 ) INFORMATION FOR SEQ ID NO: 580:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 580:

UGGCAGUAGA GUUGA        15

( 2 ) INFORMATION FOR SEQ ID NO: 581:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 581:

GUAGAGUUGA AGGGA        15

( 2 ) INFORMATION FOR SEQ ID NO: 582:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 582:

AAGGGAUUUU UGCAG        15

( 2 ) INFORMATION FOR SEQ ID NO: 583:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 583:

AGGGAUUUUU GCAGG        15

( 2 ) INFORMATION FOR SEQ ID NO: 584:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 584:

GGGAUUUUUG CAGGA        15

( 2 ) INFORMATION FOR SEQ ID NO: 585:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 585:

GGAUUUUUGC AGGAU         15

( 2 ) INFORMATION FOR SEQ ID NO: 586:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 586:

GCAGGAUUGU UUAUG         15

( 2 ) INFORMATION FOR SEQ ID NO: 587:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 587:

GGAUUGUUUA UGAAU         15

( 2 ) INFORMATION FOR SEQ ID NO: 588:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 588:

GAUUGUUUAU GAAUG         15

( 2 ) INFORMATION FOR SEQ ID NO: 589:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 589:

AUUGUUUAUG AAUGC         15

( 2 ) INFORMATION FOR SEQ ID NO: 590:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 590:

AAUGCCUAUG GUGCA         15

( 2 ) INFORMATION FOR SEQ ID NO: 591:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 591:

GUGAUGUUAC GGUGG 15

( 2 ) INFORMATION FOR SEQ ID NO: 592:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 592:

UGAUGUUACG GUGGG 15

( 2 ) INFORMATION FOR SEQ ID NO: 593:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 593:

GGGGAGUCUU AGCAA 15

( 2 ) INFORMATION FOR SEQ ID NO: 594:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 594:

GGAGUCUUAG CAAAA 15

( 2 ) INFORMATION FOR SEQ ID NO: 595:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 595:

GAGUCUUAGC AAAAU 15

( 2 ) INFORMATION FOR SEQ ID NO: 596:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 596:

GCAAAAUCAG UUAAA 15

( 2 ) INFORMATION FOR SEQ ID NO: 597:

( i ) SEQUENCE CHARACTERISTICS:
    ( A ) LENGTH: 15 base pairs

```
            ( B ) TYPE: nucleic acid
            ( C ) STRANDEDNESS: single
            ( D ) TOPOLOGY: linear ( x i ) SEQUENCE DESCRIPTION: SEQ ID NO: 597:

AAUCAGUUAA AAAUA                                                                15
```

( 2 ) INFORMATION FOR SEQ ID NO: 598:

```
    ( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 598:

AUCAGUUAAA AAUAU                                                                15
```

( 2 ) INFORMATION FOR SEQ ID NO: 599:

```
    ( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 599:

UAAAAUAUU AUGUU                                                                 15
```

( 2 ) INFORMATION FOR SEQ ID NO: 600:

```
    ( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 600:

AAAAUAUUAU GUUAG                                                                15
```

( 2 ) INFORMATION FOR SEQ ID NO: 601:

```
    ( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 601:

AAAUAUUAUG UUAGG                                                                15
```

( 2 ) INFORMATION FOR SEQ ID NO: 602:

```
    ( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 602:

AUUAUGUUAG GACAU                                                                15
```

( 2 ) INFORMATION FOR SEQ ID NO: 603:

```
    ( i ) SEQUENCE CHARACTERISTICS:
            ( A ) LENGTH: 15 base pairs
            ( B ) TYPE: nucleic acid
            ( C ) STRANDEDNESS: single
```

( D ) TOPOLOGY: linear ( x i ) SEQUENCE DESCRIPTION: SEQ ID NO: 603:

UUAUGUUAGG ACAUG  15

( 2 ) INFORMATION FOR SEQ ID NO: 604:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 604:

ACAUGCUAGU GUGCA  15

( 2 ) INFORMATION FOR SEQ ID NO: 605:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 605:

AACAAGUUGU UGAGG  15

( 2 ) INFORMATION FOR SEQ ID NO: 606:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 606:

AAGUUGUUGA GGUUU  15

( 2 ) INFORMATION FOR SEQ ID NO: 607:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 607:

UUGAGGUUUA UGAAU  15

( 2 ) INFORMATION FOR SEQ ID NO: 608:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 608:

UGAGGUUUAU GAAUA  15

( 2 ) INFORMATION FOR SEQ ID NO: 609:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 609:

GAGGUUUAUG AAUAU                                                                                              15

( 2 ) INFORMATION FOR SEQ ID NO: 610:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 610:

UAUGAAUAUG CCCAA                                                                                              15

( 2 ) INFORMATION FOR SEQ ID NO: 611:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 611:

CAAAAAUUGG GUGGU                                                                                              15

( 2 ) INFORMATION FOR SEQ ID NO: 612:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 612:

GCAGGAUUCU ACCAU                                                                                              15

( 2 ) INFORMATION FOR SEQ ID NO: 613:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 613:

CAGGAUUCUA CCAUA                                                                                              15

( 2 ) INFORMATION FOR SEQ ID NO: 614:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 614:

GGAUUCUACC AUAUA                                                                                              15

( 2 ) INFORMATION FOR SEQ ID NO: 615:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 615:

CUACCAUAUA UUGAA 15

( 2 ) INFORMATION FOR SEQ ID NO: 616:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 616:

ACCAUAUAUU GAACA 15

( 2 ) INFORMATION FOR SEQ ID NO: 617:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 617:

CAUAUAUUGA ACAAC 15

( 2 ) INFORMATION FOR SEQ ID NO: 618:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 618:

AAAGCAUCAU UAUUA 15

( 2 ) INFORMATION FOR SEQ ID NO: 619:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 619:

GCAUCAUUAU UAUCU 15

( 2 ) INFORMATION FOR SEQ ID NO: 620:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 620:

CAUCAUUAUU AUCUU 15

( 2 ) INFORMATION FOR SEQ ID NO: 621:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 621:

UCAUUAUUAU CUUUG 15

( 2 ) INFORMATION FOR SEQ ID NO: 622:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 622:

CAUUAUUAUC UUUGA 15

( 2 ) INFORMATION FOR SEQ ID NO: 623:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 623:

UUAUUAUCUU UGACU 15

( 2 ) INFORMATION FOR SEQ ID NO: 624:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 624:

AUUAUCUUUG ACUCA 15

( 2 ) INFORMATION FOR SEQ ID NO: 625:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 625:

UUAUCUUUGA CUCAA 15

( 2 ) INFORMATION FOR SEQ ID NO: 626:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 626:

UUUGACUCAA UUUCC 15

( 2 ) INFORMATION FOR SEQ ID NO: 627:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 627:

ACUCAAUUUC CUCAC 15

( 2 ) INFORMATION FOR SEQ ID NO: 628:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 628:

CUCAAUUUCC UCACU                    15

( 2 ) INFORMATION FOR SEQ ID NO: 629:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 629:

UCAAUUUCCU CACUU                    15

( 2 ) INFORMATION FOR SEQ ID NO: 630:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 630:

AUUUCCUCAC UUCUC                    15

( 2 ) INFORMATION FOR SEQ ID NO: 631:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 631:

CCUCACUUCU CCAGU                    15

( 2 ) INFORMATION FOR SEQ ID NO: 632:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 632:

CUCACUUCUC CAGUG                    15

( 2 ) INFORMATION FOR SEQ ID NO: 633:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 633:

CACUUCUCCA GUGUA                    15

( 2 ) INFORMATION FOR SEQ ID NO: 634:

( i ) SEQUENCE CHARACTERISTICS:

(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 634:

CCAGUGUAGU AUUAG  15

(2) INFORMATION FOR SEQ ID NO: 635:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 635:

GUGUAGUAUU AGGCA  15

(2) INFORMATION FOR SEQ ID NO: 636:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 636:

GUAGUAUUAG GCAAU  15

(2) INFORMATION FOR SEQ ID NO: 637:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 637:

UAGUAUUAGG CAAUG  15

(2) INFORMATION FOR SEQ ID NO: 638:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 638:

CUGGCCUAGG CAUAA  15

(2) INFORMATION FOR SEQ ID NO: 639:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 639:

UAGGCAUAAU GGGAG  15

(2) INFORMATION FOR SEQ ID NO: 640:

(i) SEQUENCE CHARACTERISTICS:
(A) LENGTH: 15 base pairs
(B) TYPE: nucleic acid (C) STRANDEDNESS: single
        (D) TOPOLOGY: linear (xi) SEQUENCE DESCRIPTION: SEQ ID NO: 640:

GGAGAGUACA GAGGU                                                                                         15

(2) INFORMATION FOR SEQ ID NO: 641:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 641:

CAGAGGUACA CCGAG                                                                                         15

(2) INFORMATION FOR SEQ ID NO: 642:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 642:

GAGGAAUCAA GAUCU                                                                                         15

(2) INFORMATION FOR SEQ ID NO: 643:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 643:

UCAAGAUCUA UAUGA                                                                                         15

(2) INFORMATION FOR SEQ ID NO: 644:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 644:

AAGAUCUAUA UGAUG                                                                                         15

(2) INFORMATION FOR SEQ ID NO: 645:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 645:

GAUCUAUAUG AUGCA                                                                                         15

(2) INFORMATION FOR SEQ ID NO: 646:

(i) SEQUENCE CHARACTERISTICS:
        (A) LENGTH: 15 base pairs
        (B) TYPE: nucleic acid
        (C) STRANDEDNESS: single
        (D) TOPOLOGY: linear ( x i ) SEQUENCE DESCRIPTION: SEQ ID NO: 646:

AAGGCAUAUG CUGAA 15

( 2 ) INFORMATION FOR SEQ ID NO: 647:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 647:

AACAACUCAA AGAAA 15

( 2 ) INFORMATION FOR SEQ ID NO: 648:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 648:

GUGUGAUUAA CUACA 15

( 2 ) INFORMATION FOR SEQ ID NO: 649:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 649:

UGUGAUUAAC UACAG 15

( 2 ) INFORMATION FOR SEQ ID NO: 650:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 650:

AUUAACUACA GUGUA 15

( 2 ) INFORMATION FOR SEQ ID NO: 651:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 651:

ACAGUGUACU AGACU 15

( 2 ) INFORMATION FOR SEQ ID NO: 652:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 652:

GUGUACUAGA CUUGA  15

( 2 ) INFORMATION FOR SEQ ID NO: 653:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 653:

CUAGACUUGA CAGCA  15

( 2 ) INFORMATION FOR SEQ ID NO: 654:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 654:

AAGAACUAGA GGCUA  15

( 2 ) INFORMATION FOR SEQ ID NO: 655:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 655:

AGAGGCUAUC AAACA  15

( 2 ) INFORMATION FOR SEQ ID NO: 656:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 656:

AGGCUAUCAA ACAUC  15

( 2 ) INFORMATION FOR SEQ ID NO: 657:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 657:

CAAACAUCAG CUUAA  15

( 2 ) INFORMATION FOR SEQ ID NO: 658:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 658:

AUCAGCUUAA UCCAA  15

( 2 ) INFORMATION FOR SEQ ID NO: 659:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 659:

UCAGCUUAAU CCAAA     15

( 2 ) INFORMATION FOR SEQ ID NO: 660:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 660:

GCUUAAUCCA AAAGA     15

( 2 ) INFORMATION FOR SEQ ID NO: 661:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 661:

AAAAGAUAAU GAUGU     15

( 2 ) INFORMATION FOR SEQ ID NO: 662:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 662:

AUGAUGUAGA GCUUU     15

( 2 ) INFORMATION FOR SEQ ID NO: 663:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 663:

UAGAGCUUUG AGUUA     15

( 2 ) INFORMATION FOR SEQ ID NO: 664:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 664:

AGAGCUUUGA GUUAA     15

( 2 ) INFORMATION FOR SEQ ID NO: 665:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 665:

UUUGAGUUAA UAAAA  15

( 2 ) INFORMATION FOR SEQ ID NO: 666:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 666:

UUGAGUUAAU AAAAA  15

( 2 ) INFORMATION FOR SEQ ID NO: 667:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 667:

AUCUUUGCUG AUGAGGCCGA AAGGCCGAAA UUUGCC  36

( 2 ) INFORMATION FOR SEQ ID NO: 668:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 668:

UUGCUAACUG AUGAGGCCGA AAGGCCGAAA GCCAUC  36

( 2 ) INFORMATION FOR SEQ ID NO: 669:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 669:

CUUUGCUCUG AUGAGGCCGA AAGGCCGAAA GAGCCA  36

( 2 ) INFORMATION FOR SEQ ID NO: 670:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 670:

ACUUUGCCUG AUGAGGCCGA AAGGCCGAAA AGAGCC  36

( 2 ) INFORMATION FOR SEQ ID NO: 671:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (xi) SEQUENCE DESCRIPTION: SEQ ID NO: 671:

UCAACUUCUG AUGAGGCCGA AAGGCCGAAA CUUUGC                36

(2) INFORMATION FOR SEQ ID NO: 672:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (xi) SEQUENCE DESCRIPTION: SEQ ID NO: 672:

AUCAUUCCUG AUGAGGCCGA AAGGCCGAAA CUUGAC                36

(2) INFORMATION FOR SEQ ID NO: 673:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (xi) SEQUENCE DESCRIPTION: SEQ ID NO: 673:

UUGAGUGCUG AUGAGGCCGA AAGGCCGAAA UCAUUC                36

(2) INFORMATION FOR SEQ ID NO: 674:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (xi) SEQUENCE DESCRIPTION: SEQ ID NO: 674:

CUUUGUUCUG AUGAGGCCGA AAGGCCGAAA GUGUAU                36

(2) INFORMATION FOR SEQ ID NO: 675:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (xi) SEQUENCE DESCRIPTION: SEQ ID NO: 675:

AGAAGUUCUG AUGAGGCCGA AAGGCCGAAA UCUUUG                36

(2) INFORMATION FOR SEQ ID NO: 676:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (xi) SEQUENCE DESCRIPTION: SEQ ID NO: 676:

AUGACAGCUG AUGAGGCCGA AAGGCCGAAA GUUGAU                36

(2) INFORMATION FOR SEQ ID NO: 677:

(i) SEQUENCE CHARACTERISTICS:
  (A) LENGTH: 36 base pairs (B) TYPE: nucleic acid
        (C) STRANDEDNESS: single
        (D) TOPOLOGY: linear (xi) SEQUENCE DESCRIPTION: SEQ ID NO: 677:

GAUGACACUG AUGAGGCCGA AAGGCCGAAA AGUUGA  36

(2) INFORMATION FOR SEQ ID NO: 678:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 678:

GCUGGAUCUG AUGAGGCCGA AAGGCCGAAA CAGAAG  36

(2) INFORMATION FOR SEQ ID NO: 679:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 679:

UUUGCUGCUG AUGAGGCCGA AAGGCCGAAA UGACAG  36

(2) INFORMATION FOR SEQ ID NO: 680:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 680:

GAUGGUGCUG AUGAGGCCGA AAGGCCGAAA UUUGCU  36

(2) INFORMATION FOR SEQ ID NO: 681:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 681:

UCCGUUGCUG AUGAGGCCGA AAGGCCGAAA UGGUGU  36

(2) INFORMATION FOR SEQ ID NO: 682:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 682:

UCAAUACCUG AUGAGGCCGA AAGGCCGAAA UCUCCU  36

(2) INFORMATION FOR SEQ ID NO: 683:

(i) SEQUENCE CHARACTERISTICS:
        (A) LENGTH: 36 base pairs
        (B) TYPE: nucleic acid
        (C) STRANDEDNESS: single ( D ) TOPOLOGY: linear ( x i ) SEQUENCE DESCRIPTION: SEQ ID NO: 683:

GUAUCAACUG AUGAGGCCGA AAGGCCGAAA CUAUCU    36

( 2 ) INFORMATION FOR SEQ ID NO: 684:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 684:

GAGUAUCCUG AUGAGGCCGA AAGGCCGAAA UACUAU    36

( 2 ) INFORMATION FOR SEQ ID NO: 685:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 685:

UUAGGAGCUG AUGAGGCCGA AAGGCCGAAA UCAAUA    36

( 2 ) INFORMATION FOR SEQ ID NO: 686:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 686:

UAAUUAGCUG AUGAGGCCGA AAGGCCGAAA GUAUCA    36

( 2 ) INFORMATION FOR SEQ ID NO: 687:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 687:

UCAUAAUCUG AUGAGGCCGA AAGGCCGAAA GGAGUA    36

( 2 ) INFORMATION FOR SEQ ID NO: 688:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 688:

ACAUCAUCUG AUGAGGCCGA AAGGCCGAAA UUAGGA    36

( 2 ) INFORMATION FOR SEQ ID NO: 689:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 689:

CACAUCACUG AUGAGGCCGA AAGGCCGAAA AUUAGG    36

( 2 ) INFORMATION FOR SEQ ID NO: 690:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 690:

ACUUAUUCUG AUGAGGCCGA AAGGCCGAAA UGUGUU    36

( 2 ) INFORMATION FOR SEQ ID NO: 691:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 691:

CAUAACUCUG AUGAGGCCGA AAGGCCGAAA UUGAUG    36

( 2 ) INFORMATION FOR SEQ ID NO: 692:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 692:

GCCACAUCUG AUGAGGCCGA AAGGCCGAAA CUUAUU    36

( 2 ) INFORMATION FOR SEQ ID NO: 693:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 693:

UGCCACACUG AUGAGGCCGA AAGGCCGAAA ACUUAU    36

( 2 ) INFORMATION FOR SEQ ID NO: 694:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 694:

GAUUAAUCUG AUGAGGCCGA AAGGCCGAAA CAUGCC    36

( 2 ) INFORMATION FOR SEQ ID NO: 695:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 695:

UGAUUAACUG AUGAGGCCGA AAGGCCGAAA ACAUGC    36

(2) INFORMATION FOR SEQ ID NO: 696:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 696:

UGUGAUUCUG AUGAGGCCGA AAGGCCGAAA UAACAU    36

(2) INFORMATION FOR SEQ ID NO: 697:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 697:

CUGUGAUCUG AUGAGGCCGA AAGGCCGAAA AUAACA    36

(2) INFORMATION FOR SEQ ID NO: 698:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 698:

CUUCUGUCUG AUGAGGCCGA AAGGCCGAAA UUAAUA    36

(2) INFORMATION FOR SEQ ID NO: 699:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 699:

UUAUGAUCUG AUGAGGCCGA AAGGCCGAAA GCAUCU    36

(2) INFORMATION FOR SEQ ID NO: 700:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 700:

AAUUUAUCUG AUGAGGCCGA AAGGCCGAAA UUAGCA    36

(2) INFORMATION FOR SEQ ID NO: 701:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 701:

GUGAAUUCUG AUGAGGCCGA AAGGCCGAAA UGAUUA    36

( 2 ) INFORMATION FOR SEQ ID NO: 702:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 702:

CCCAGUGCUG AUGAGGCCGA AAGGCCGAAA UUUAUG         36

( 2 ) INFORMATION FOR SEQ ID NO: 703:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 703:

ACCCAGUCUG AUGAGGCCGA AAGGCCGAAA AUUUAU         36

( 2 ) INFORMATION FOR SEQ ID NO: 704:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 704:

ACCUAUUCUG AUGAGGCCGA AAGGCCGAAA CCCAGU         36

( 2 ) INFORMATION FOR SEQ ID NO: 705:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 705:

UACCUAUCUG AUGAGGCCGA AAGGCCGAAA ACCCAG         36

( 2 ) INFORMATION FOR SEQ ID NO: 706:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 706:

ACAUACCCUG AUGAGGCCGA AAGGCCGAAA UUAACC         36

( 2 ) INFORMATION FOR SEQ ID NO: 707:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 707:

UAUAACACUG AUGAGGCCGA AAGGCCGAAA CCUAUU         36

( 2 ) INFORMATION FOR SEQ ID NO: 708:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 708:

CGCAUAUCUG AUGAGGCCGA AAGGCCGAAA CAUACC    36

( 2 ) INFORMATION FOR SEQ ID NO: 709:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 709:

UCGCAUACUG AUGAGGCCGA AAGGCCGAAA ACAUAC    36

( 2 ) INFORMATION FOR SEQ ID NO: 710:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 710:

CAUCGCACUG AUGAGGCCGA AAGGCCGAAA UAACAU    36

( 2 ) INFORMATION FOR SEQ ID NO: 711:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 711:

UAACCUACUG AUGAGGCCGA AAGGCCGAAA CAUCGC    36

( 2 ) INFORMATION FOR SEQ ID NO: 712:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 712:

CCUAACCCUG AUGAGGCCGA AAGGCCGAAA GACAUC    36

( 2 ) INFORMATION FOR SEQ ID NO: 713:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 713:

UCUUCCUCUG AUGAGGCCGA AAGGCCGAAA CCUAGA    36

( 2 ) INFORMATION FOR SEQ ID NO: 714:

( i ) SEQUENCE CHARACTERISTICS:

(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 714:

CUCUUCCCUG AUGAGGCCGA AAGGCCGAAA ACCUAG    36

(2) INFORMATION FOR SEQ ID NO: 715:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 715:

GUAUUUCUG AUGAGGCCGA AAGGCCGAAA UGGUGU    36

(2) INFORMATION FOR SEQ ID NO: 716:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 716:

CUCUGAGCUG AUGAGGCCGA AAGGCCGAAA UUUUUA    36

(2) INFORMATION FOR SEQ ID NO: 717:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 717:

CAUCUCUCUG AUGAGGCCGA AAGGCCGAAA GUAUUU    36

(2) INFORMATION FOR SEQ ID NO: 718:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 718:

UACAUGACUG AUGAGGCCGA AAGGCCGAAA UCCCGC    36

(2) INFORMATION FOR SEQ ID NO: 719:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 719:

UUUACAUCUG AUGAGGCCGA AAGGCCGAAA UAUCCC    36

(2) INFORMATION FOR SEQ ID NO: 720:

(i) SEQUENCE CHARACTERISTICS:
(A) LENGTH: 36 base pairs
(B) TYPE: nucleic acid ( C ) STRANDEDNESS: single
( D ) TOPOLOGY: linear ( x i ) SEQUENCE DESCRIPTION: SEQ ID NO: 720:

UUGCUUUCUG AUGAGGCCGA AAGGCCGAAA CAUGAU 36

( 2 ) INFORMATION FOR SEQ ID NO: 721:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 721:

UUACAUCCUG AUGAGGCCGA AAGGCCGAAA CUCCAU 36

( 2 ) INFORMATION FOR SEQ ID NO: 722:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 722:

GUGUUGUCUG AUGAGGCCGA AAGGCCGAAA CAUCUA 36

( 2 ) INFORMATION FOR SEQ ID NO: 723:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 723:

UCUUGACCUG AUGAGGCCGA AAGGCCGAAA UGUGUU 36

( 2 ) INFORMATION FOR SEQ ID NO: 724:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 724:

AUGUCUUCUG AUGAGGCCGA AAGGCCGAAA CGAUGU 36

( 2 ) INFORMATION FOR SEQ ID NO: 725:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 725:

UUCCAUUCUG AUGAGGCCGA AAGGCCGAAA UGUCUU 36

( 2 ) INFORMATION FOR SEQ ID NO: 726:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 726:

UUUCCAUCUG AUGAGGCCGA AAGGCCGAAA AUGUCU　　　　　　　　　　　　36

( 2 ) INFORMATION FOR SEQ ID NO: 727:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 727:

CACUUCACUG AUGAGGCCGA AAGGCCGAAA UUUCAU　　　　　　　　　　　　36

( 2 ) INFORMATION FOR SEQ ID NO: 728:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 728:

ACACUUCCUG AUGAGGCCGA AAGGCCGAAA AUUUCA　　　　　　　　　　　　36

( 2 ) INFORMATION FOR SEQ ID NO: 729:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 729:

CAAUGUUCUG AUGAGGCCGA AAGGCCGAAA CACUUC　　　　　　　　　　　　36

( 2 ) INFORMATION FOR SEQ ID NO: 730:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 730:

CCAAUGUCUG AUGAGGCCGA AAGGCCGAAA ACACUU　　　　　　　　　　　　36

( 2 ) INFORMATION FOR SEQ ID NO: 731:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 731:

GCUUGCCCUG AUGAGGCCGA AAGGCCGAAA UGUUAA　　　　　　　　　　　　36

( 2 ) INFORMATION FOR SEQ ID NO: 732:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 732:

AGUUGUUCUG AUGAGGCCGA AAGGCCGAAA GCUUGC 36

( 2 ) INFORMATION FOR SEQ ID NO: 733:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 733:

CAGUUGUCUG AUGAGGCCGA AAGGCCGAAA AGCUUG 36

( 2 ) INFORMATION FOR SEQ ID NO: 734:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 734:

UGAUUUGCUG AUGAGGCCGA AAGGCCGAAA UUUCAG 36

( 2 ) INFORMATION FOR SEQ ID NO: 735:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 735:

UUGAUUUCUG AUGAGGCCGA AAGGCCGAAA AUUUCA 36

( 2 ) INFORMATION FOR SEQ ID NO: 736:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 736:

CAAUGUUCUG AUGAGGCCGA AAGGCCGAAA UUUGAA 36

( 2 ) INFORMATION FOR SEQ ID NO: 737:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 737:

CUAUCUCCUG AUGAGGCCGA AAGGCCGAAA UGUUGA 36

( 2 ) INFORMATION FOR SEQ ID NO: 738:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 738:

UAGAUUCCUG AUGAGGCCGA AAGGCCGAAA UCUCAA 36

( 2 ) INFORMATION FOR SEQ ID NO: 739:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 739:

UUUUCUACUG AUGAGGCCGA AAGGCCGAAA UUCUAU     36

( 2 ) INFORMATION FOR SEQ ID NO: 740:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 740:

GAUUUUCCUG AUGAGGCCGA AAGGCCGAAA GAUUCU     36

( 2 ) INFORMATION FOR SEQ ID NO: 741:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 741:

UUUGUAGCUG AUGAGGCCGA AAGGCCGAAA UUUUCU     36

( 2 ) INFORMATION FOR SEQ ID NO: 742:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 742:

UUUUUUGCUG AUGAGGCCGA AAGGCCGAAA GGAUUU     36

( 2 ) INFORMATION FOR SEQ ID NO: 743:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 743:

UUUCUUUCUG AUGAGGCCGA AAGGCCGAAA GCAUUU     36

( 2 ) INFORMATION FOR SEQ ID NO: 744:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 744:

CUGGAGCCUG AUGAGGCCGA AAGGCCGAAA CCUCUC     36

( 2 ) INFORMATION FOR SEQ ID NO: 745:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 745:

UAUUCUGCUG AUGAGGCCGA AAGGCCGAAA GCUACC    36

( 2 ) INFORMATION FOR SEQ ID NO: 746:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 746:

AUGCCUGCUG AUGAGGCCGA AAGGCCGAAA UUCUGG    36

( 2 ) INFORMATION FOR SEQ ID NO: 747:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 747:

AUCAGGACUG AUGAGGCCGA AAGGCCGAAA GUCAUG    36

( 2 ) INFORMATION FOR SEQ ID NO: 748:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 748:

CAAUCAGCUG AUGAGGCCGA AAGGCCGAAA GAGUCA    36

( 2 ) INFORMATION FOR SEQ ID NO: 749:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 749:

AUCCCACCUG AUGAGGCCGA AAGGCCGAAA UCAGGA    36

( 2 ) INFORMATION FOR SEQ ID NO: 750:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 750:

AUAAUAUCUG AUGAGGCCGA AAGGCCGAAA UCAUCC    36

( 2 ) INFORMATION FOR SEQ ID NO: 751:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 751:

UACAUAACUG AUGAGGCCGA AAGGCCGAAA UUAUCA 36

( 2 ) INFORMATION FOR SEQ ID NO: 752:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 752:

UAUACAUCUG AUGAGGCCGA AAGGCCGAAA UAUUAU 36

( 2 ) INFORMATION FOR SEQ ID NO: 753:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 753:

CUAUACACUG AUGAGGCCGA AAGGCCGAAA AUAUUA 36

( 2 ) INFORMATION FOR SEQ ID NO: 754:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 754:

GCUGCUACUG AUGAGGCCGA AAGGCCGAAA CAUAAU 36

( 2 ) INFORMATION FOR SEQ ID NO: 755:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 755:

AUGCUGCCUG AUGAGGCCGA AAGGCCGAAA UACAUA 36

( 2 ) INFORMATION FOR SEQ ID NO: 756:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 756:

UAUUACUCUG AUGAGGCCGA AAGGCCGAAA UGCUGC 36

( 2 ) INFORMATION FOR SEQ ID NO: 757:

( i ) SEQUENCE CHARACTERISTICS:
      ( A ) LENGTH: 36 base pairs (B) TYPE: nucleic acid
(C) STRANDEDNESS: single
(D) TOPOLOGY: linear (xi) SEQUENCE DESCRIPTION: SEQ ID NO: 757:

UUAUUACCUG AUGAGGCCGA AAGGCCGAAA AUGCUG    36

(2) INFORMATION FOR SEQ ID NO: 758:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 758:

UAGUUAUCUG AUGAGGCCGA AAGGCCGAAA CUAAUG    36

(2) INFORMATION FOR SEQ ID NO: 759:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 759:

AUUUAGUCUG AUGAGGCCGA AAGGCCGAAA UUACUA    36

(2) INFORMATION FOR SEQ ID NO: 760:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 760:

GCUAAUUCUG AUGAGGCCGA AAGGCCGAAA GUUAUU    36

(2) INFORMATION FOR SEQ ID NO: 761:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 761:

UGCUGCUCUG AUGAGGCCGA AAGGCCGAAA UUUAGU    36

(2) INFORMATION FOR SEQ ID NO: 762:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 762:

CUGCUGCCUG AUGAGGCCGA AAGGCCGAAA AUUUAG    36

(2) INFORMATION FOR SEQ ID NO: 763:

(i) SEQUENCE CHARACTERISTICS:
(A) LENGTH: 36 base pairs
(B) TYPE: nucleic acid
(C) STRANDEDNESS: single (D) TOPOLOGY: linear (xi) SEQUENCE DESCRIPTION: SEQ ID NO: 763:

AAGACCACUG AUGAGGCCGA AAGGCCGAAA UCUGUC    36

(2) INFORMATION FOR SEQ ID NO: 764:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 764:

GCUGUAACUG AUGAGGCCGA AAGGCCGAAA CCAGAU    36

(2) INFORMATION FOR SEQ ID NO: 765:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 765:

CGGCUGUCUG AUGAGGCCGA AAGGCCGAAA GACCAG    36

(2) INFORMATION FOR SEQ ID NO: 766:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 766:

ACGGCUGCUG AUGAGGCCGA AAGGCCGAAA AGACCA    36

(2) INFORMATION FOR SEQ ID NO: 767:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 767:

CUCUCCUCUG AUGAGGCCGA AAGGCCGAAA UCACGG    36

(2) INFORMATION FOR SEQ ID NO: 768:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 768:

GCUCUCCCUG AUGAGGCCGA AAGGCCGAAA AUCACG    36

(2) INFORMATION FOR SEQ ID NO: 769:

(i) SEQUENCE CHARACTERISTICS:
        (A) LENGTH: 36 base pairs
        (B) TYPE: nucleic acid
        (C) STRANDEDNESS: single
        (D) TOPOLOGY: linear ( x i ) SEQUENCE DESCRIPTION: SEQ ID NO: 769:

ACAUUAUCUG AUGAGGCCGA AAGGCCGAAA GCUCUC  36

( 2 ) INFORMATION FOR SEQ ID NO: 770:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 770:

AGGACAUCUG AUGAGGCCGA AAGGCCGAAA UUAGCU  36

( 2 ) INFORMATION FOR SEQ ID NO: 771:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 771:

UUUUUAGCUG AUGAGGCCGA AAGGCCGAAA CAUUAU  36

( 2 ) INFORMATION FOR SEQ ID NO: 772:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 772:

CAUUUUUCUG AUGAGGCCGA AAGGCCGAAA GGACAU  36

( 2 ) INFORMATION FOR SEQ ID NO: 773:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 773:

CCUUUGUCUG AUGAGGCCGA AAGGCCGAAA CGUUUC  36

( 2 ) INFORMATION FOR SEQ ID NO: 774:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 774:

GCCUUUGCUG AUGAGGCCGA AAGGCCGAAA ACGUUU  36

( 2 ) INFORMATION FOR SEQ ID NO: 775:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 775:

```
GGGUAGUCUG AUGAGGCCGA AAGGCCGAAA GCCUUU                                    36
```

(2) INFORMATION FOR SEQ ID NO: 776:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 776:

```
UGGGUAGCUG AUGAGGCCGA AAGGCCGAAA AGCCUU                                    36
```

(2) INFORMATION FOR SEQ ID NO: 777:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 777:

```
CCUUGGGCUG AUGAGGCCGA AAGGCCGAAA GUAAGC                                    36
```

(2) INFORMATION FOR SEQ ID NO: 778:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 778:

```
UGUUGGCCUG AUGAGGCCGA AAGGCCGAAA UGUCCU                                    36
```

(2) INFORMATION FOR SEQ ID NO: 779:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 779:

```
UUCAUAGCUG AUGAGGCCGA AAGGCCGAAA GCUGUU                                    36
```

(2) INFORMATION FOR SEQ ID NO: 780:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 780:

```
CUUCAUACUG AUGAGGCCGA AAGGCCGAAA AGCUGU                                    36
```

(2) INFORMATION FOR SEQ ID NO: 781:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 781:

```
CACUUCACUG AUGAGGCCGA AAGGCCGAAA GAAGCU                                    36
```

( 2 ) INFORMATION FOR SEQ ID NO: 782:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 782:

UUUUCACUG AUGAGGCCGA AAGGCCGAAA CACUUC      36

( 2 ) INFORMATION FOR SEQ ID NO: 783:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 783:

GUUUUCCUG AUGAGGCCGA AAGGCCGAAA ACACUU      36

( 2 ) INFORMATION FOR SEQ ID NO: 784:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 784:

AAGUGGGCUG AUGAGGCCGA AAGGCCGAAA UGUUUU      36

( 2 ) INFORMATION FOR SEQ ID NO: 785:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 785:

AUCUAUACUG AUGAGGCCGA AAGGCCGAAA GUGGGG      36

( 2 ) INFORMATION FOR SEQ ID NO: 786:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 786:

CAUCUAUCUG AUGAGGCCGA AAGGCCGAAA AGUGGG      36

( 2 ) INFORMATION FOR SEQ ID NO: 787:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 787:

ACAUCUACUG AUGAGGCCGA AAGGCCGAAA AAGUGG      36

( 2 ) INFORMATION FOR SEQ ID NO: 788:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 788:

AAACAUCCUG AUGAGGCCGA AAGGCCGAAA UAAAGU 36

( 2 ) INFORMATION FOR SEQ ID NO: 789:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 789:

GAACAAACUG AUGAGGCCGA AAGGCCGAAA CAUCUA 36

( 2 ) INFORMATION FOR SEQ ID NO: 790:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 790:

UGAACAACUG AUGAGGCCGA AAGGCCGAAA ACAUCU 36

( 2 ) INFORMATION FOR SEQ ID NO: 791:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 791:

AUGAACACUG AUGAGGCCGA AAGGCCGAAA AACAUC 36

( 2 ) INFORMATION FOR SEQ ID NO: 792:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 792:

AAUGAACCUG AUGAGGCCGA AAGGCCGAAA AAACAU 36

( 2 ) INFORMATION FOR SEQ ID NO: 793:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 793:

CAAAAUGCUG AUGAGGCCGA AAGGCCGAAA CAAAAA 36

( 2 ) INFORMATION FOR SEQ ID NO: 794:

( i ) SEQUENCE CHARACTERISTICS:

(A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 794:

CCAAAAUCUG AUGAGGCCGA AAGGCCGAAA ACAAAA 36

(2) INFORMATION FOR SEQ ID NO: 795:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 795:

AUACCAACUG AUGAGGCCGA AAGGCCGAAA UGAACA 36

(2) INFORMATION FOR SEQ ID NO: 796:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 796:

UAUACCACUG AUGAGGCCGA AAGGCCGAAA AUGAAC 36

(2) INFORMATION FOR SEQ ID NO: 797:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 797:

CUAUACCCUG AUGAGGCCGA AAGGCCGAAA AAUGAA 36

(2) INFORMATION FOR SEQ ID NO: 798:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 798:

UGUGCUACUG AUGAGGCCGA AAGGCCGAAA CCAAAA 36

(2) INFORMATION FOR SEQ ID NO: 799:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 799:

AUUGUGCCUG AUGAGGCCGA AAGGCCGAAA UACCAA 36

(2) INFORMATION FOR SEQ ID NO: 800:

(i) SEQUENCE CHARACTERISTICS:
        (A) LENGTH: 36 base pairs
        (B) TYPE: nucleic acid (C) STRANDEDNESS: single
(D) TOPOLOGY: linear (x i) SEQUENCE DESCRIPTION: SEQ ID NO: 800:

GGUAGAACUG AUGAGGCCGA AAGGCCGAAA UUGUGC　　　　36

(2) INFORMATION FOR SEQ ID NO: 801:

(i) SEQUENCE CHARACTERISTICS:
(A) LENGTH: 36 base pairs
(B) TYPE: nucleic acid
(C) STRANDEDNESS: single
(D) TOPOLOGY: linear (x i) SEQUENCE DESCRIPTION: SEQ ID NO: 801:

CUGGUAGCUG AUGAGGCCGA AAGGCCGAAA GAUUGU　　　　36

(2) INFORMATION FOR SEQ ID NO: 802:

(i) SEQUENCE CHARACTERISTICS:
(A) LENGTH: 36 base pairs
(B) TYPE: nucleic acid
(C) STRANDEDNESS: single
(D) TOPOLOGY: linear (x i) SEQUENCE DESCRIPTION: SEQ ID NO: 802:

UCUGGUACUG AUGAGGCCGA AAGGCCGAAA AGAUUG　　　　36

(2) INFORMATION FOR SEQ ID NO: 803:

(i) SEQUENCE CHARACTERISTICS:
(A) LENGTH: 36 base pairs
(B) TYPE: nucleic acid
(C) STRANDEDNESS: single
(D) TOPOLOGY: linear (x i) SEQUENCE DESCRIPTION: SEQ ID NO: 803:

CCUCUGGCUG AUGAGGCCGA AAGGCCGAAA GAAGAU　　　　36

(2) INFORMATION FOR SEQ ID NO: 804:

(i) SEQUENCE CHARACTERISTICS:
(A) LENGTH: 36 base pairs
(B) TYPE: nucleic acid
(C) STRANDEDNESS: single
(D) TOPOLOGY: linear (x i) SEQUENCE DESCRIPTION: SEQ ID NO: 804:

UCAACUCCUG AUGAGGCCGA AAGGCCGAAA CUGCCA　　　　36

(2) INFORMATION FOR SEQ ID NO: 805:

(i) SEQUENCE CHARACTERISTICS:
(A) LENGTH: 36 base pairs
(B) TYPE: nucleic acid
(C) STRANDEDNESS: single
(D) TOPOLOGY: linear (x i) SEQUENCE DESCRIPTION: SEQ ID NO: 805:

UCCCUUCCUG AUGAGGCCGA AAGGCCGAAA CUCUAC　　　　36

(2) INFORMATION FOR SEQ ID NO: 806:

(i) SEQUENCE CHARACTERISTICS:
(A) LENGTH: 36 base pairs
(B) TYPE: nucleic acid
(C) STRANDEDNESS: single
(D) TOPOLOGY: linear ( x i ) SEQUENCE DESCRIPTION: SEQ ID NO: 806:

CUGCAAACUG AUGAGGCCGA AAGGCCGAAA UCCCUU                36

( 2 ) INFORMATION FOR SEQ ID NO: 807:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 807:

CCUGCAACUG AUGAGGCCGA AAGGCCGAAA AUCCCU                36

( 2 ) INFORMATION FOR SEQ ID NO: 808:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 808:

UCCUGCACUG AUGAGGCCGA AAGGCCGAAA AAUCCC                36

( 2 ) INFORMATION FOR SEQ ID NO: 809:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 809:

AUCCUGCCUG AUGAGGCCGA AAGGCCGAAA AAAUCC                36

( 2 ) INFORMATION FOR SEQ ID NO: 810:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 810:

CAUAAACCUG AUGAGGCCGA AAGGCCGAAA UCCUGC                36

( 2 ) INFORMATION FOR SEQ ID NO: 811:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 811:

AUUCAUACUG AUGAGGCCGA AAGGCCGAAA CAAUCC                36

( 2 ) INFORMATION FOR SEQ ID NO: 812:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 812:

CAUUCAUCUG AUGAGGCCGA AAGGCCGAAA ACAAUC                36

( 2 ) INFORMATION FOR SEQ ID NO: 813:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 813:

GCAUUCACUG AUGAGGCCGA AAGGCCGAAA AACAAU                36

( 2 ) INFORMATION FOR SEQ ID NO: 814:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 814:

UGCACCACUG AUGAGGCCGA AAGGCCGAAA GGCAUU                36

( 2 ) INFORMATION FOR SEQ ID NO: 815:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 815:

CCACCGUCUG AUGAGGCCGA AAGGCCGAAA CAUCAC                36

( 2 ) INFORMATION FOR SEQ ID NO: 816:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 816:

CCCACCGCUG AUGAGGCCGA AAGGCCGAAA ACAUCA                36

( 2 ) INFORMATION FOR SEQ ID NO: 817:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 817:

UUGCUAACUG AUGAGGCCGA AAGGCCGAAA CUCCCC                36

( 2 ) INFORMATION FOR SEQ ID NO: 818:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 818:

UUUUGCUCUG AUGAGGCCGA AAGGCCGAAA GACUCC                36

( 2 ) INFORMATION FOR SEQ ID NO: 819:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 819:

AUUUUGCCUG AUGAGGCCGA AAGGCCGAAA AGACUC      36

( 2 ) INFORMATION FOR SEQ ID NO: 820:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 820:

UUUAACUCUG AUGAGGCCGA AAGGCCGAAA UUUUGC      36

( 2 ) INFORMATION FOR SEQ ID NO: 821:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 821:

UAUUUUUCUG AUGAGGCCGA AAGGCCGAAA CUGAUU      36

( 2 ) INFORMATION FOR SEQ ID NO: 822:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 822:

AUAUUUUCUG AUGAGGCCGA AAGGCCGAAA ACUGAU      36

( 2 ) INFORMATION FOR SEQ ID NO: 823:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 823:

AACAUAACUG AUGAGGCCGA AAGGCCGAAA UUUUUA      36

( 2 ) INFORMATION FOR SEQ ID NO: 824:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 824:

CUAACAUCUG AUGAGGCCGA AAGGCCGAAA UAUUUU      36

( 2 ) INFORMATION FOR SEQ ID NO: 825:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 825:

CCUAACACUG AUGAGGCCGA AAGGCCGAAA AUAUUU   36

( 2 ) INFORMATION FOR SEQ ID NO: 826:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 826:

AUGUCCUCUG AUGAGGCCGA AAGGCCGAAA CAUAAU   36

( 2 ) INFORMATION FOR SEQ ID NO: 827:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 827:

CAUGUCCUG AUGAGGCCGA AAGGCCGAAA ACAUAA   36

( 2 ) INFORMATION FOR SEQ ID NO: 828:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 828:

UGCACACCUG AUGAGGCCGA AAGGCCGAAA GCAUGU   36

( 2 ) INFORMATION FOR SEQ ID NO: 829:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 829:

CCUCAACCUG AUGAGGCCGA AAGGCCGAAA CUUGUU   36

( 2 ) INFORMATION FOR SEQ ID NO: 830:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 830:

AAACCUCCUG AUGAGGCCGA AAGGCCGAAA CAACUU   36

( 2 ) INFORMATION FOR SEQ ID NO: 831:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 831:

AUUCAUACUG AUGAGGCCGA AAGGCCGAAA CCUCAA 36

( 2 ) INFORMATION FOR SEQ ID NO: 832:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 832:

UAUUCAUCUG AUGAGGCCGA AAGGCCGAAA ACCUCA 36

( 2 ) INFORMATION FOR SEQ ID NO: 833:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 833:

AUAUUCACUG AUGAGGCCGA AAGGCCGAAA AACCUC 36

( 2 ) INFORMATION FOR SEQ ID NO: 834:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 834:

UUGGGCACUG AUGAGGCCGA AAGGCCGAAA UUCAUA 36

( 2 ) INFORMATION FOR SEQ ID NO: 835:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 835:

ACCACCCCUG AUGAGGCCGA AAGGCCGAAA UUUUUG 36

( 2 ) INFORMATION FOR SEQ ID NO: 836:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 836:

AUGGUAGCUG AUGAGGCCGA AAGGCCGAAA UCCUGC 36

( 2 ) INFORMATION FOR SEQ ID NO: 837:

( i ) SEQUENCE CHARACTERISTICS:
  ( A ) LENGTH: 36 base pairs (B) TYPE: nucleic acid
            (C) STRANDEDNESS: single
            (D) TOPOLOGY: linear (xi) SEQUENCE DESCRIPTION: SEQ ID NO: 837:

UAUGGUACUG AUGAGGCCGA AAGGCCGAAA AUCCUG                                    36

(2) INFORMATION FOR SEQ ID NO: 838:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 838:

UAUAUGGCUG AUGAGGCCGA AAGGCCGAAA GAAUCC                                    36

(2) INFORMATION FOR SEQ ID NO: 839:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 839:

UUCAAUACUG AUGAGGCCGA AAGGCCGAAA UGGUAG                                    36

(2) INFORMATION FOR SEQ ID NO: 840:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 840:

UGUUCAACUG AUGAGGCCGA AAGGCCGAAA UAUGGU                                    36

(2) INFORMATION FOR SEQ ID NO: 841:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 841:

GUUGUUCCUG AUGAGGCCGA AAGGCCGAAA UAUAUG                                    36

(2) INFORMATION FOR SEQ ID NO: 842:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 842:

UAAUAAUCUG AUGAGGCCGA AAGGCCGAAA UGCUUU                                    36

(2) INFORMATION FOR SEQ ID NO: 843:

(i) SEQUENCE CHARACTERISTICS:
            (A) LENGTH: 36 base pairs
            (B) TYPE: nucleic acid
            (C) STRANDEDNESS: single (D) TOPOLOGY: linear (xi) SEQUENCE DESCRIPTION: SEQ ID NO: 843:

AGAUAAUCUG AUGAGGCCGA AAGGCCGAAA UGAUGC     36

(2) INFORMATION FOR SEQ ID NO: 844:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 844:

AAGAUAACUG AUGAGGCCGA AAGGCCGAAA AUGAUG     36

(2) INFORMATION FOR SEQ ID NO: 845:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 845:

CAAAGAUCUG AUGAGGCCGA AAGGCCGAAA UAAUGA     36

(2) INFORMATION FOR SEQ ID NO: 846:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 846:

UCAAAGACUG AUGAGGCCGA AAGGCCGAAA AUAAUG     36

(2) INFORMATION FOR SEQ ID NO: 847:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 847:

AGUCAAACUG AUGAGGCCGA AAGGCCGAAA UAAUAA     36

(2) INFORMATION FOR SEQ ID NO: 848:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 848:

UGAGUCACUG AUGAGGCCGA AAGGCCGAAA GAUAAU     36

(2) INFORMATION FOR SEQ ID NO: 849:

(i) SEQUENCE CHARACTERISTICS:
        (A) LENGTH: 36 base pairs
        (B) TYPE: nucleic acid
        (C) STRANDEDNESS: single
        (D) TOPOLOGY: linear ( x i ) SEQUENCE DESCRIPTION: SEQ ID NO: 849:

UUGAGUCCUG AUGAGGCCGA AAGGCCGAAA AGAUAA    36

( 2 ) INFORMATION FOR SEQ ID NO: 850:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 850:

GGAAAUUCUG AUGAGGCCGA AAGGCCGAAA GUCAAA    36

( 2 ) INFORMATION FOR SEQ ID NO: 851:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 851:

GUGAGGACUG AUGAGGCCGA AAGGCCGAAA UUGAGU    36

( 2 ) INFORMATION FOR SEQ ID NO: 852:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 852:

AGUGAGGCUG AUGAGGCCGA AAGGCCGAAA AUUGAG    36

( 2 ) INFORMATION FOR SEQ ID NO: 853:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 853:

AAGUGAGCUG AUGAGGCCGA AAGGCCGAAA AAUUGA    36

( 2 ) INFORMATION FOR SEQ ID NO: 854:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 854:

GAGAAGUCUG AUGAGGCCGA AAGGCCGAAA GGAAAU    36

( 2 ) INFORMATION FOR SEQ ID NO: 855:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 855:

ACUGGAGCUG AUGAGGCCGA AAGGCCGAAA GUGAGG 36

( 2 ) INFORMATION FOR SEQ ID NO: 856:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 856:

CACUGGACUG AUGAGGCCGA AAGGCCGAAA AGUGAG 36

( 2 ) INFORMATION FOR SEQ ID NO: 857:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 857:

UACACUGCUG AUGAGGCCGA AAGGCCGAAA GAAGUG 36

( 2 ) INFORMATION FOR SEQ ID NO: 858:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 858:

CUAAUACCUG AUGAGGCCGA AAGGCCGAAA CACUGG 36

( 2 ) INFORMATION FOR SEQ ID NO: 859:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 859:

UGCCUAACUG AUGAGGCCGA AAGGCCGAAA CUACAC 36

( 2 ) INFORMATION FOR SEQ ID NO: 860:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 860:

AUUGCCUCUG AUGAGGCCGA AAGGCCGAAA UACUAC 36

( 2 ) INFORMATION FOR SEQ ID NO: 861:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 861:

CAUUGCCCUG AUGAGGCCGA AAGGCCGAAA AUACUA 36

( 2 ) INFORMATION FOR SEQ ID NO: 862:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 862:

UUAUGCCCUG AUGAGGCCGA AAGGCCGAAA GGCCAG      36

( 2 ) INFORMATION FOR SEQ ID NO: 863:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 863:

CUCCCAUCUG AUGAGGCCGA AAGGCCGAAA UGCCUA      36

( 2 ) INFORMATION FOR SEQ ID NO: 864:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 864:

ACCUCUGCUG AUGAGGCCGA AAGGCCGAAA CUCUCC      36

( 2 ) INFORMATION FOR SEQ ID NO: 865:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 865:

CUCGGUGCUG AUGAGGCCGA AAGGCCGAAA CCUCUG      36

( 2 ) INFORMATION FOR SEQ ID NO: 866:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 866:

AGAUCUUCUG AUGAGGCCGA AAGGCCGAAA UUCCUC      36

( 2 ) INFORMATION FOR SEQ ID NO: 867:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 867:

UCAUAUACUG AUGAGGCCGA AAGGCCGAAA UCUUGA      36

( 2 ) INFORMATION FOR SEQ ID NO: 868:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 868:

CAUCAUACUG AUGAGGCCGA AAGGCCGAAA GAUCUU          36

( 2 ) INFORMATION FOR SEQ ID NO: 869:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 869:

UGCAUCACUG AUGAGGCCGA AAGGCCGAAA UAGAUC          36

( 2 ) INFORMATION FOR SEQ ID NO: 870:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 870:

UUCAGCACUG AUGAGGCCGA AAGGCCGAAA UGCCUU          36

( 2 ) INFORMATION FOR SEQ ID NO: 871:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 871:

UUUCUUUCUG AUGAGGCCGA AAGGCCGAAA GUUGUU          36

( 2 ) INFORMATION FOR SEQ ID NO: 872:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 872:

UGUAGUUCUG AUGAGGCCGA AAGGCCGAAA UCACAC          36

( 2 ) INFORMATION FOR SEQ ID NO: 873:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 873:

CUGUAGUCUG AUGAGGCCGA AAGGCCGAAA AUCACA          36

( 2 ) INFORMATION FOR SEQ ID NO: 874:

( i ) SEQUENCE CHARACTERISTICS:

(A) LENGTH: 36 base pairs
(B) TYPE: nucleic acid
(C) STRANDEDNESS: single
(D) TOPOLOGY: linear (x i) SEQUENCE DESCRIPTION: SEQ ID NO: 874:

UACACUGCUG AUGAGGCCGA AAGGCCGAAA GUUAAU          36

(2) INFORMATION FOR SEQ ID NO: 875:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (x i) SEQUENCE DESCRIPTION: SEQ ID NO: 875:

AGUCUAGCUG AUGAGGCCGA AAGGCCGAAA CACUGU          36

(2) INFORMATION FOR SEQ ID NO: 876:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (x i) SEQUENCE DESCRIPTION: SEQ ID NO: 876:

UCAAGUCCUG AUGAGGCCGA AAGGCCGAAA GUACAC          36

(2) INFORMATION FOR SEQ ID NO: 877:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (x i) SEQUENCE DESCRIPTION: SEQ ID NO: 877:

UGCUGUCCUG AUGAGGCCGA AAGGCCGAAA GUCUAG          36

(2) INFORMATION FOR SEQ ID NO: 878:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (x i) SEQUENCE DESCRIPTION: SEQ ID NO: 878:

UAGCCUCCUG AUGAGGCCGA AAGGCCGAAA GUUCUU          36

(2) INFORMATION FOR SEQ ID NO: 879:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (x i) SEQUENCE DESCRIPTION: SEQ ID NO: 879:

UGUUUGACUG AUGAGGCCGA AAGGCCGAAA GCCUCU          36

(2) INFORMATION FOR SEQ ID NO: 880:

(i) SEQUENCE CHARACTERISTICS:
  (A) LENGTH: 36 base pairs
  (B) TYPE: nucleic acid ( C ) STRANDEDNESS: single
( D ) TOPOLOGY: linear ( x i ) SEQUENCE DESCRIPTION: SEQ ID NO: 880:

GAUGUUUCUG AUGAGGCCGA AAGGCCGAAA UAGCCU    36

( 2 ) INFORMATION FOR SEQ ID NO: 881:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 881:

UUAAGCUCUG AUGAGGCCGA AAGGCCGAAA UGUUUG    36

( 2 ) INFORMATION FOR SEQ ID NO: 882:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 882:

UUGGAUUCUG AUGAGGCCGA AAGGCCGAAA GCUGAU    36

( 2 ) INFORMATION FOR SEQ ID NO: 883:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 883:

UUUGGAUCUG AUGAGGCCGA AAGGCCGAAA AGCUGA    36

( 2 ) INFORMATION FOR SEQ ID NO: 884:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 884:

UCUUUUGCUG AUGAGGCCGA AAGGCCGAAA UUAAGC    36

( 2 ) INFORMATION FOR SEQ ID NO: 885:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 885:

ACAUCAUCUG AUGAGGCCGA AAGGCCGAAA UCUUUU    36

( 2 ) INFORMATION FOR SEQ ID NO: 886:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 886:

AAAGCUCCUG AUGAGGCCGA AAGGCCGAAA CAUCAU                         36

( 2 ) INFORMATION FOR SEQ ID NO: 887:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 887:

UAACUCACUG AUGAGGCCGA AAGGCCGAAA GCUCUA                         36

( 2 ) INFORMATION FOR SEQ ID NO: 888:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 888:

UUAACUCCUG AUGAGGCCGA AAGGCCGAAA AGCUCU                         36

( 2 ) INFORMATION FOR SEQ ID NO: 889:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 889:

UUUUAUUCUG AUGAGGCCGA AAGGCCGAAA CUCAAA                         36

( 2 ) INFORMATION FOR SEQ ID NO: 890:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 890:

UUUUUAUCUG AUGAGGCCGA AAGGCCGAAA ACUCAA                         36

( 2 ) INFORMATION FOR SEQ ID NO: 891:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 891:

CUGUGAUCAG AAGUCUUUAC CAGAGAAACA CACGUUGUGG UACAUUACCU GGUA     54

( 2 ) INFORMATION FOR SEQ ID NO: 892:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 892:

```
CAAGUGACAG AAGUCUCAAC CAGAGAAACA CACGUUGUGG UACAUUACCU GGUA          54
```

(2) INFORMATION FOR SEQ ID NO: 893:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO: 893:

```
CAGGCUCCAG AAGGACUAAC CAGAGAAACA CACGUUGUGG UACAUUACCU GGUA          54
```

(2) INFORMATION FOR SEQ ID NO: 894:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 894:

```
AAAGACUGAU GAUCACAG                                                  18
```

(2) INFORMATION FOR SEQ ID NO: 895:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 895:

```
UGAGACCGUU GUCACUUG                                                  18
```

(2) INFORMATION FOR SEQ ID NO: 896:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 896:

```
UAGUCCAGAU GGAGCCUG                                                  18
```

(2) INFORMATION FOR SEQ ID NO: 897:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO: 897:

```
AUCCCACAAG AAGGAGAGAC CAGAGAAACA CACGUUGUGG UACAUUACCU GGUA          54
```

(2) INFORMATION FOR SEQ ID NO: 898:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO: 898:

```
AAGACCAGAG AAGUCCCAC CAGAGAAACA CACGUUGUGG UACAUUACCU GGUA           54
```

( 2 ) INFORMATION FOR SEQ ID NO: 899:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 899:

CUAAUCACAG AAGUAAGAAC CAGAGAAACA CACGUUGUGG UACAUUACCU GGUA    54

( 2 ) INFORMATION FOR SEQ ID NO: 900:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 900:

UUCAUAGAAG AAGUUGGCAC CAGAGAAACA CACGUUGUGG UACAUUACCU GGUA    54

( 2 ) INFORMATION FOR SEQ ID NO: 901:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 901:

CCUAGGCCAG AAGCAUUGAC CAGAGAAACA CACGUUGUGG UACAUUACCU GGUA    54

( 2 ) INFORMATION FOR SEQ ID NO: 902:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 902:

UUGGAUUAAG AAGAUGUUAC CAGAGAAACA CACGUUGUGG UACAUUACCU GGUA    54

( 2 ) INFORMATION FOR SEQ ID NO: 903:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 903:

CUCUCCUGAU UGUGGGAU    18

( 2 ) INFORMATION FOR SEQ ID NO: 904:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 904:

GGGGACAGAU CUGGUCUU    18

( 2 ) INFORMATION FOR SEQ ID NO: 905:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 905:

UCUUACAGCC GUGAUUAG        18

( 2 ) INFORMATION FOR SEQ ID NO: 906:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 906:

GCCAACAGCU UCUAUGAA        18

( 2 ) INFORMATION FOR SEQ ID NO: 907:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 907:

CAAUGCUGCU GGCCUAGG        18

( 2 ) INFORMATION FOR SEQ ID NO: 908:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 908:

AACAUCAGCU UAAUCCAA        18

( 2 ) INFORMATION FOR SEQ ID NO: 909:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 909:

GGCCGAAAGG CC        12